(12) United States Patent  (10) Patent No.: US 7,901,867 B2
Wolf et al.  (45) Date of Patent: Mar. 8, 2011

(54) SULPHONIUM SALT INITIATORS

(75) Inventors: Jean-Pierre Wolf, Maisprach (CH);
Attila Latika, Bratislava (SK);
Jean-Luc Birbaum, Binningen (CH);
Stephan Ilg, Giebenach (CH); Pascal Hayoz, Hofstetten (CH)

(73) Assignee: BASF SE, Ludwigshafen (DE)

( * ) Notice: Subject to any disclaimer, the term of this patent is extended or adjusted under 35 U.S.C. 154(b) by 474 days.

(21) Appl. No.: 11/922,444

(22) PCT Filed: Jun. 21, 2006

(86) PCT No.: PCT/EP2006/063378
§ 371 (c)(1),
(2), (4) Date: Dec. 17, 2007

(87) PCT Pub. No.: WO2007/003507
PCT Pub. Date: Jan. 11, 2007

(65) Prior Publication Data
US 2009/0208872 A1 Aug. 20, 2009

(30) Foreign Application Priority Data
Jul. 1, 2005 (EP) .................................... 05105991

(51) Int. Cl.
G03F 7/004 (2006.01)
G03F 7/30 (2006.01)
C07C 381/12 (2006.01)

(52) U.S. Cl. .................. 430/270.1; 430/281.1; 430/325; 430/326; 430/921; 562/113; 568/18; 568/75; 568/77

(58) Field of Classification Search .............. 430/270.1, 430/326, 921, 281.1, 325; 562/113; 568/18, 568/75, 77
See application file for complete search history.

(56) References Cited

U.S. PATENT DOCUMENTS

| | | | |
|---|---|---|---|
| 6,358,665 B1 | 3/2002 | Pawlowski et al. | 430/270.1 |
| 6,406,830 B2 * | 6/2002 | Inoue et al. | 430/270.1 |
| 6,605,409 B2 * | 8/2003 | Kodama et al. | 430/270.1 |
| 6,723,483 B1 * | 4/2004 | Oono et al. | 430/170 |
| 7,033,727 B2 * | 4/2006 | Kodama | 430/270.1 |
| 7,101,998 B2 | 9/2006 | Herlihy et al. | 544/38 |
| 7,230,121 B2 | 6/2007 | Norcini et al. | 549/3 |
| 7,611,817 B2 * | 11/2009 | Nakayashiki et al. | 430/270.1 |
| 2002/0015913 A1 * | 2/2002 | Uetani et al. | 430/270.1 |
| 2002/0102491 A1 | 8/2002 | Kodama et al. | 430/270.1 |
| 2004/0197708 A1 | 10/2004 | Kodama | 430/311 |

FOREIGN PATENT DOCUMENTS

| | | |
|---|---|---|
| EP | 1 033 624 | 9/2000 |
| EP | 1 199 603 | 4/2002 |
| EP | 1 462 858 | 9/2004 |
| GB | 2 061 280 | 5/1981 |
| WO | 03/008404 | 1/2003 |
| WO | 03/072567 | 9/2003 |

* cited by examiner

Primary Examiner — John S Chu
(74) Attorney, Agent, or Firm — Shiela A. Loggins

(57) ABSTRACT

Compounds of the formula (I), (II), (III), (IV) and wherein, R is hydrogen, $C_1$-$C_{20}$alkyl; $C_2$-$C_{20}$alkyl interrupted by one or more O; is -L-X—$R_2$ or -L-$R_2$; $R_1$ has for example one of the meanings as given for R; $R_2$ is a monovalent sensitizer or photoinitiator moiety; $Ar_1$ and $Ar_2$ for example independently of one another are phenyl substituted by $C_1$-$C_{20}$alkyl, halogen or $OR_3$; or are unsubstituted naphthyl, anthryl, phenanthryl or biphenylyl; or are naphthyl, anthryl, phenanthryl or biphenylyl substituted by $C_1$-$C_{20}$alkyl, OH or $OR_3$; or are —$Ar_4$-A-$Ar_3$; $Ar_3$ is unsubstituted phenyl naphthyl, anthryl, phenanthryl or biphenylyl; or is phenyl, naphthyl, anthryl, phenanthryl or biphenylyl substituted by $C_1$-$C_{20}$alkyl, $OR_3$ or benzoyl; $Ar_4$ is phenylene, naphthylene, anthrylene or phenanthrylene; A is a direct bond, S, O or $C_1$-$C_{20}$alkylene; X is CO, C(O)O, OC(O), O, S or $NR_3$; L is $C_1$-$C_{20}$alkylene or $C_2$-$C_{20}$alkylene interrupted by one or more O; $R_3$ is $C_1$-$C_{20}$alkyl or $C_1$-$C_{20}$hydroxyalkyl; and Y is an anion, are suitable as photolatent acid generators.

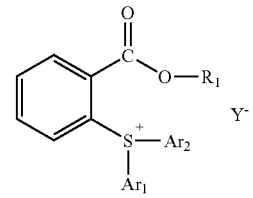

(I)

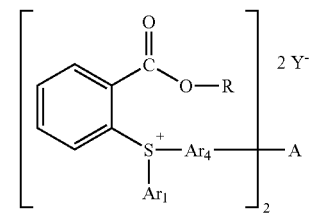

(II)

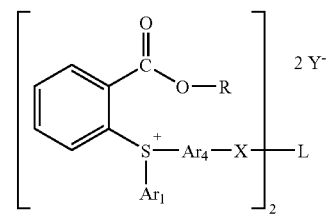

(III)

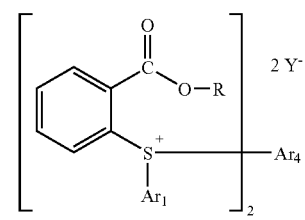

(IV)

13 Claims, No Drawings

SULPHONIUM SALT INITIATORS

The invention pertains to novel sulphonium salt photoinitiators and their use in photocurable compositions.

WO 03/072567 and WO 03/008404 disclose sulfonium salts, wherein the sulfonium ion is located in a condensed ring system, for example in the thioxanthyl moiety.

In EP 1033624 radiation-sensitive compositions for chemically amplified photoresists comprising onium salts are described. In said compositions inter alia sulfonium salts with fluoroalkylsulfonate anions are employed, for example 4-t-butyloxycarbonylphenyl diphenyl sulfonium 3,3,3,2,1,1-hexafluoropropane sulfonate or 4-t-butyloxycarbonylphenyl diphenyl sulfonium nonafluorobutane sulfonate.

One major problem of commercially available sulfonium salt photoinitiators is the formation of toxic and/or odorous break down products like diphenyl sulfide or benzene. In technique there is a need for effective cationic photoinitiators, which are reactive, in particular in both clear and pigmented coatings, thin and thick layers, with and without the addition of sensitizers as co-initiators, non toxic and which generate non toxic and odorless break down products and which further are low-yellowing.

It now has been found, that compounds of the formula I, II, III and IV

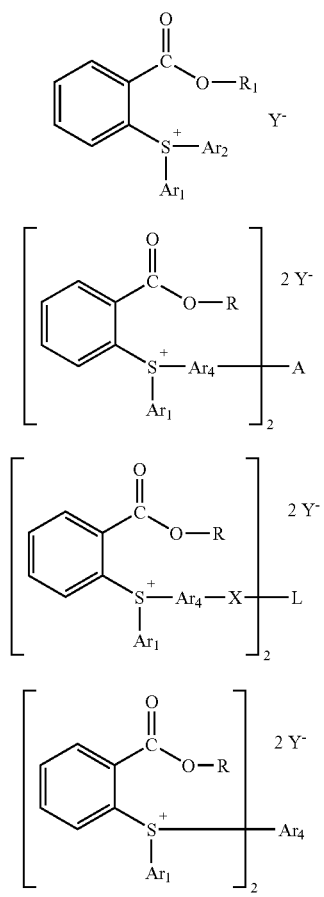

wherein
R is hydrogen, $C_1$-$C_{20}$alkyl; $C_2$-$C_{20}$alkyl interrupted by one or more O; is -L-X—$R_2$ or -L-$R_2$;

$R_1$ has one of the meanings as given for R or is

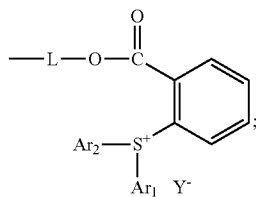

$R_2$ is a monovalent sensitizer or photoinitiator moiety;
$Ar_1$ and $Ar_2$ independently of one another are phenyl substituted by one or more $C_1$-$C_{20}$alkyl, halogen, $OR_3$ or $COOR_1$;
or are unsubstituted naphthyl, anthryl, phenanthryl or biphenylyl;
or are naphthyl, anthryl, phenanthryl or biphenylyl substituted by one or more $C_1$-$C_{20}$alkyl, OH or $OR_3$;
or are —$Ar_4$-A-$Ar_3$ or

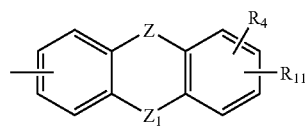

$Ar_3$ is unsubstituted phenyl, naphthyl, anthryl, phenanthryl or biphenylyl;
or is phenyl, naphthyl, anthryl, phenanthryl or biphenylyl substituted by one or more $C_1$-$C_{20}$alkyl, $OR_3$, $C_2$-$C_{12}$alkanoyl or benzoyl;
$Ar_4$ is phenylene, naphthylene, anthrylene or phenanthrylene;
A is a direct bond, S, O or $C_1$-$C_{20}$alkylene;
X is CO, C(O)O, OC(O), O, S or $NR_3$;
L is $C_1$-$C_{20}$alkylene or $C_2$-$C_{20}$alkylene interrupted by one or more O;
$R_3$ is $C_1$-$C_{20}$alkyl or $C_1$-$C_{20}$hydroxyalkyl; or is $C_1$-$C_{20}$alkyl substituted by $O(CO)R_{13}$;
Z is S, CO or $NR_3$;
$Z_1$ is a direct bond, $CH_2$, O or S;
$R_4$ and $R_{11}$ independently of one another are hydrogen, halogen, $C_1$-$C_8$alkyl, $C_1$-$C_8$alkoxy or phenyl;
$R_{13}$ is $C_1$-$C_{20}$alkyl; and
Y is an anion; are effective, low-yellowing photolatent sulfonium salts.

The compounds according to the invention are characterized in that one phenyl ring located at the S-atom bears an ester substituent in ortho position to the S-atom.

Said compounds excel at a good reactivity in combination with low yellowing and good solubility in the photocurable formulation.

The photolatent acid sulfonium salt compounds of formula I, I, III and IV exhibit a very satisfactory reactivity combined with good solubility and low yellowing properties. A very important advantage in view of environmental aspects is the fact that the compounds according to the present invention do not release benzene.

$C_1$-$C_{20}$alkyl is linear or branched and is, for example, $C_1$-$C_{18}$—, $C_1$-$C_{14}$—, $C_1$-$C_{12}$—, $C_1$-$C_8$—, $C_1$-$C_6$— or $C_1$-$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl and icosyl.

$C_1$-$C_{18}$alkyl, $C_1$-$C_{14}$alkyl, $C_1$-$C_{12}$alkyl, $C_1$-$C_8$alkyl, $C_1$-$C_6$alkyl and $C_1$-$C_4$alkyl have the same meanings as given above for $C_1$-$C_{20}$alkyl up to the corresponding number of C-atoms. $C_1$-$C_{20}$hydroxyalkyl is linear or branched, for example $C_1$-$C_{18}$—, $C_1$-$C_{12}$—, $C_1$-$C_{10}$— or $C_1$-$C_4$-alkyl mono- or poly-substituted by hydroxy, $C_1$-$C_{20}$-alkyl being as defined above. There are, for example, from one to three or one or two hydroxy substituents at the alkyl radical, preferably one hydroxy group is present. Examples are hydroxymethyl, hydroxyethyl, hydroxypropyl etc.

$C_2$-$C_{20}$alkyl interrupted by one or more O is for example interrupted 1-9, 1-7 or once or twice by O. In case the groups are interrupted by more than one O, said O-atoms are seperated from one another by at least one methylene group, i.e. the O-atoms are non-consecutive. Examples are the following structural units —$CH_2$—O—$CH_3$, —$CH_2CH_2$—O—$CH_2CH_3$, —$[CH_2CH_2O]_y$—$CH_3$, with y=1-9, —$(CH_2CH_2O)_7CH_2CH_3$, —$CH_2$—$CH(CH_3)$—O—$CH_2$—$CH_2CH_3$, or —$CH_2$—$CH(CH_3)$—O—$CH_2CH_3$.

Substituted by one or more groups denotes for example one to five substitutents, e.g. one, two or three substitutents.

Substituted phenyl is substituted one to four times, for example once, twice or three times, especially once or twice. Substituents on the phenyl ring are in position 2-, 3- or 4-, or in position 2,4-, 2,6-, 2,3-, 3,4-, 3,5-, 2,4,6-especially in position 2- or 4- of the phenyl ring. Naphthyl denotes 1-naphthyl and 2-naphthyl as well.

Anthryl, phenanthryl or biphenylyl are

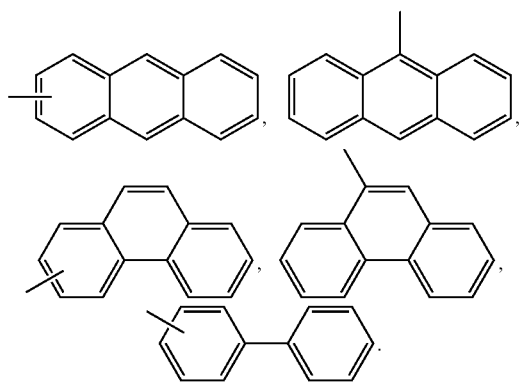

Substituted naphthyl, anthryl, phenanthryl or biphenylyl is substituted one to four times, for example once, twice or three times, preferably once.

Phenylene, naphthylene, anthrylene and phenanthrylene are

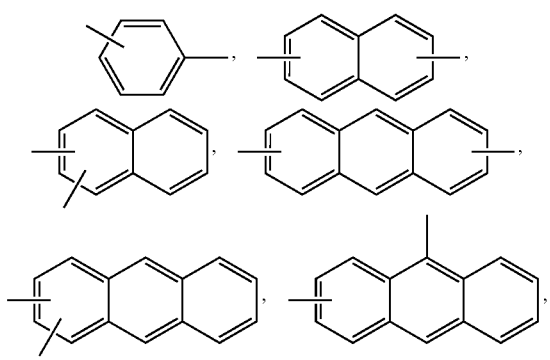

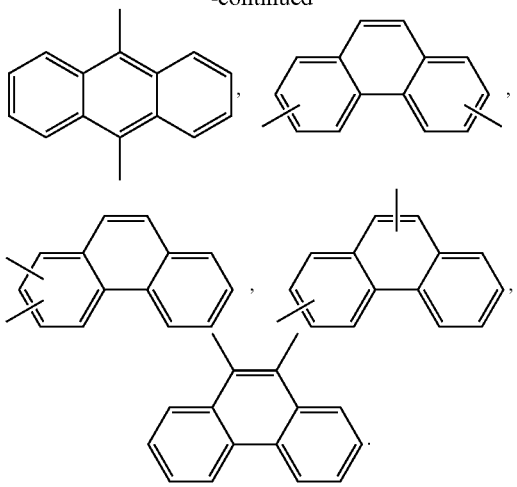

$C_1$-$C_{20}$alkylene is linear or branched, for example $C_1$-$C_{18}$—, $C_1$-$C_{12}$—, $C_1$-$C_{10}$—, $C_1$-$C_8$—, $C_1$-$C_7$—, $C_1$-$C_6$—, $C_1$-$C_4$-alkylene, e.g., methylene, ethylene, propylene, 1-methylethylene 1,1-dimethylethylene, butylene, 1-methylpropylene, 2-methyl-propylene, pentylene, hexylene, heptylene, octylene, nonylene, decylene, dodecylene, tetradecylene, hexadecylene or octadecylene.

$C_2$-$C_{20}$alkylene which is interrupted by one or more O is, for example, interrupted 1-9 times, for example 1-7 times or once or twice by O. This produces structural units such as, for example, —$CH_2$—O—$CH_2$—, —$CH_2CH_2$—O—$CH_2CH_2$—, —$[CH_2CH_2O]_y$—, —$[CH_2CH_2O]_y$—$CH_2$—, where y=1-9, —$(CH_2CH_2O)_7CH_2CH_2$—, —$CH_2$—CH$(CH_3)$—O—$CH_2$—$CH(CH_3)$— or —$CH_2$—$CH(CH_3)$—O—$CH_2$—$CH_2CH_2$—. In case the groups are interrupted by more than one O, said O-atoms are separated from one another by at least one methylene group, i.e. the O-atoms are non-consecutive. Said interrupted alkylene is linear or branched.

Examples for Y as an anion are halogenide, hydrogenosulfate, trifluoroacetate, or for example non-nucleophilic anions, selected from the group $(BF_4)^-$, $(SbF_6)^-$, $(PF_6)^-$, tetraphenylborate mono- or poly-substituted by halogen or trifluoromethyl, such as for example, $(B(C_6F_5)_4)^-$, $(B(C_6F_3Cl_2)_4)^-$, $(B(C_6F_4(CF_3)_4)^-$, or $(Ga(C_6F_5)_4)^-$, $C_1$-$C_{20}$alkylsulfonate, $C_1$-$C_{20}$haloalkylsulfonate, unsubstituted $C_6$-$C_{10}$arylsulfonate, camphorsulfonate, $C_1$-$C_{20}$-perfluoroalkylsulfonylmethide, $C_1$-$C_{20}$-perfluoroalkylsulfonylimide, and $C_6$-$C_{10}$arylsulfonate substituted by halogen, $NO_2$, $C_1$-$C_{12}$alkyl, $C_1$-$C_{12}$haloalkyl, $C_1$-$C_{12}$alkoxy, phenylsulfonyloxy, $C_1$-$C_4$alkylphenylsulfonyloxy or by $COOR_{100}$; wherein $R_{100}$ is $C_1$-$C_{20}$alkyl, phenyl, benzyl; or phenyl mono- or poly-substituted by $C_1$-$C_{12}$alkyl, $C_1$-$C_{12}$alkoxy or by halogen.

$C_1$-$C_{20}$Alkylsulfonate is $R_xSO_3^-$ wherein $R_x$ is linear or branched $C_1$-$C_{20}$alkyl as described above. Examples thereof include methylsulfonate, ethylsulfonate, propylsulfonate, pentylsulfonate and hexylsulfonate.

$C_2$-$C_{20}$Haloalkylsulfonate is $R_xSO_3^-$ wherein $R_x$ is halo-substituted $C_2$-$C_{20}$alkyl, $C_2$-$C_{10}$—, $C_2$-$C_8$— or $C_4$-$C_8$-alkyl. Examples thereof include $C_2F_5SO_3^-$, $C_4F_9SO_3^-$ and $C_8F_{17}SO_3^-$. $C_6$-$C_{10}$Arylsulfonate is $R_xSO_3^-$ wherein $R_x$ is $C_6$-$C_{10}$aryl, e.g. phenyl or naphthyl.

Alkyl-substituted arylsulfonates are, for example, toluenesulfonate, 2,4,6-trimethylbenzenesulfonate, 2,4,6-tris(isopropyl)benzenesulfonate, 4-tert-butylbenzenesulfonate and 4-dodecylbenzenesulfonate.

Halo-substituted arylsulfonates are, for example, 4-chlorobenzenesulfonate, 4-fluorobenzenesulfonate, 2,4,6-trifluorobenzenesulfonate and pentafluorobenzenesulfonate.

Camphorsulfonate is

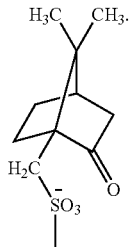

$C_1$-$C_{20}$-Perfluoroalkylsulfonylmethide is

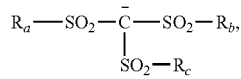

$C_1$-$C_{20}$ perfluoroalkylsulfonylimide is $R_a$—$SO_2$—$\bar{N}$—$SO_2$—$R_b$, wherein $R_a$, $R_b$ and $R_c$ independently of one another are $C_1$-$C_{20}$ perfluoroalkyl which is unsubstituted or is substituted by $N(R_d)(R_e)$, or $R_a$, $R_b$ and $R_c$ are phenyl substituted by $CF_3$; or $R_a$ and $R_b$ together are $C_1$-$C_6$-perfluoroalkylene, which optionally is interrupted by —O—; $R_d$ and $R_e$ independently of one another are $C_1$-$C_{12}$alkyl or $R_d$ and $R_e$ together are $C_1$-$C_6$ perfluorolkylene, which optionally is interrupted by O or $N(C_1$-$C_{12}$-Alkyl). Perfluoroalkyl is alkyl which is fully substituted by fluoro, i.e. the hydrogen atoms of the alkyl radical are replaced by fluoro. The same applies for the perfluoroalkylene.

Examples of such anions are $(C_2F_5SO_2)_2N^-$, $(C_4F_9SO_2)_2N^-$, $(C_8F_{17}SO_2)_3C^-$, $(CF_3SO_2)_3C^-$, $(CF_3SO_2)_2N^-$, $(C_4F_9SO_2)_3C^-$, $(CF_3SO_2)_2(C_4F_9SO_2)C^-$, $(CF_3SO_2)(C_4F_9SO_2)N^-$, $[(3,5-bis(CF_3)$—$(C_6H_3)SO_2]_2N^-$,

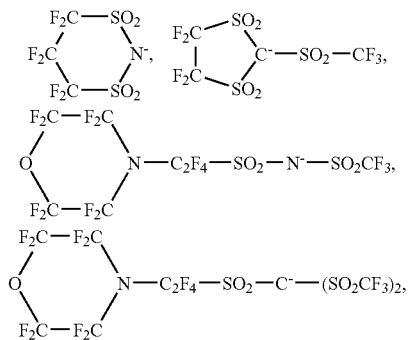

$C_6F_5SO_2C^-(SO_2CF_3)_2$, $C_6F_5SO_2N^-SO_2CF_3$. Such anions are known the person skilled in the art. The anions as well as their preparation are described e.g. in U.S. Pat. No. 5,554,664.

Halogen is fluorine, chlorine, bromine or iodine, especially chlorine or fluorine, preferably fluorine.

$C_1$-$C_{20}$Haloalkyl is a mono- or poly-halo-substituted $C_1$-$C_{20}$alkyl. The alkyl moiety can be substituted by a plurality of identical halogen atoms or, alternatively, by different halogen atoms.

When $C_1$-$C_{20}$alkyl is mono- or poly-halo-substituted, there are, for example, from 1 to 3, or 1 or 2, halogen substituents present on the alkyl moiety.

$C_1$-$C_{12}$Alkoxy denotes linear or branched radicals and is, for example, $C_1$-$C_8$—, $C_1$-$C_6$— or $C_1$-$C_4$-alkoxy. Examples thereof include methoxy, ethoxy, propoxy, isopropoxy, n-butyloxy, secbutyloxy, isobutyloxy, tert-butyloxy, pentyloxy, hexyloxy, heptyloxy, 2,4,4-trimethylpentyloxy, 2-ethylhexyloxy, octyloxy, nonyloxy, decyloxy and dodecyloxy, especially methoxy, ethoxy, propoxy, isopropoxy, n-butyloxy, sec-butyloxy, isobutyloxy and tert-butyloxy, preferably methoxy.

When $R_1$ is

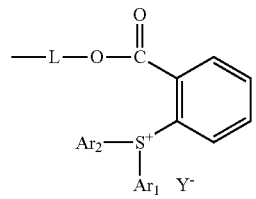

structures of the formula Ia are obtained

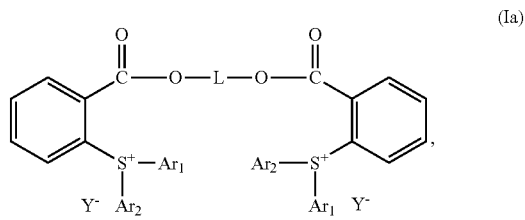

wherein L, $Ar_1$, $Ar_2$ and Y are as defined above.

$R_2$ as a monovalent sensitizer or photoinitiator moiety is for example

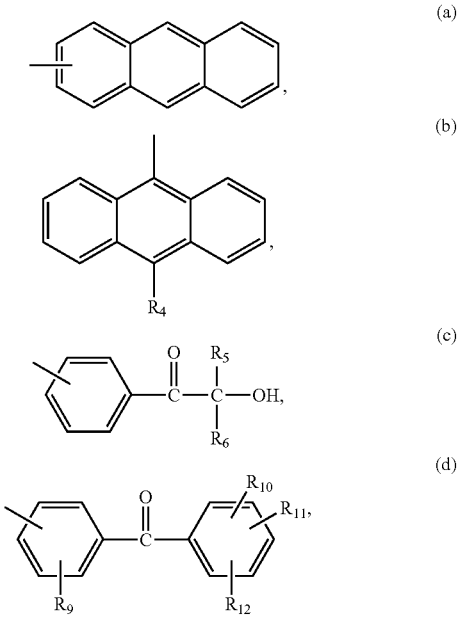

wherein $R_4$, $R_5$, $R_6$, $R_9$, $R_{10}$, $R_{11}$ and $R_{12}$ are as defined above.

Preferred are groups (c) and (d).

$Ar_1$ and $Ar_2$ as

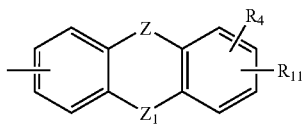

are for example

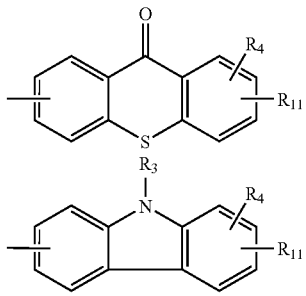

depending on the respective definitions given for Z and $Z_1$.

Preferred are xanthyl, thioxanthyl, isopropylthioxanthyl, diethylthioxanthyl, thianthrenyl and N-ethylcarbazolyl.

If $R_9$ and $R_{10}$ in group (d) together are methylene or S the following structures are covered

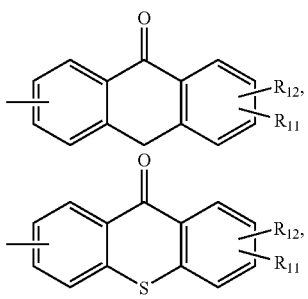

in particular

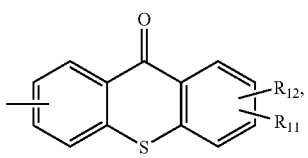

e.g. thioxanthyl or isoproylthioxanthyl.

Preferred are xanthyl, thioxanthyl, isopropylthioxanthyl, diethylthioxanthyl and thianthrenyl.

If radicals "A" are defined in different parts of the compounds of formula I, II, III and IV, said "A" may have identical or different meanings. The same applies for R as -L-X—$R_2$ and -L-$R_2$ and for $Ar_1$ and $Ar_2$ as —$Ar_4$-A-$Ar_3$: the meanings of the definitions, when occurring more than once in one molecule, i.e. the compound of the formula I, II, III and IV, may be the same or different.

The terms "and/or" or "or/and" in the present context is meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally substituted" means, that the radical to which it refers is either unsubstituted or substituted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

R is for example $C_1$-$C_{20}$alkyl; $C_2$-$C_{20}$alkyl interrupted by one or more O, -L-X—$R_2$ or -L-$R_2$. R in particular is $C_1$-$C_{12}$alkyl, -L-X—$R_2$ or -L-$R_2$. In another embodiment R is $C_1$-$C_{20}$alkyl.

$R_1$ is for example hydrogen, $C_1$-$C_{20}$alkyl; $C_2$-$C_{20}$alkyl interrupted by one or more O; or is —L-X—$R_2$ or

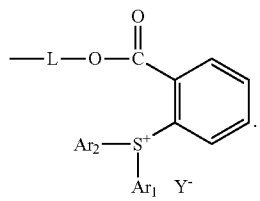

In particular $R_1$ is $C_1$-$C_{20}$alkyl.

$R_2$ as a monovalent sensitizer or photoinitiator moiety denotes for example a group (a), (b), (c) or (d)

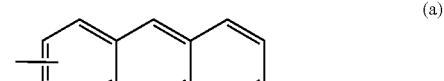 (a)

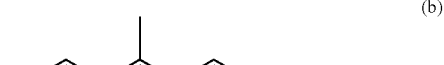 (b)

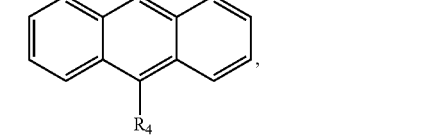 (c)

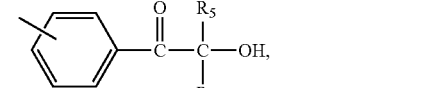 (d)

In particular $R_2$ is a group (a) or (c).

$Ar_1$ and $Ar_2$ preferably denote different groups and are not identical.

$Ar_1$ is for example phenyl substituted by $C_1$-$C_{20}$alkyl, halogen or $OR_3$; or is unsubstituted naphthyl, anthryl, phenanthryl or biphenylyl; or is naphthyl, anthryl, phenanthryl or biphenylyl substituted by $C_1$-$C_{20}$alkyl, OH or $OR_3$; or is —$Ar_4$-A-$Ar_3$ or

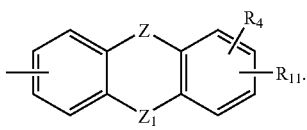

Ar₁ is for example phenyl substituted by $C_1$-$C_{12}$alkyl or $OR_3$; or is naphthyl, anthryl, phenanthryl, biphenylyl unsubstituted or substituted by $C_1$-$C_{12}$alkyl or $OR_3$; or is —Ar₄-A-Ar₃. In another embodiment Ar₁ is phenyl substituted by $OR_3$; or is biphenylyl or —Ar₄-A-Ar₃.

Ar₂ is for example phenyl substituted by $C_1$-$C_{12}$alkyl or $OR_3$; or is unsubstituted naphthyl, anthryl, phenanthryl or biphenylyl; or is naphthyl, anthryl, phenanthryl or biphenylyl substituted by $C_1$-$C_{12}$alkyl, OH or $OR_3$; or is —Ar₄-A-Ar₃ or

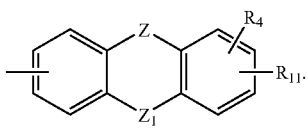

In another embodiment Ar₂ is phenyl substituted by $C_1$-$C_{20}$alkyl, or is biphenylyl, —Ar₄-A-Ar₃ or

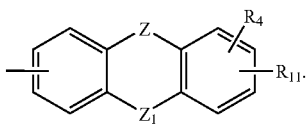

Ar₃ is for example unsubstituted phenyl, naphthyl or biphenylyl; or is phenyl, naphthyl or biphenylyl substituted by $C_1$-$C_{20}$alkyl, $OR_3$, $C_2$-$C_{12}$alkanoyl or benzoyl. In particular Ar₃ is phenyl or biphenylyl, both of which are unsubstituted or substituted by $C_1$-$C_{20}$alkyl, $OR_3$, $C_2$-$C_{12}$alkanoyl or benzoyl. In particular Ar₃ is phenyl, unsubstituted or substituted by $C_1$-$C_{20}$alkyl, $OR_3$, acetyl or benzoyl. In particular Ar₃ is phenyl unsubstituted or substituted by benzoyl.

Ar₄ is phenylene, naphthylene, anthrylene or phenanthrylene, in particular phenylene or naphthylene, especially phenylene.

A is a direct bond, S, O or $C_1$-$C_{20}$alkylene, in particular S, O or a direct bond, especially S or O.

X is CO, C(O)O, OC(O), O, S or NR₃. In particularly X denotes O, S, NR₃ or CO, especially O or S, preferably O.

L is $C_1$-$C_{20}$alkylene or $C_2$-$C_{20}$alkylene interrupted by one or more O. L is for example $C_1$-$C_{12}$alkylene or $C_2$-$C_{20}$alkylene interrupted by 1-8 O.

R₃ is $C_1$-$C_{20}$alkyl or $C_1$-$C_{20}$hydroxyalkyl; or is $C_1$-$C_{20}$alkyl substituted by O(CO)R₁₃. R₃ is for example $C_1$-$C_{12}$alkyl or $C_1$-$C_{12}$hydroxyalkyl; or is $C_1$-$C_{20}$alkyl substituted by O(CO)CH₃.

Z is S, CO or NR₃; in particular CO or NR₃, preferably NR₃.

Z₁ a direct bond, CH₂, O or S; in particular a direct bond or S, preferably a direct bond.

is an anion, for example a halogenide, hydrogenosulfate, trifluoroacetate or a non-nucleophilic anion, for example selected from the group $(BF_4)^-$, $(SbF_6)^-$, $(PF_6)^-$, $(B(C_6F_5)_4)^-$, $(B(C_6F_3Cl_2)_4)^-$, $(B(C_6F_4(CF_3))_4)^-$, $(Ga(C_6F_5)_4)^-$, $C_1$-$C_{20}$alkylsulfonate, $C_1$-$C_{20}$haloalkylsulfonate, unsubstituted $C_6$-$C_{10}$arylsulfonate, camphorsulfonate, $C_1$-$C_{20}$-perfluoroalkylsulfonylmethide, $C_1$-$C_{20}$-perfluoroalkylsulfonylimide, and $C_6$-$C_{10}$arylsulfonate substituted by halogen, $NO_2$, $C_1$-$C_{12}$alkyl, $C_1$-$C_{12}$haloalkyl, $C_1$-$C_{12}$alkoxy, phenylsulfonyloxy, $C_1$-$C_4$alkylphenylsulfonyloxy or by $COOR_{100}$; and R₁₀₀ is $C_1$-$C_{20}$alkyl, phenyl, benzyl; or phenyl mono- or poly-substituted by $C_1$-$C_{12}$alkyl, $C_1$-$C_{12}$alkoxy or by halogen.

Y preferably is a non-nucleophilic anion, for example selected from the group $(BF_4)^-$, $(SbF_6)^-$, $(PF_6)^-$, $(B(C_6F_5)_4)^-$, $(Ga(C_6F_5)_4)^-$, $C_1$-$C_{20}$alkylsulfonate, $C_1$-$C_{20}$haloalkylsulfonate, $C_6$-$C_{10}$arylsulfonate and camphorsulfonate. In particular Y is a non-nucleophilic anion, selected from the group $(BF_4)^-$, $(SbF_6)^-$, $(PF_6)^-$ and $(B(C_6F_5)_4)^-$, preferably $(PF_6)^-$.

In particular interesting are compounds of the formula I and II as defined above.

Preferred are compounds of the formula I, II, III and IV, wherein

Y is a halogenide, hydrogenosulfate, trifluoroacetate, or a non-nucleophilic anion, selected from the group $(BF_4)^-$, $(SbF_6)^-$, $(PF_6)^-$, $(B(C_6F_5)_4)^-$, $C_1$-$C_{20}$alkylsulfonate, $C_1$-$C_{20}$haloalkylsulfonate, unsubstituted $C_6$-$C_{10}$arylsulfonate, camphorsulfonate, $C_1$-$C_{20}$-perfluoroalkylsulfonylmethide, $C_1$-$C_{20}$-perfluoroalkylsulfonylimide, and $C_6$-$C_{10}$arylsulfonate substituted by halogen, $NO_2$, $C_1$-$C_{12}$alkyl, $C_1$-$C_{12}$haloalkyl, $C_1$-$C_{12}$alkoxy, phenylsulfonyloxy, $C_1$-$C_4$alkylphenylsulfonyloxy or by $COOR_{100}$; wherein $R_{100}$ is $C_1$-$C_{20}$alkyl, phenyl, benzyl; or phenyl mono- or poly-substituted by $C_1$-$C_{12}$alkyl, $C_1$-$C_{12}$alkoxy or by halogen.

Interesting further are compounds of the formula I, II, III and IV, wherein

R₂ denotes a group (a), (b), (c) or (d)

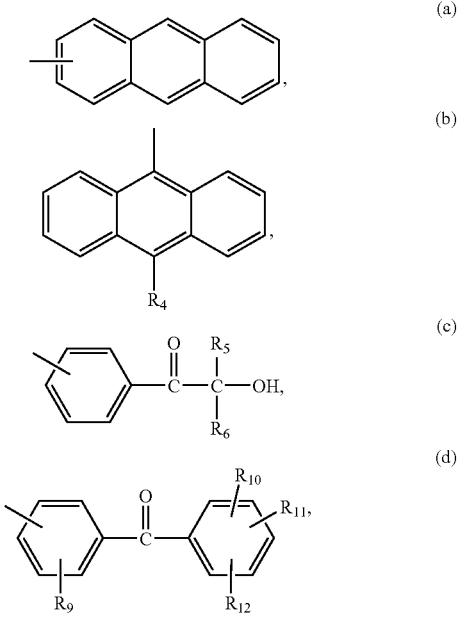

R₄ is hydrogen, $C_1$-$C_4$alkyl or $C_1$-$C_4$alkoxy;

R₅ and R₆ independently of one another are $C_1$-$C_{20}$alkyl, $C_2$-$C_{20}$alkenyl, phenylalkyl, alkylphenylalkyl, or R₅ and R₆ together with the C-atom to which they are attached form a ring;

$R_9$, $R_{10}$, $R_{11}$, and $R_{12}$ independently of one another are hydrogen, halogen, $C_1$-$C_8$alkyl or phenyl, or $R_9$ and $R_{10}$ together are methylene or S.

In particular preferred are compounds of the formula I and II, wherein
$R_2$ is $C_1$-$C_{20}$alkyl;
$R_1$ is hydrogen, $C_1$-$C_{20}$alkyl; $C_2$-$C_{20}$alkyl interrupted by one or more O; is -L-X—$R_2$; or is

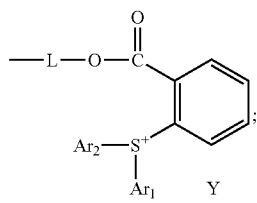

$R_2$ is a group (a) or (c)

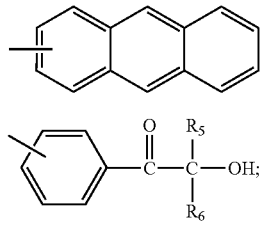

(a)

(c)

$Ar_1$ is phenyl substituted by one or more $OR_3$; or is biphenylyl or —$Ar_4$-A-$Ar_3$;
$Ar_2$ is phenyl substituted by one or more $C_1$-$C_{20}$alkyl; or is biphenylyl; —$Ar_4$-A-$Ar_3$ or

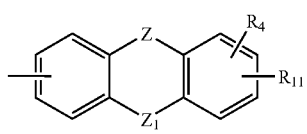

$Ar_3$ is unsubstituted phenyl; or is phenyl, substituted by acetyl or benzoyl;
$Ar_4$ is phenylene;
A is S or O;
X is O;
L is $C_1$-$C_{20}$alkylene or $C_2$-$C_{20}$alkylene interrupted by one or more O;
$R_3$ is $C_1$-$C_{20}$alkyl or $C_1$-$C_{20}$hydroxyalkyl; or is $C_1$-$C_{20}$alkyl substituted by $O(CO)R_{13}$;
$R_4$ and $R_{11}$ are hydrogen;
$R_{13}$ is $C_1$-$C_{20}$alkyl;
Z is $NR_3$;
$Z_1$ is a direct bond;
Y is $PF_6$ or $C_2$-$C_{20}$haloalkylsulfonate.

The compounds according to the present invention can for example be prepared by converting dithiobisbenzoic acid to its di-ester by acid-catalyzed (for example, with sulfuric acid) esterification with an alcohol, for example, methanol, ethanol, or isopropanol. Since the starting diacid has a poor solubility in the alcohol, it may be convenient to add a co-solvent such as dioxane, tetrahydrofuran, or 1,2-dichlorobenzene. Esterification methods are well known and proceed typically at the reflux temperature of the alcohol or boiling point of the azeotrope. Water liberated in the process is typically removed by azeotropic distillation. It is also convenient to convert dithiobisbenzoic acid to its dichloride, before treatment with the alcohol to obtain the diester. Suitable chlorination methods are for example, thionyl chloride (as solvent or in nearly stoechiometric amount and diluted with a solvent such as dichloromethane, tetrachloroethane, or 1,2-dichlorobenzene) in the presence of dimethyl formamide and/or a phase transfer catalyst. Alternatively, phosphorus trichloride can also be used as chlorination reagent. Cleavage of the S—S bond with sulfuryl chloride (or $Cl_2$) affords ortho-chlorosulfenyl alkyl benzoates in good yields. The following scheme illustrates a typical reaction sequence:

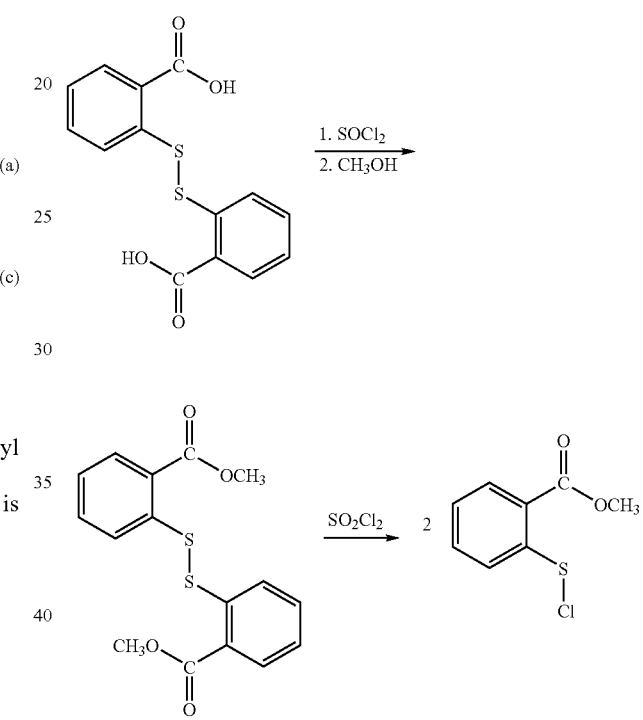

Said ortho-chlorosulfenyl alkyl benzoates, preferably ortho-chlorosulfenyl methyl benzoate, is the ideal starting material for the synthesis of diaryl sulfides by reaction with a large variety of arene compounds under Friedel-Crafts-like conditions, for example, in the presence of $AlCl_3$ in an excess of the arene or in an inert solvent such as dichloromethane, tetrachloroethane, or 1,2-dichlorobenzene at typical temperatures of −20-100° C. These sulfides are then oxidized under well known oxidation conditions, by organic peroxides, such as peracetic acid or m-chloroperbenzoic acid, or inorganic peroxides such as hydrogen peroxide in acetic acid:

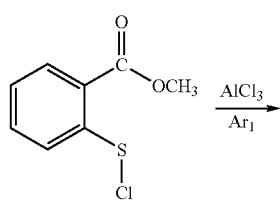

-continued

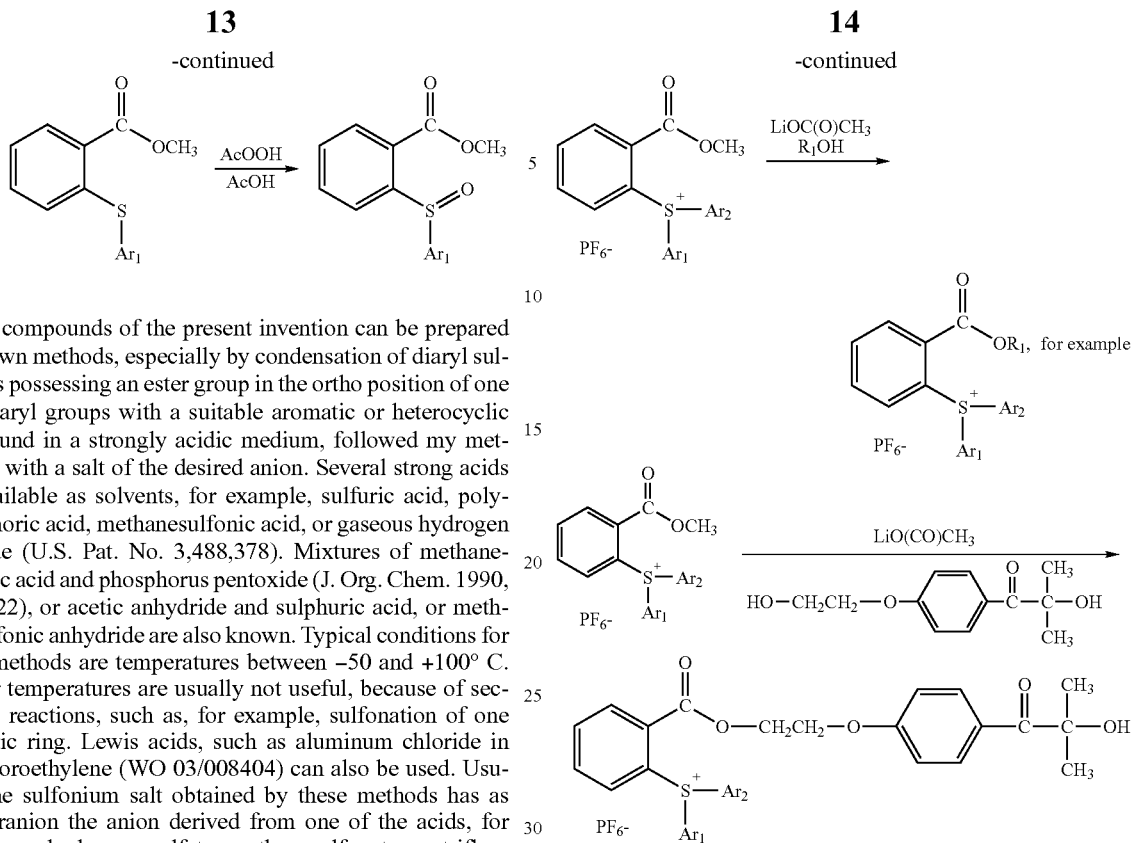

The compounds of the present invention can be prepared by known methods, especially by condensation of diaryl sulfoxides possessing an ester group in the ortho position of one of the aryl groups with a suitable aromatic or heterocyclic compound in a strongly acidic medium, followed my metathesis with a salt of the desired anion. Several strong acids are available as solvents, for example, sulfuric acid, polyphosphoric acid, methanesulfonic acid, or gaseous hydrogen chloride (U.S. Pat. No. 3,488,378). Mixtures of methanesulfonic acid and phosphorus pentoxide (J. Org. Chem. 1990, 55, 4222), or acetic anhydride and sulphuric acid, or methanesulfonic anhydride are also known. Typical conditions for these methods are temperatures between −50 and +100° C. Higher temperatures are usually not useful, because of secondary reactions, such as, for example, sulfonation of one aromatic ring. Lewis acids, such as aluminum chloride in terachloroethylene (WO 03/008404) can also be used. Usually, the sulfonium salt obtained by these methods has as counteranion the anion derived from one of the acids, for instance, a hydrogenosulfate, methanesulfonate, or trifluoromethanesulfonate.

Conditions without metathesis, such as arylation in acetic acid/acetic anhydride/sulfuric acid in the presence of potassium hexafluorophosphate or aqueous 75% $HPF_6$ are described for example in US patent application publication 2004/0030158. The following scheme illustrates the final steps of the synthesis.

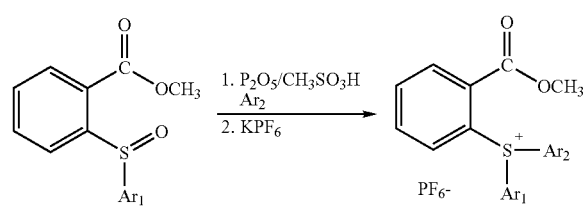

The synthesis is extremely versatile, as it allows the introduction of a large number of aryl groups. $Ar_1$ and $Ar_2$ can basically be any aryl group, which can be acylated via a Friedel-Crafts type reaction.

In addition, the ester group can be hydrolysed to COOH or it can undergo a trans-esterification reaction with an alcohol derivative:

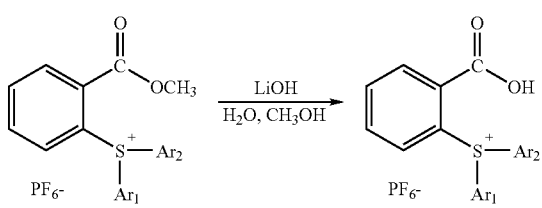

affords a sulfonium salt with $R_1$=L-X—$R_2$, wherein $R_2$ is a photoinitiating moiety.

The compounds of the formula I, II, III and IV are used as photolatent acids, i.e compounds that upon irradiation release an acid.

Accordingly, an object of the invention is a radiation-sensitive composition comprising
(a1) a cationically or acid-catalytically polymerisable or crosslinkable compound or
(a2) a compound that increases its solubility in a developer under the action of acid; and
(b) at least one compound of the formula I, II, III or IV as described above.

The compositions according to the invention comprise as component (a1), for example, resins and compounds that can be cationically polymerised by alkyl- or aryl-containing cations or by protons. Examples thereof include cyclic ethers, especially epoxides and oxetanes, and also vinyl ethers and hydroxy-containing compounds. Lactone compounds and cyclic thioethers as well as vinyl thioethers can also be used. Further examples include aminoplastics or phenolic resole resins. These are especially melamine, urea, epoxy, phenolic, acrylic, polyester and alkyd resins, but especially mixtures of acrylic, polyester or alkyd resins with a melamine resin. These include also modified surface-coating resins, such as, for example, acrylic-modified polyester and alkyd resins. Examples of individual types of resins that are included under the terms acrylic, polyester and alkyd resins are described, for example, in Wagner, Sarx/Lackkunstharze (Munich, 1971), pages 86 to 123 and 229 to 238, or in U11-mann/Encyclopädie der techn. Chemie, 4$^{th}$ edition, volume 15 (1978), pages 613 to 628, or Ullmann's Encyclopedia of Industrial Chemistry, Verlag Chemie, 1991, Vol. 18, 360 ff., Vol. A19, 371 ff. The surface-coating preferably comprises an amino resin. Examples thereof include etherified and non-etherified melamine, urea, guanidine and biuret resins. Of special importance is acid catalysis for the curing of surface-coatings comprising etherified amino resins, such as, for example, methylated or butylated melamine resins (N-methoxymethyl- or N-butoxymethyl-melamine) or methylated/butylated glycolurils.

It is possible, for example, to use all customary epoxides, such as aromatic, aliphatic or cycloaliphatic epoxy resins. These are compounds having at least one, preferably at least two, epoxy group(s) in the molecule. Examples thereof are the glycidyl ethers and 5-methyl glycidyl ethers of aliphatic or cycloaliphatic diols or polyols, e.g. those of ethylene glycol, propane-1,2-diol, propane-1,3-diol, butane-1,4-diol, diethylene glycol, polyethylene glycol, polypropylene glycol, glycerol, trimethylolpropane or 1,4-dimethylolcyclohexane or of 2,2-bis(4-hydroxycyclohexyl)propane and N,N-bis (2-hydroxyethyl)aniline; the glycidyl ethers of di- and polyphenols, for example of resorcinol, of 4,4'-dihydroxyphenyl-2,2-propane, of novolaks or of 1,1,2,2-tetrakis(4-hydroxyphenyl)ethane. Examples thereof include phenyl glycidyl ether, p-tert-butyl glycidyl ether, o-icresyl glycidyl ether, polytetrahydrofuran glycidyl ether, n-butyl glycidyl ether, 2-ethylhexylglycidylether, $C_{12/15}$alkyl glycidyl ether and cyclohexanedimethanol diglycidyl ether. Further examples include N-glycidyl compounds, for example the glycidyl compounds of ethyleneurea, 1,3-propyleneurea or 5-dimethyl-hydantoin or of 4,4'-methylene-5,5'-tetramethyldihydantoin, or compounds such as triglycidyl isocyanurate.

Further examples of glycidyl ether components (a1) that are used in the formulations according to the invention are, for example, glycidyl ethers of polyhydric phenols obtained by the reaction of polyhydric phenols with an excess of chlorohydrin, such as, for example, epichlorohydrin (e.g. glycidyl ethers of 2,2-bis(2,3-epoxypropoxyphenol)propane. Further examples of glycidyl ether epoxides that can be used in connection with the present invention are described, for example, in U.S. Pat. No. 3,018,262 and in "Handbook of Epoxy Resins" by Lee and Neville, McGraw-Hill Book Co., New York (1967).

There is also a large number of commercially available glycidyl ether epoxides that are suitable as component (a1), such as, for example, glycidyl methacrylate, diglycidyl ethers of bisphenol A, for example those obtainable under the trade names EPON 828, EPON 825, EPON 1004 and EPON 1010 (Shell); DER-331, DER-332 and DER-334 (Dow Chemical); 1,4-butanediol diglycidyl ethers of phenolformaldehyde novolak, e.g. DEN-431, DEN-438 (Dow Chemical); and resorcinol diglycidyl ethers; alkyl glycidyl ethers, such as, for example, $C_8$-$C_{10}$glycidyl ethers, e.g. HELOXY Modifier 7, $C_{12}$-$C_{14}$glycidyl ethers, e.g. HELOXY Modifier 8, butyl glycidyl ethers, e.g. HELOXY Modifier 61, cresyl glycidyl ethers, e.g. HELOXY Modifier 62, p-tert-butylphenyl glycidyl ethers, e.g. HELOXY Modifier 65, polyfunctional glycidyl ethers, such as diglycidyl ethers of 1,4-butanediol, e.g. HELOXY Modifier 67, diglycidyl ethers of neopentyl glycol, e.g. HELOXY Modifier 68, diglycidyl ethers of cyclohexanedimethanol, e.g. HELOXY Modifier 107, trimethylolethane triglycidyl ethers, e.g. HELOXY Modifier 44, trimethylolpropane triglycidyl ethers, e.g. HELOXY Modifier 48, polyglycidyl ethers of aliphatic polyols, e.g. HELOXY Modifier 84 (all HELOXY glycidyl ethers are obtainable from Shell).

Also suitable are glycidyl ethers that comprise copolymers of acrylic esters, such as, for example, styrene-glycidyl methacrylate or methyl methacrylate-glycidyl acrylate. Examples thereof include 1:1 styrene/glycidyl methacrylate, 1:1 methyl methacrylate/glycidyl acrylate, 62.5:24:13.5 methyl methacrylate/ethyl acrylate/glycidyl methacrylate.

The polymers of the glycidyl ether compounds can, for example, also comprise other functionalities provided that these do not impair the cationic curing.

Other glycidyl ether compounds suitable as component (a1) that are commercially available are polyfunctional liquid and solid novolak glycidyl ether resins, e.g. PY 307, EPN 1179, EPN 1180, EPN 1182 and ECN 9699.

It will be understood that mixtures of different glycidyl ether compounds may also be used as component (a1).

The glycidyl ethers (a1) are, for example, compounds of formula XX

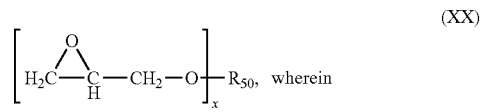

x is a number from 1 to 6; and $R_{50}$ is a mono- to hexavalent alkyl or aryl radical.

Preference is given, for example, to glycidyl ether compounds of formula XX, wherein x is the number 1, 2 or 3; and $R_{50}$ when x=1, is unsubstituted or $C_1$-$C_{12}$alkyl-substituted phenyl, naphthyl, anthracyl, biphenylyl, $C_1$-$C_{20}$alkyl, or $C_2$-$C_{20}$alkyl interrupted by one or more oxygen atoms, or $R_{50}$ when x=2, is 1,3-phenylene, 1,4-phenylene, $C_6$-$C_{10}$cycloalkylene, unsubstituted or halo-substituted $C_1$-$C_{40}$alkylene, $C_2$-$C_{40}$alkylene interrupted by one or more oxygen atoms, or a group

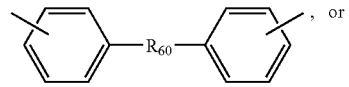

$R_{50}$ when x=3, is a radical

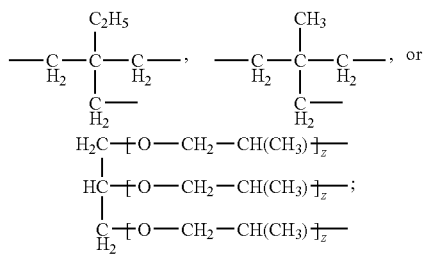

z is a number from 1 to 10; and
$R_{60}$ is $C_1$-$C_{20}$alkylene, oxygen or

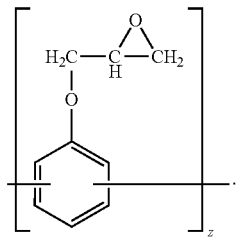

The glycidyl ethers (a1) are, for example, compounds of formula XXa

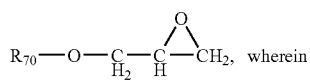

(XXa)

$R_{70}$ is unsubstituted or $C_1$-$C_{12}$alkyl-substituted phenyl; naphthyl; anthracyl; biphenylyl; $C_1$-$C_{20}$alkyl, $C_2$-$C_{20}$alkyl interrupted by one or more oxygen atoms; or a group of formula

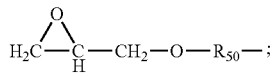

$R_{50}$ is phenylene, $C_1$-$C_{20}$alkylene, $C_2$-$C_{20}$alkylene interrupted by one or more oxygen atoms, or a group

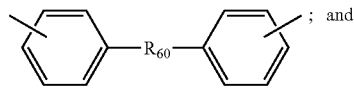

$R_{60}$ is $C_1$-$C_{20}$alkylene or oxygen.
Preference is given to the glycidyl ether compounds of formula XXb

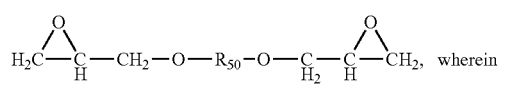

(XXb)

$R_{50}$ is phenylene, $C_1$-$C_{20}$alkylene, $C_2$-$C_{20}$alkylene interrupted by one or more oxygen atoms,
or a group

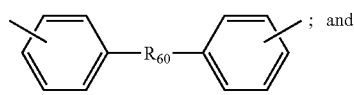

$R_{60}$ is $C_1$-$C_{20}$alkylene or oxygen.
Further examples for component (a1) are polyglycidyl ethers and poly(β-methylglycidyl)ethers obtainable by the reaction of a compound containing at least two free alcoholic and/or phenolic hydroxy groups per molecule with the appropriate epichlorohydrin under alkaline conditions, or alternatively in the presence of an acid catalyst with subsequent alkali treatment. Mixtures of different polyols may also be used.

Such ethers can be prepared with poly(epichlorohydrin) from acyclic alcohols, such as ethylene glycol, diethylene glycol and higher poly(oxyethylene)glycols, propane-1,2-diol and poly(oxypropylene)glycols, propane-1,3-diol, butane-1,4-diol, poly(oxytetramethylene)glycols, pentane-1,5-diol, hexane-1,6-diol, hexane-2,4,6-triol, glycerol, 1,1,1-trimethylol-propane, pentaerythritol and sorbitol, from cycloaliphatic alcohols, such as resorcitol, quinitol, bis(4-hydroxycyclohexyl)methane, 2,2-bis(4-hydroxycyclohexyl)propane and 1,1-bis-(hydroxymethyl)cyclohex-3-ene, and from alcohols having aromatic nuclei, such as N,N-bis(2-hydroxyethyl)aniline and p,p'-bis(2-hydroxyethylamino)diphenylmethane. They can also be prepared from mononuclear phenols, such as resorcinol and hydroquinone, and polynuclear phenols, such as bis(4-hydroxyphenyl)methane, 4,4-dihydroxydiphenyl, bis(4-hydroxyphenyl)sulfone, 1,1,2,2-tetrakis(4-hydroxyphenyl)ethane, 2,2-bis(4-hydroxyphenyl)-propane (bisphenol A) and 2,2-bis(3,5-dibromo-4-hydroxyphenyl)propane.

Further hydroxy compounds suitable for the preparation of polyglycidyl ethers and poly(β-methylglycidyl)ethers are the novolaks obtainable by the condensation of aldehydes, such as formaldehyde, acetaldehyde, chloral and furfural, with phenols, such as, for example, phenol, o-cresol, m-cresol, p-cresol, 3,5-dimethylphenol, 4-chlorophenol and 4-tert-butylphenol.

Poly(N-glycidyl) compounds can be obtained, for example, by dehydrochlorination of the reaction products of epichlorohydrin with amines containing at least two amino-hydrogen atoms, such as aniline, n-butylamine, bis(4-aminophenyl)methane, bis(4-aminophenyl)-propane, bis(4-methylaminophenyl)methane and bis(4-aminophenyl)ether, sulfone and sulfoxide. Further suitable poly(N-glycidyl) compounds include triglycidyl isocyanurate, and N,N'-diglycidyl derivatives of cyclic alkyleneureas, such as ethyleneurea and 1,3-propyleneurea, and hydantoins, such as, for example, 5,5-dimethylhydantoin.

Poly(S-glycidyl) compounds are also suitable. Examples thereof include the di-S-glycidyl derivatives of dithiols, such as ethane-1,2-dithiol and bis(4-mercaptomethylphenyl)ether.

There also come into consideration as component (a1) epoxy resins in which the glycidyl groups or β-methyl glycidyl groups are bonded to hetero atoms of different types, for example the N,N,O-triglycidyl derivative of 4-aminophenol, the glycidyl ether/glycidyl ester of salicylic acid or p-hydroxybenzoic acid, N-glycidyl-N'-(2-glycidyloxypropyl)-5,5-dimethylhydantoin and 2-glycidyloxy-1,3-bis(5,5-dimethyl-1-glycidylhydantoin-3-yl)propane.

Preference is given to diglycidyl ethers of bisphenols. Examples thereof include diglycidyl ethers of bisphenol A, e.g. ARALDIT® GY 250, diglycidyl ethers of bisphenol F and diglycidyl ethers of bisphenol S. Special preference is given to diglycidyl ethers of bisphenol A.

Further glycidyl compounds of technical importance are the glycidyl esters of carboxylic acids, especially di- and poly-carboxylic acids. Examples thereof are the glycidyl esters of succinic acid, adipic acid, azelaic acid, sebacic acid, phthalic acid, terephthalic acid, tetra- and hexa-hydrophthalic acid, isophthalic acid or trimellitic acid, or of dimerised fatty acids.

Examples of polyepoxides that are not glycidyl compounds are the epoxides of vinylcyclohexane and dicyclopentadiene, 3-(3',4'-epoxycyclohexyl)-8,9-epoxy-2,4-dioxaspiro-[5.5]undecane, the 3',4'-epoxycyclohexylmethyl esters of 3,4-epoxycyclohexanecarboxylic acid, (3,4-epoxycyclohexyl-methyl 3,4-epoxycyclohexanecarboxylate), butadiene diepoxide or isoprene diepoxide, epoxidised linoleic acid derivatives or epoxidised polybutadiene.

Further suitable epoxy compounds are, for example, limonene monoxide, epoxidised soybean oil, bisphenol-A and bisphenol-F epoxy resins, such as, for example, ARALDIT® GY 250 (A), ARALDIT® GY 282 (F), ARADILT® GY 285 (F)), and photocurable siloxanes that contain epoxy groups.

Further suitable cationically polymerisable or crosslinkable components (a1) can be found, for example, also in U.S. Pat. No. 3,117,099, U.S. Pat. No. 4,299,938 and U.S. Pat. No. 4,339,567.

From the group of aliphatic epoxides there are suitable especially the monofunctional symbol α-olefin epoxides having an unbranched chain consisting of 10, 12, 14 or 16 carbon atoms.

Because nowadays a large number of different epoxy compounds are commercially available, the properties of the binder can vary widely. One possible variation, for example depending upon the intended use of the composition, is the use of mixtures of different epoxy compounds and the addition of flexibilisers and reactive diluents.

The epoxy resins can be diluted with a solvent to facilitate application, for example when application is effected by spraying, but the epoxy compound is preferably used in the solventless state. Resins that are viscous to solid at room temperature can be applied hot.

Also suitable as component (a1) are all customary vinyl ethers, such as aromatic, aliphatic or cycloaliphatic vinyl ethers and also silicon-containing vinyl ethers. These are compounds having at least one, preferably at least two, vinyl ether groups in the molecule. Examples of vinyl ethers suitable for use in the compositions according to the invention include triethylene glycol divinyl ether, 1,4-cyclohexanedimethanol divinyl ether, 4-hydroxybutyl vinyl ether, the propenyl ether of propylene carbonate, dodecyl vinyl ether, tert-butyl vinyl ether, tert-amyl vinyl ether, cyclohexyl vinyl ether, 2-ethylhexyl vinyl ether, ethylene glycol monovinyl ether, butanediol monovinyl ether, hexanediol monovinyl ether, 1,4-cyclohexanedimethanol monovinyl ether, diethylene glycol monovinyl ether, ethylene glycol divinyl ether, ethylene glycol butylvinyl ether, butane-1,4-diol divinyl ether, hexanediol divinyl ether, diethylene glycol divinyl ether, triethylene glycol divinyl ether, triethylene glycol methylvinyl ether, tetra-ethylene glycol divinyl ether, pluriol-E-200 divinyl ether, polytetrahydrofuran divinyl ether-290, trimethylolpropane trivinyl ether, dipropylene glycol divinyl ether, octadecyl vinyl ether, (4-cyclohexylmethyleneoxyethene)-glutaric acid methyl ester and (4-butoxyethene)-isophthalic acid ester.

Examples of hydroxy-containing compounds include polyester polyols, such as, for example, polycaprolactones or polyester adipate polyols, glycols and polyether polyols, castor oil, hydroxy-functional vinyl and acrylic resins, cellulose esters, such as cellulose acetate butyrate, and phenoxy resins.

Further cationically curable formulations can be found, for example, in EP 119425.

As component (a1), preference is given to cycloaliphatic epoxides, or epoxides based on bisphenol A.

Accordingly, the invention relates also to a radiation-sensitive composition wherein component (a1) is at least one compound selected from the group of cycloaliphatic epoxy compounds, glycidyl ethers, oxetane compounds, vinyl ethers, acid-crosslinkable melamine resins, acid-crosslinkable hydroxymethylene compounds and acid-crosslinkable alkoxymethylene compounds.

If desired, the composition according to the invention can also contain free-radically polymerisable components, such as ethylenically unsaturated monomers, oligomers or polymers. These radically polymerizable components may be added to either component (a1) or component (a2). Said radically curable components may, however, also be part of (a1) or (a2), see description of (A1), (A2) and (A3), components comprising both, radically crosslinking and cationically crosslinking groups, further below. Suitable materials contain at least one ethylenically unsaturated double bond and are capable of undergoing addition polymerisation.

Examples of suitable monomers that contain an ethylenic double bond include alkyl and hydroxyalkyl acrylates and methacrylates, such as methyl, ethyl, propyl, isopropyl, butyl, hexyl, 2-ethylhexyl and 2-hydroxyethyl(meth)acrylate, stearyl acrylate and isobornyl acrylates. Further suitable examples include acrylonitrile, acrylamide, methacrylamide, N-substituted (meth)acrylamides, vinyl esters, such as vinyl acetate, vinyl ethers, such as isobutylvinyl ether, styrene, alkyl- and halo-substituted styrene, N-vinylpyrrolidone, vinyl chloride and ylnylidene chloride.

Examples of suitable monomers that contain at least two double bonds include glycerol diacrylates, glycerol triacrylates, ethylene glycol diacrylates, diethylene glycol diacrylates, diethylene glycol dimethacrylate, triethylene glycol dimethacrylates, 1,3-propanediol diacrylate, 1,3-propanediol dimethacrylate, neopentyl glycol diacrylates, hexamethylene glycol diacrylate, bisphenol-A diacrylates, 4,4'-bis(2-acryloyloxyethoxy)diphenylpropane, pentaerythritol triacrylate or tetraacrylate, pentaerythritol tetramethacrylate, trimethylolpropane triacrylate, 1,2,4-butanetriol trimethacrylate, 1,4-cyclohexanediol diacrylate, sorbitol hexaacrylate, bis[1-(2-acryloxy)]-p-ethoxyphenyldimethylmethane, bis[1-(3-acryloxy-2-hydroxy)]-ppropoxyphenyldimethylmethane and trishydroxyethyl isocyanurate trimethacrylate; the bisacrylates and bis-methacrylates of poly(ethylene glycol) having a molecular weight of from 200 to 500, diallyl phthalate, divinyl succinate, divinyl adipate and divinyl phthalate, vinyl acrylate, divinyl benzene, triallyl phosphate, triallyl isocyanurates and tris(2-acryloyl-ethyl) isocyanurate.

Examples of higher-molecular-weight (oligomeric) poly-unsaturated compounds include acrylated epoxy resins, acrylated or vinyl ether- or epoxy-group-containing polyesters, polyurethanes and polyethers. Further examples of unsaturated oligomers are unsaturated polyester resins, which are usually prepared from maleic acid, phthalic acid and one or more diols and have molecular weights of approximately from 500 to 3000. Vinyl ether monomers and oligomers, and maleate-terminated oligomers having polyester, poly-urethane, polyether, polyvinyl ether and epoxy main chains can also be used. Also copolymers of vinyl ethers and monomers which are functionalised with maleic acid, as described in WO 90/01512, are also very suitable. Also suitable, however, are copolymers of monomers functionalised with vinyl ether and maleic acid. Such unsaturated oligomers can also be referred to as pre-polymers. Functionalised acrylates are also suitable. Examples of suitable monomers that are normally used to form the base polymer (the backbone) of the functionalised acrylate or methacrylate polymer are acrylate, methacrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate, etc. In addition, suitable amounts of functional monomers are copolymerised during the polymerisation in order to obtain the functional polymers. Acid-functionalised acrylate or methacrylate polymers are obtained using acid-functional monomers, such as acrylic acid and methacrylic acid. Hydroxy-functional acrylate or methacrylate polymers are obtained from hydroxy-functional monomers, such as 2-hydroxyethyl methacrylate, 2-hydroxypropyl methacrylate and 3,4-dihydroxybutyl meth-acrylate. Epoxy-functionalised acrylate or methacrylate polymers are obtained using epoxy-functional monomers, such as glycidyl methacrylate, 2,3-epoxybutyl methacrylate, 3,4-epoxybutyl methacrylate, 2,3-epoxycyclohexyl methacrylate, 10,11-epoxyundecyl meth-acrylate, etc. It is also possible to obtain isocyanate-functional polymers from isocyanate-functionalised monomers, such as meta-isopropenyl-α,α-dimethylbenzyl isocyanate.

Especially suitable are, for example, esters of ethylenically unsaturated mono- or polyfunctional carboxylic acids and polyols or polyepoxides, and polymers having ethylenically unsaturated groups in the chain or in side groups, such as unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and mixtures of one or more such polymers.

Examples of suitable mono- or poly-functional unsaturated carboxylic acids are acrylic acid, methacrylic acid, crotonic acid, itaconic acid, cinnamic acid, maleic acid and fumaric acid and unsaturated fatty acids, such as linolenic acid or oleic acid. Preference is given to acrylic acid and methacrylic acid.

Mixtures of saturated di- or poly-carboxylic acids with unsaturated carboxylic acids may, however, also be used. Examples of suitable saturated di- or poly-carboxylic acids include, for example, tetrachlorophthalic acid, tetrabromophthalic acid, phthalic acid anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid, etc.

Suitable polyols are aromatic and especially aliphatic and cycloaliphatic polyols. Examples of aromatic polyols are hydroquinone, 4,4'-dihydroxydiphenyl, 2,2-di(4-hydroxyphenyl)-propane, and novolaks and resoles. Examples of polyepoxides are those based on the polyols mentioned, especially the aromatic polyols and epichlorohydrin. Also suitable as polyols are polymers and copolymers containing hydroxyl groups in the polymer chain or in side groups, such as polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols are alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to have been modified, for example etherified, or esterified by other carboxylic acids.

Examples of esters are:
trimethylol propane triacrylate, trimethylolethane triacrylate, trimethylol propane trimethacrylate, trimethylolethane trimethacrylate, tetramethylene glycol dimethacrylate, triethylene glycol dimethacrylate, tetraethylene glycol diacrylate, pentaerythritol diacrylate, penta-erythritol triacrylate, pentaerythritol tetraacrylate, dipentaerythritol diacrylate, dipenta-erythritol triacrylate, dipentaerythritol tetraacrylate, dipentaerythritol pentaacrylate, dipenta-erythritol hexaacrylate, tripentaerythritol octaacrylate, pentaerythritol dimethacrylate, penta-erythritol trimethacrylate, dipentaerythritol dimethacrylate, dipentaerythritol tetrameth-acrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

Suitable unsaturated, free-radically polymerisable compounds are also the amides of the same or different unsaturated carboxylic acids and aromatic, cycloaliphatic and aliphatic polyamines having preferably from 2 to 6, especially from 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecyl-enediamine, 1,4-diaminocyclohexane, isophoronediamine, phenylenediamine, bisphenylenediamine, di-β-aminoethyl ether, diethylenetriamine, triethylenetetraamine and di(β-aminoethoxy)- or di(β-aminopropoxy)-ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, bis(methacrylamidopropoxy)ethane, β-methacrylamidoethyl methacrylate and N-[(β-hydroxyethoxy)ethyl]-acrylamide.

Suitable unsaturated polyesters and polyamides are derived, for example, from maleic acid and diols or diamines. The maleic acid may have been partially replaced by other dicarboxylic acids. They can be used together with ethylenically unsaturated comonomers, for example styrene. The polyesters and polyamides can also be derived from dicarboxylic acids and ethylenically unsaturated diols or diamines, especially from those having longer chains of, for example, from 6 to 20 carbon atoms. Examples of polyurethanes are those composed of saturated or unsaturated diisocyanates and saturated or unsaturated diols.

Polybutadiene and polyisoprene and copolymers thereof are known. Suitable comonomers include, for example, olefins, such as ethylene, propene, butene, hexene, (meth)acrylates, acrylonitrile, styrene and vinyl chloride. Polymers having (meth)acrylate groups in the side chain are also known. They may be, for example, reaction products of novolak-based epoxy resins with (meth)acrylic acid; homo- or co-polymers of vinyl alcohol or hydroxyalkyl derivatives thereof that have been esterified with (meth)acrylic acid; or homo- and co-polymers of (meth)acrylates that have been esterified with hydroxyalkyl(meth)acrylates.

It is also possible to use compounds that can be crosslinked equally both free-radically and cationically. Such compounds contain, for example, both a vinyl group and a cycloaliphatic epoxy group. Examples thereof are described in JP 2-289611-A and U.S. Pat. No. 6,048,953.

Mixtures of two or more such free-radically polymerisable materials can also be used.

Binders may also be added to the compositions according to the invention, this being especially advantageous when the photopolymerisable compounds are liquid or viscous substances. The amount of binder may be, for example, from 5 to 95% by weight, preferably from 10 to 90% by weight and especially from 40 to 90% by weight, based on total solids. The binder will be selected according to the field of use and the properties required therefor, such as developability in aqueous and organic solvent systems, adhesion to substrates and sensitivity to oxygen.

Suitable binders are, for example, polymers having a molecular weight of approximately from 2000 to 2 000 000, preferably from 5000 to 1 000 000. Examples thereof are: homo- and copolymers of acrylates and methacrylates, for example copolymers of methyl methacrylate/ethyl acrylate/methacrylic acid, poly(methacrylic acid alkyl esters), poly(acrylic acid alkyl esters); phenolic resins, cellulose derivatives, such as cellulose esters and ethers, for example cellulose acetate, cellulose acetate butyrate, methyl cellulose, ethyl cellulose; polyvinyl butyral, polyvinylformal, polyolefins, cyclised rubber, polyethers, such as poly-ethylene oxide, polypropylene oxide, polytetrahydrofuran; polystyrene, polycarbonate, poly-urethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethyleneadipamide), polyesters such as poly(ethylene glycol terephthalate) and poly(hexamethylene glycol succinate); and polyamides.

The resins mentioned below under (C1) may also be used as free-radically curable component. Of particular interest are, for example, unsaturated acrylates having reactive functional groups. The reactive functional group may be selected, for example, from a hydroxyl, thiol, isocyanate, epoxy, anhydride, carboxyl, amino or blocked amino group. Examples of OH-group-containing unsaturated acrylates are hydroxyethyl and hydroxybutyl acrylates and also glycidyl acrylates.

The unsaturated compounds may also be used in admixture with non-photopolymerisable film-forming components. These may be, for example, polymers that can be dried physically or solutions thereof in organic solvents, such as nitrocellulose or cellulose acetobutyrate. They may alternatively be chemically or thermally curable resins, such as polyisocyanates, polyepoxides or melamine resins. Drying oils, such as linseed oil, linseed-oil-modified alkyd resins, tung oil and soybean oil, can also be present. The concomitant use of thermally curable resins is important for use in so-called hybrid systems which are photopolymerised in a first step and crosslinked by thermal aftertreatment in a second step.

Thus, the radiation-curable compositions of the present invention may also comprise:
(A1) compounds having one or more free-radically polymerisable double bonds that additionally contain at least one further functional group that is reactive in addition and/or condensation reactions (examples are given above),
(A2) compounds having one or more free-radically polymerisable double bonds that additionally contain at least one further functional group that is reactive in addition and/or condensation reactions, the additional functional group being complementary to or reactive towards the additional functional group of component (A1),
(A3) at least one monomeric, oligomeric and/or polymeric compound having at least one functional group that is reactive in addition and/or condensation reactions towards the functional groups of component (A1) or (A2) that are present in addition to the free-radically polymerisable double bonds.

Component (A2) in each case carries the groups complementary to or reactive towards component (A1). Different types of functional groups may also be present in a component. Component (A3) provides a component that contains further functional groups that are reactive in addition and/or condensation reactions and that are able to react with the functional groups of (A1) or (A2) that are present in addition to the free-radically polymerisable double bonds. Component (A3) contains no free-radically polymerisable double bonds.

Examples of such combinations (A1), (A2), (A3) can be found in WO 99/55785. Examples of suitable functional groups are hydroxyl, isocyanate, epoxy, anhydride, carboxyl and blocked amino groups. Examples have been described above.

Constituents of the thermally curable component (C) are, for example, thermally curable lacquer or coating system constituents customary in the art. Component (C) accordingly may consist of a large number of constituents.

Examples of component (C) include oligomers and/or polymers derived from α,β-unsaturated acids and derivatives thereof, for example polyacrylates and polymethacrylates, polymethyl methacrylates impact-resistant-modified with butyl acrylate, polyacrylamides and polyacrylonitriles. Further examples of component (C) are urethanes, polyurethanes derived on the one hand from polyethers, polyesters and polyacrylates having free hydroxyl groups and on the other hand from aliphatic or aromatic polyisocyanates, and educts thereof. Component (C) accordingly also includes, for example, crosslinkable acrylic resins derived from substituted acrylic acid esters, for example epoxy acrylates, urethane acrylates and polyester acrylates. Alkyd resins, polyester resins and acrylate resins and modifications thereof that are crosslinked with melamine resins, urea resins, isocyanates, isocyanurates, polyisocyanates, polyisocyanurates and epoxy resins, may also be a constituent of component (C). Component (C) is, for example, generally a film-forming binder based on a thermoplastic or thermocurable resin, especially on a thermocurable resin. Examples thereof are alkyd, acrylic, polyester, phenolic, melamine, epoxy and polyurethane resins and mixtures thereof. Examples thereof can be found, for example, in Ullmann's Encyclopedia of Industrial Chemistry, 5th Ed., Vol. A18, pp. 368-426, VCH, Weinheim 1991.

Component (C) may also be a cold-curable or hot-curable binder, in which case the addition of a curing catalyst may be advantageous. Suitable catalysts that accelerate the full cure of the binder can be found, for example, in Ullmann's Encyclopedia of Industrial Chemistry, Vol. A18, page 469, VCH Verlagsgesellschaft, Weinheim 1991.

Specific examples of binders suitable as component (C) are:
1. surface-coatings based on cold- or hot-crosslinkable alkyd, acrylate, polyester, epoxy or melamine resins or mixtures of such resins, optionally with the addition of a curing catalyst;
2. two-component polyurethane surface-coatings based on hydroxyl-group-containing acrylate, polyester or polyether resins and aliphatic or aromatic isocyanates, isocyanurates or polyisocyanates;
3. one-component polyurethane surface-coatings based on blocked isocyanates, isocyanurates or polyisocyanates, which are de-blocked during heating; it is also possible to add melamine resins as appropriate;

4. one-component polyurethane surface-coatings based on aliphatic or aromatic urethanes or polyurethanes and hydroxyl-group-containing acrylate, polyester or polyether resins;
5. one-component polyurethane surface-coatings based on aliphatic or aromatic urethane acrylates or polyurethane acrylates having free amine groups in the urethane structure and melamine resins or polyether resins, optionally with the addition of a curing catalyst;
6. two-component surface-coatings based on (poly)ketimines and aliphatic or aromatic isocyanates, isocyanurates or polyisocyanates;
7. two-component surface-coatings based on (poly)ketimines and an unsaturated acrylate resin or a polyacetoacetate resin or a methacrylamidoglycolate methyl ester;
8. two-component surface-coatings based on carboxyl- or amino-group-containing polyacrylates and polyepoxides;
9. two-component surface-coatings based on anhydride-group-containing acrylate resins and a polyhydroxy or polyamino component;
10. two-component surface-coatings based on acrylate-containing anhydrides and polyepoxides;
11. two-component surface-coatings based on (poly)oxazolines and anhydride-group-containing acrylate resins or unsaturated acrylate resins or aliphatic or aromatic isocyanates, isocyanurates or polyisocyanates;
12. two-component surface-coatings based on unsaturated polyacrylates and polymalonates;
13. thermoplastic polyacrylate surface-coatings based on thermoplastic acrylate resins or extrinsically crosslinking acrylate resins in combination with etherified melamine resins;
14. surface-coating systems based on urethane (meth)acrylate having (meth)acryloyl groups and free isocyanate groups and on one or more compounds that react with iso-cyanates, for example free or esterified polyols. Such systems have been published, for example, in EP 928800.

(and melamine derivatives), 2-component polyurethane, 1-component polyurethane, 2-component epoxy/carboxy or 1-component epoxy/carboxy. Mixtures of such systems are also possible, for example the addition of melamine (or derivatives thereof) to 1-component polyurethanes.

Component (C) is preferably a binder based on a polyacrylate with melamine or on a melamine derivative or a system based on a polyacrylate and/or polyester polyol with an unblocked polyisocyanate or polyisocyanurate.

Component (C) may also comprise monomeric and/or oligomeric compounds having ethylenically unsaturated bonds (prepolymers) that additionally contain at least one or more OH, $NH_2$, COOH, epoxy or NCO group(s) (=C1) that are capable of reaction with the binder and/or the crosslinking agent constituent of component (C). After application and thermal curing, the ethylenically unsaturated bonds are converted to a crosslinked, high molecular weight form by irradiation with UV light. Examples of such components (C) are described, for example, in the above-mentioned publication, Ullmann's Encyclopedia of Industrial Chemistry, 5th Ed., Vol. A18, pages 451-453, or by S. Urano, K. Aoki, N. Tsuboniva and R. Mizuguchi in Progress in Organic Coatings, 20 (1992), 471-486, or by H. Terashima and O. Isozaki in JOCCA 1992 (6), 222.

(C1) may, for example, also be an OH-group-containing unsaturated acrylate, for example hydroxyethyl or hydroxybutyl acrylate or a glycidyl acrylate. Component (C1) may be of any desired structure (for example it may contain units of polyester, polyacrylate, polyether, etc.), provided that it contains an ethylenically unsaturated double bond and additionally free OH, COOH, $NH_2$, epoxy or NCO groups.

(C1) may, for example, also be obtained by reacting an epoxy-functional oligomer with acrylic acid or methacrylic acid. A typical example of an OH-functional oligomer having vinylic double bonds is

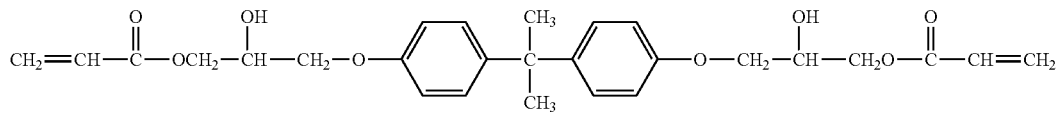

Blocked isocyanates that can also be used as component (C) are described, for example, in Organischer Metallschutz Entwicklung und Anwendung von Beschichtungsstoffen, pages 159-160, Vincentz Verlag, Hanover (1993). These are compounds in which the highly reactive NCO group is "blocked" by reaction with specific radicals, for example a primary alcohol, phenol, acetic acid ethyl ester, ∈-caprolactam, phthalimide, imidazole, oxime or amine. The blocked isocyanate is stable in liquid systems and also in the presence of hydroxy groups. Upon heating, the blocking group (protecting group) is removed again and the NCO group is freed.

1-Component (1C) and 2-component (2C) systems may be used as component (C). Examples of such systems are described in Ullmann's Encyclopedia of Industrial Chemistry, Vol. A18, Paints and Coatings, pages 404-407, VCH Verlagsgesellschaft mbH, Weinheim (1991). It is possible to optimise the composition by specific adaptation, for example by varying the binder/crosslinking agent ratios. Such measures will be known to the person skilled in the art and are customary in coating technology.

In the curing process according to the invention, component (C) is preferably a mixture based on acrylate/melamine obtained by reaction of $CH_2$=CHCOOH with

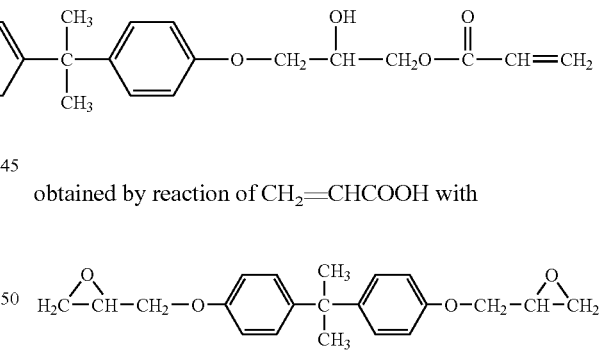

Another possible method of obtaining component (C1) is, for example, the reaction of an oligomer that contains only one epoxy group and has a free OH group at another position in the molecule.

The quantity ratio of the free-radically radiation-curable-polymerisable components to the thermally polymerisable component (C) in the UV- and thermally-crosslinkable formulations is not critical. "Dual-cure" systems are known to the person skilled in the art, who will therefore be familiar with the optimum mixing ratios of the free-radically- and thermally-crosslinkable components according to the intended use. For example, the ratio can be in the range from 5:95 to 95:5, from 20:80 to 80:20 or from 30:70 to 70:30, for example from 40:60 to 60:40.

Examples of "dual-cure" systems, that is to say systems comprising both radiation-curable and thermally curable components, can be found inter alia in U.S. Pat. No. 5,922,473, columns 6 to 10.

The formulations according to the invention can further comprise as component (a1) non-aqueous coating compositions based on an oxidatively drying alkyd resin which contains at least one, preferably two or more, functional group(s) capable of undergoing polymerisation or polycondensation reactions in the presence of an acid. Examples of such resins are vinyl-ether-functionalised alkyd resins, acetal-functionalised alkyd resins, and/or alkoxysilane-functionalised alkyd resins, as proposed, e.g., in WO 99/47617. Those modified alkyd resins may be used alone or in combination with other alkyd resins. At least some of the alkyd resin composition in the non-aqueous coating is oxidatively drying as a result of the incorporation of a large number of unsaturated, aliphatic compounds, at least some of which are polyunsaturated.

Formulations containing those modified alkyd resins as component (a1) may optionally contain, in addition to the photoinitiator (b), an oxidative dryer. Suitable oxidative dryers are, for example, metal siccatives. There may be mentioned as suitable siccatives, for example, the metal salts of (cyclo)aliphatic acids, such as octanoic acid and naphthenic acid, the metals to be used being, for example, cobalt, manganese, lead, zirconium, calcium, zinc and rare earth metals. Mixtures of siccatives may be used. Preference is given to metal salts of cobalt, zirconium and calcium, or mixtures thereof. The siccatives (calculated as metal) are usually used in an amount of from 0.001 to 3% by weight.

Under certain conditions it may also be advantageous, when using the modified alkyd resins as component (a1), to use one or more mono- or bis-acylphosphine oxide photoinitiators in addition to the sulfonium salt of formula (I). Suitable monoacyl- or bisacyl-phosphine oxide photoinitiators include, for example, monoacylphosphine oxides such as (2,4,6-trimethylbenzoyl)-diphenylphosphine oxide (DAROCUR® TPO) or (2,4,6-trimethylbenzoylphenyl-ethoxy-phosphine oxide, or bisacylphosphine oxide photoinitiators such as bis(2,6-dimethoxybenzoyl)-2,4,4-trimethylpentyl-phosphine oxide, bis(2,4,6-trimethylbenzoyl)-(2,4-dipentyloxyphenyl)-phosphine oxide and bis(2,4,6-trimethylbenzoyl)phenyl-phosphine oxide (IRGACURE® 819). Those monoacyl- or bisacyl-phosphine oxides are advantageously used in an amount of from 0.5 to 5%.

When component (a1) contains modified alkyd resins, in addition to the photoinitiator (b) it is also possible to use an oxidative dryer and suitable monoacyl- or bisacyl-phosphine oxide photoinitiators.

The alkyd resins used as component (a1) contain a large number of unsaturated, aliphatic compounds, at least some of which are polyunsaturated. The unsaturated aliphatic compounds preferably used for the preparation of those alkyd resins are unsaturated aliphatic monocarboxylic acids, especially polyunsaturated aliphatic monocarboxylic acids.

Examples of mono-unsaturated fatty acids are myristoleic acid, palmitic acid, oleic acid, gadoleic acid, erucic acid and ricinoleic acid. Preferably fatty acids containing conjugated double bonds, such as dehydrogenated castor oil fatty acid and/or tung oil fatty acid, are used. Other suitable monocarboxylic acids include tetrahydrobenzoic acid and hydrogenated or non-hydrogenated abietic acid or the isomers thereof. If desired, the monocarboxylic acid in question may be used wholly or in part in the form of a triglyceride, e.g. as vegetable oil, in the preparation of the alkyd resin. If desired, mixtures of two or more such mono-carboxylic acids or triglycerides may be used, optionally in the presence of one or more saturated, (cyclo)aliphatic or aromatic monocarboxylic acids, e.g. pivalic acid, 2-ethyl-hexanoic acid, lauric acid, palmitic acid, stearic acid, 4-tert-butyl-benzoic acid, cyclopentanecarboxylic acid, naphthenic acid, cyclohexanecarboxylic acid, 2,4-dimethylbenzoic acid, 2-methylbenzoic acid and benzoic acid.

If desired, polycarboxylic acids may also be incorporated into the alkyd resin, such as phthalic acid, isophthalic acid, terephthalic acid, 5-tert-butylisophthalic acid, trimellitic acid, pyromellitic acid, succinic acid, adipic acid, 2,2,4-trimethyladipic acid, azelaic acid, sebacic acid, dimerised fatty acids, cyclopentane-1,2-dicarboxylic acid, cyclohexane-1,2-dicarboxylic acid, 4-methylcyclohexane-1,2-dicarboxylic acid, tetrahydrophthalic acid, endomethylenecyclohexane-1,2-dicarboxylic acid, butane-1,2,3,4-tetracarboxylic acid, endoisopropylidenecyclohexane-1,2-dicarboxylic acid, cyclohexane-1,2,4,5-tetracarboxylic acid and butane-1,2,3,4-tetracarboxylic acid. If desired, the carboxylic acid in question may be used as an anhydride or in the form of an ester, for example an ester of an alcohol having from 1 to 4 carbon atoms.

In addition, the alkyd resin can be composed of di- or poly-valent hydroxyl compounds. Examples of suitable divalent hydroxyl compounds are ethylene glycol, 1,3-propanediol, 1,6-hexanediol, 1,12-dodecanediol, 3-methyl-1,5-pentanediol, 2,2,4-trimethyl-1,6-hexane-diol, 2,2-dimethyl-1,3-propanediol and 2-methyl-2-cyclohexyl-1,3-propanediol. Examples of suitable triols are glycerol, trimethylolethane and trimethylolpropane. Suitable polyols having more than 3 hydroxyl groups are pentaerythritol, sorbitol and etherified products of the compounds in question, such as ditrimethylolpropane and di-, tri- and tetra-pentaerythritol. Preferably, compounds having from 3 to 12 carbon atoms, e.g. glycerol, pentaerythritol and/or dipentaerythritol, are used.

The alkyd resins can be obtained by direct esterification of the constituents, with the option that some of those components may already have been converted into ester diols or polyester diols. The unsaturated fatty acids can also be used in the form of a drying oil, such as linseed oil, tuna fish oil, dehydrogenated castor oil, coconut oil and dehydrogenated coconut oil. The final alkyd resin is then obtained by transesterification with the other acids and diols added. The transesterification is advantageously carried out at a temperature in the range of from 115 to 250° C., optionally in the presence of solvents such as toluene and/or xylene. The reaction is advantageously carried out in the presence of a catalytic amount of a transesterification catalyst. Examples of suitable transesterification catalysts include acids, such as ptoluenesulfonic acid, basic compounds, such as an amine, or compounds such as calcium oxide, zinc oxide, tetraisopropyl orthotitanate, dibutyltin oxide and tri-phenylbenzylphosphonium chloride.

The vinyl ether, acetal and/or alkoxysilane compounds used as part of component (a1) preferably contain at least two vinyl ether, acetal and/or alkoxysilane groups and have a molecular weight of 150 or more. Those vinyl ether, acetal and/or alkoxysilane compounds can be obtained, for example, by the reaction of a commercially available vinyl ether, acetal and/or alkoxysilane compound containing a vinyl ether, acetal and/or alkoxysilane group and in addition a maximum of one functional amino, epoxy, thiol, isocyanate, acrylic, hydride or hydroxyl group, with a compound having at least two groups capable of reacting with an amino, epoxy, thiol, isocyanate, acrylic, hydride or hydroxyl group. As examples thereof there may be mentioned compounds having at least two epoxy, isocyanate, hydroxyl and/or ester groups or compounds having at least two ethylenically or ethynylenically unsaturated groups.

As component (a1), preference is given to a composition in which the vinyl ether, acetal and/or alkoxysilane compounds are covalently bonded to the alkyd resin by addition via a reactive group such as an amino, hydroxyl, thiol, hydride, epoxy and/or isocyanate group. For that purpose, the compounds must have at least one group capable of forming an adduct with the reactive groups present in the alkyd resin.

To incorporate vinyl ether groups into the alkyd resin, use is made of a vinyloxyalkyl compound, the alkyl group of which is substituted by a reactive group, such as a hydroxyl, amino, epoxy or isocyanate group, that is capable of forming an adduct with one or more of the reactive groups present in the alkyd resin.

As component (a1), preference is given to compositions in which the ratio of the number of oxidatively drying groups present in the alkyd resin to the number of groups that are reactive in the presence of an acid is in the range of from 1/10 to 15/1, especially from 1/3 to 5/1. Instead of a single modified alkyd resin, it is also possible to use a plurality of alkyd resins, with one alkyd resin being highly modified and the others being less modified or not modified at all.

Examples of vinyl ether compounds capable of being covalently bonded to the alkyd resin are ethylene glycol monovinyl ether, butanediol monovinyl ether, hexanediol monovinyl ether, triethylene glycol monovinyl ether, cyclohexanedimethanol monovinyl ether, 2-ethyl-hexanediol monovinyl ether, polytetrahydrofuran monovinyl ether, tetraethylene glycol monovinyl ether, trimethylolpropane divinyl ether and aminopropyl vinyl ether.

Adducts can be formed, for example, by reacting the vinyl ether compounds containing a hydroxyl group or amino group with an excess of a diisocyanate, followed by the reaction of that free-isocyanate-group-containing adduct with the free hydroxyl groups of the alkyd resin. Preferably, a process is used in which first the free hydroxyl groups of the alkyd resin react with an excess of a polyisocyanate, and then the free isocyanate groups react with an amino-group- or hydroxyl-group-containing vinyl ether compound. Instead of a diisocyanate, it is also possible to use a diester. Transesterification of the hydroxyl groups present in the alkyd resin with an excess of the diester, followed by transesterification or transamidation of the remaining ester groups with hydroxy-functional vinyl ether compounds or amino-functional vinyl ether compounds, respectively, yields vinyl-ether-functional alkyd resins. It is also possible to incorporate (meth)acrylate groups into the alkyd resin during preparation of the alkyd resin, by carrying out the preparation in the presence of a hydroxy-functional (meth)acrylate ester, such as hydroxyethyl methacrylate (HEMA), and then reacting the thus functionalised alkyd resin by means of a Michael reaction with a vinyl-ether-group-containing compound and a primary-amino-group-containing compound, followed by reaction with e.g. an isocyanate compound, in order to obtain a non-basic nitrogen atom.

An example of such a reaction is described, for example, in WO 99/47617. Esterification of ricinine fatty acid with dipentaerythritol, followed by transesterification of the free hydroxyl groups with diethyl malonate and 4-hydroxybutyl vinyl ether in a suitable ratio, yields a vinylether-functional alkyd resin suitable for use as component (a1).

For the preparation of acetal-functional alkyd resins, use is generally made of dialkyl acetal functionalised with an amino group. Examples of suitable acetal compounds include 4-aminobutyraldehyde dimethyl acetal and 4-aminobutyraldehyde diethyl acetal. The alkyd resin is modified by the addition of the aminoacetal monomer to an alkyd resin functionalised with isocyanate groups, with ester groups of a low-boiling alcohol or with (meth)acrylate groups. The resulting dialkyl-acetal-modified alkyd resin can be incorporated into the coating composition having a high solids content and low viscosity. The preparation of acetal-functional alkyd resins can also be carried out by reacting hydroxyacetal with the carboxyl groups of the alkyd resin or by reacting a diisocyanate or diester compound with the hydroxyl groups of the alkyd resin.

An example of this preparative method is described in WO 99/47617, for example the esterification of a hydroxy-functional alkyd resin with diethyl malonate, followed by transamidation of the free ester group with 4-aminobutyraldehyde dimethyl acetal in a suitable ratio. The resulting acetal-modified alkyd resin is suitable as component (a1).

For the incorporation of alkoxysilane groups into the alkyd resin, use is made of a siloxane compound having one or more reactive group(s) which are subsequently reacted with one or more of the constituents making up the alkyd resin. These are, for example, alkoxy-silanes of the formula: $(E)_a\text{-Si}(R_{10})_b(R_{20})_c$, wherein $R_{10}$ is alkoxy or oxyalkylenealkoxy or, when E is hydrogen, $R_{10}$ is halogen, $R_{20}$ is an aliphatic, cycloaliphatic or aromatic group, and E is hydrogen or an alkyl group substituted by an amino, isocyanate, mercapto or epoxy group; a is from 1 to 3, b is from 1 to 3, c is from 0 to 2, and a+b+c=4.

$R_{10}$ is preferably an alkoxy group having from 1 to 4 carbon atoms in the alkoxy group, and $R_{20}$ is preferably a group having not more than 18 carbon atoms.

Examples of suitable siloxane compounds are 3-aminopropyl-triethoxysilane, polyglycolether-modified aminosilane, 3-aminopropyl-trimethoxysilane, 3-aminopropyltris-methoxyethoxyethoxysilane, 3-aminopropyl-methyl-diethoxysilane, N-2-aminoethyl-3-aminopropyl-trimethoxy-silane, N2-aminoethyl-3-aminopropyl-methyldimethoxy-silane, N-methyl-3-aminopropyl-trimethoxysilane, 3-ureidopropyl-triethoxysilane, 3,4,5-dihydroimidazol-1-yl-propyltriethoxysilane, 3-methacryloxypropyl-trimethoxysilane, 3-glycidyloxypropyl-trimethoxysilane, 3-mercaptopropyl-trimethoxysilane and 3-mercaptopropyl-methyl-dimethoxysilane, triethoxysilane, diethoxymethylsilane, dimethoxymethylsilane, tri-methoxysilane, trichlorosilane, triiodosilane, tribromosilane, dichloromethylsilane and dibromomethylsilane.

The alkyd resin can be modified, for example, by the insertion of an amino-group-modified alkoxysilane into an alkyd resin modified with a polyisocyanate or a polyester of a low-boiling alcohol. Hydride-functional alkoxysilanes can be bonded directly to the alkyd, i.e. without modification with a binding molecule such as a diisocyanate or diester, by adding a compound containing a silylhydride group to an ethylenically unsaturated group in the alkyd resin. That addition is catalysed by a transition metal. In that process, use is preferably made of a halogenated silylhydride and, in order to terminate the addition reaction, conversion into an alkoxysilane compound with a low-boiling alcohol. The addition reaction is advantageously carried out in the absence of sterically hindering groups and proceeds in optimum manner when the ethylenically unsaturated groups are terminal groups, as is the case, for example, with esters of 10-undecenecarboxylic acid.

Examples of the preparation of alkoxysiloxane-modified alkyd resins are described in WO 99/47617. Esterification of a hydroxy-functional alkyd resin with diethyl malonate, followed by transamidation of the free ester group with 3-aminopropyltriethoxysilane in a suitable ratio yields an alkoxysilane-modified alkyd resin. Hydroxy-modified alkyd resin can also be reacted with an excess of isophorone diisocyanate, followed by reaction of the free isocyanate groups with 3-aminopropyltriethoxysilane. Both alkoxysiloxane-modified alkyd resins obtained by the processes described are suitable for use in component (a1).

When free-radically polymerisable components are added to the formulation according to the invention, it may be advantageous to add also a suitable free-radical photoinitiator or a mixture of such photoinitiators, e.g. benzophenone and derivatives thereof, ESACURE® TZT available from Lamberti, a mixture of 2,4,6-trimethylbenzophenone and 4-methylbenzophenone, DAROCUROBP, benzophenone, 4-methyl benzophenone, 2,4,6-trimethylbenzophenone, 3-methyl-4'-phenyl-benzophenone, 2,4,6-trimethyl-4'-phenyl-benzophenone, etc., acetophenone and derivatives thereof, e.g. 1-Hydroxy-cyclohexyl-phenyl-ketone (IRGACURE® 184) or IRGACURE® 8500 (a mixture of IRGACURE® 8184 with benzophenone); or 2-hydroxy-2-methyl-1-phenyl-propanone (DAROCUR® 1173), 2-Hydroxy-1-{4-[4-(2-hydroxy-2-methyl-propionyl)-benzyl]-phenyl}-2-methyl-propan-1-one (IRGACURE®127), 2-hydroxy-1-[3-[4-(2-hydroxy-2-methyl-propionyl)-phenyl]-1,1,3-trimethyl-indan-5-yl]-2-methyl-propan-1-one, 4-aroyl-1,3-dioxolane, α-hydroxy- or α-amino-acetophenone, such as, for example, 2-methyl-1 [4-(methylthio)phenyl]-2-morpholinopropan-1-one (IRGACURE® 8907), 2-benzyl-2-dimethylamino-1-(4-morpholinophenyl)-butanone-1 (IRGACURE® 8369), 2-dimethylamino-2-(4-methyl-benzyl)-1-(4-morpholin-4-yl-phenyl)-butan-1-one (IRGACURE® 8379), 1-[4-(2-hydroxyethoxy)-phenyl]-2-hydroxy-2-methyl-1-propan-1-one (IRGACURE® 82959), 2,2-dimethoxy-1,2-diphenylethan-1-one (IRGACURE® 8651), 2-hydroxy-1-{4-[4-(2-hydroxy-2-methyl-propionyl)-benzyl]-phenyl}-2-methyl-propan-1-one (IRGACURE127), 2-benzyl-1-(3,4-dimethoxy-phenyl)-2-dimethylamino-butan-1-one, 2-hydroxy-1-{4-[4-(2-hydroxy-2-methyl-propionyl)-phenoxy]-phenyl}-2-methyl-propan-1-one, ESACURE®KIP provided by Fratelli Lamberti, 2-hydroxy-1-{1-[4-(2-hydroxy-2-methyl-propionyl)-phenyl]-1,3,3-trimethylindan-5-yl}-2-methyl-propan-1-one; benzoin alkyl ethers and benzil ketal, such as, for example, benzil dimethyl ketal, phenyl glyoxalate and derivatives thereof, e.g. oxo-phenyl-acetic acid 2-[2-(2-oxo-2-phenyl-acetoxy)-ethoxy]-ethyl ester (IRGACURE®754), mono- or bisacylphosphine oxide, such as, for example, (2,4,6-trimethyl-benzoyl)-phenyl-phosphine oxide (DAROCUR®TPO), bis(2,6-dimethoxybenzoyl)-(2,4,4-trimethyl-pent-1-yl)phosphine oxide, bis(2,4,6-trimethylbenzoyl)-phenyl-phosphine oxide (IRGACURE®819) or bis(2,4,6-trimethyl benzoyl)-(2,4-dipentyloxyphenyl)phosphine oxide.

The DAROCUR and IRGACURE compounds are available from Ciba Specialty Chemicals.

Other additional components can be, for example, hydroxy-functional components, such as alcohols, polyester polyols, polyether polyols, hydroxy-group-containing polyurethanes, castor oil, etc. Examples thereof include aliphatic and cycloaliphatic polyols, such as alkylene diols having preferably from 2 to 12 carbon atoms, e.g. ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-di-hydroxymethylcyclohexane, glycerol, tris(β-hydroxy-ethyl)amine, trimethylolethane, tri-methylolpropane, pentaerythritol, dipentaerythritol and sorbitol. The polyols can be partially or fully esterified by one or by different unsaturated carboxylic acids, it being possible for the free hydroxyl groups in partial esters to have been modified, e.g. etherified, or esterified by other carboxylic acids. Examples of esters include: trimethylolpropane triacrylate, trimethylolethane triacrylate, trimethylolpropane trimethacrylate, trimethylolethane trimeth-acrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, or mixtures thereof.

The sulfonium salt compounds of formula I, II, III and IV can also be used, for example, as photo-activatable hardeners for siloxane-group-containing resins. Those resins can, for example, either undergo self-condensation by way of acid-catalysed hydrolysis or can be crosslinked with a second resin component, such as, for example, a polyfunctional alcohol, a hydroxygroup-containing acrylic or polyester resin, a partially hydrolysed polyvinylacetal or a poly-vinyl alcohol. That type of polycondensation of polysiloxanes is described, for example, in J. J. Lebrun, H. Pode, Comprehensive Polymer Science Vol. 5, page 593, Pergamon Press, Oxford, 1989.

Examples of compounds whose solubility increases in a developer under the action of acid, i.e., component (a2) include oligomers, polymers and copolymers that can be obtained by co-polymerisation of, for example, the following monomers: non-cyclic or cyclic secondary and tertiary alkyl (meth)acrylates, such as tert-butyl acrylate, tert-butyl methacrylate, 3-oxocyclohexyl (meth)acrylate, tetrahydropyranyl (meth)acrylate, 2-methyl-2-adamantyl (meth)acrylate, cyclohexyl(meth)acrylate, norbornyl(meth)acrylate, isobornyl methacrylate, 5-norbornene-2-tert-butyl ester, 8-ethyl-8-tricyclodecanyl(meth)acrylate, (2-tetrahydropyranyl)oxynorbornylalcohol acrylates, (2-tetrahydropyranyl) oxymethyltricyclododecanemethanol methacrylates, trimethylsilylmethyl(meth)acrylates, (2-tetrahydropyranyl)oxynorbornylalcohol acrylates, (2-tetrahydropyranyl) oxymethyltricyclododecanemethanol methacrylates, trimethylsilylmethyl(meth)acrylate, o-/m-/p-(3-oxocyclohexyloxy)styrene, o/m-/p-(1-methyl-1-phenylethoxy)styrene, o-/m-/p-tetrahydropyranyloxystyrene, o-/m-/p-adamantyloxystyrene, o-/m-/p-cyclohexyloxystyrene, o-/m-/p-norbornyloxystyrene, non-cyclic or cyclic alkoxycarbonylstyrenes, such as o-/m-/p-tert-butoxycarbonylstyrene, o-/m-/p-(3-oxocyclohexyloxycarbonyl)styrene, o-/m-/p-(1-methyl-1-phenylethoxycarbonyl)styrene, o-/m/p-tetrahydropyranyloxycarbonylstyrene, o-/m-/p-adamantyloxycarbonylstyrene, o-/m-/p-cyclohexyloxycarbonylstyrene, o-/m-/p-norbornyloxycarbonylstyrene, non-cyclic or cyclic alkoxycarbonyloxystyrenes, such as o-/m-/p-tert-butoxycarbonyloxystyrene, o-/m-/p-(3-oxocyclohexyloxycarbonyloxy)styrene, o-/m-/p-(1-methyl-1-phenylethoxycarbonyloxy)styrene, o-/m-/p-tetrahydropyranyloxycarbonyloxystyrene, o-/m-/p-adamantyloxycarbonyloxystyrene, o-/m-/p-cyclohexyloxycarbonyloxystyrene, o-/m-/p-norbornyloxycarbonyloxystyrene, non-cyclic or cyclic alkoxycarbonylalkoxystyrenes, such as o-/m-/p-butoxycarbonylmethoxystyrene, p-tert-butoxycarbonylmethoxystyrene, o-/m-/p-(3-oxocyclohexyloxycarbonylmethoxy)styrene, o-/m-/p-(1-methyl-1-phenylethoxycarbonylmethoxy) styrene, o-/m-/p-tetrahydropyranyloxycarbonylmethoxystyrene, o-/m-/p-adamantyloxycarbonylmethoxystyrene, o-/m-/p-cyclohexyloxycarbonylmethoxystyrene, o-/m-/p-norbornyloxycarbonylmethoxystyrene, trimethylsiloxystyrene, dimethyl(butyl)siloxystyrene, unsaturated alkyl acetates, such as isopropenyl acetate and derivatives thereof, 5-norbornenyl-2-tert-butyl ester; also monomers that carry acid-labile groups having low activation energy, such as, for example, p- or m-(1-methoxy-1-methylethoxy)styrene, p- or m-(1-methoxy-1-methylethoxy)methylstyrene, p- or m-(1-methoxy-1-methylpropoxy)styrene, p- or m-(1-methoxy-1-methylpropoxy)methylstyrene, p- or m-(1-methoxyethoxy)styrene, p- or m-(1-methoxyethoxy) methylstyrene, p- or m-(1-ethoxy-1-methylethoxy)styrenes, p- or m-(1-ethoxy-1-methylethoxy)methylstyrene, p- or m-(1-ethoxy-1-methylpropoxy)styrene, p- or m-(1-ethoxy-1-methylpropoxy)methylstyrene, p- or m-(1-ethoxyethoxy) styrene, p- or m-(1-ethoxyethoxy)methylstyrene, p-(1-ethoxyphenylethoxy)styrene, p- or m-(1-n-propoxy-1-methylethoxy)-styrene, p- or m-(1-n-propoxy-1-methylethoxy)methylstyrene, p- or m-(1-n-propoxyethoxy) styrene, p- or m-(1-n-propoxyethoxy)methylstyrene, p- or m-(1-isopropoxy-1-methylethoxy)styrene, p- or m-(1-isopropoxy-1-methylethoxy)methylstyrene, p- or m-(1-isopropoxyethoxy)styrene, p- or m-(1-isopropoxyethoxy)methylstyrene, p- or m-(1-isopropoxy-1-methyl-propoxy)styrene, p- or m-(1-isopropoxy-1-methylpropoxy)-methylstyrene, p- or m-(1-iso-propoxypropoxy)styrene, p- or m-(1-isopropoxypropoxy)-methylstyrene, p- or m-(1-n-butoxy-1-methylethoxy)styrene, p- or m-(1-n-butoxyethoxy)styrene, p- or m-(1-isobutoxy-1-methyl-ethoxy)styrene, p- or m-(1-tert-butoxy-1-methylethoxy)styrene, p- or m-(1-n-pentyloxy-1-methylethoxy)styrene, p- or m-(1-isoamyloxy-1-methylethoxy)styrene, p- or m-(1-n-hexyloxy-1-methylethoxy) styrene, p- or m-(1-cyclohexyloxy-1-methylethoxy)styrene, p- or m-(1-trimethylsilyloxy-1-methylethoxy)styrene, p- or m-(1-trimethylsilyloxy-1-methylethoxy)-methylstyrene, p- or m-(1-benzyloxy-1-methylethoxy)styrene, p- or m-(1-benzyloxy-1-methylethoxy)methylstyrene, p- or m-(1-methoxy-1-methylethoxy)styrene, p- or m-(1-methoxy-1-methylethoxy)-methylstyrene, p- or m-(1-trimethylsilyloxy-1-methylethoxy)-styrene, p- or m-(1-trimethylsilyloxy-1-methylethoxy)methylstyrene. Further examples of polymers having alkoxyalkyl ester acid-labile groups can be found in U.S. Pat. No. 5,225,316 and EP 829766. Examples of polymers having acetal protecting groups are described, for example, in U.S. Pat. No. 5,670,299, EP 780 732, U.S. Pat. No. 5,627,006, U.S. Pat. No. 5,558,976, U.S. Pat. No. 5,558,971, U.S. Pat. No. 5,468,589, EP 704762, EP 762206, EP 342498, EP 553737 and in ACS Symp. Ser. 614, Microelectronics Technology, pp. 35-55 (1995), J. Photopolymer Sci. Technol. Vol. 10, No. 4 (1997), pp. 571-578, J. Photopolymer Sci. Technol. Vol. 12, no. 4 (1999) pp. 591-599 and in "Proceedings of SPIE", Advances in Resist Technology and Processing XVII, Vol. 3999, Part One, pp. 579-590, 28. February-1. March 2000. The polymers suitable in the composition according to the invention are not, however, limited thereto.

The monomers having an acid-labile group can, where appropriate, also be co-polymerised with other free-radically polymerisable monomers that do not carry acid-labile groups, such as, for example, styrene, acrylonitrile, methyl(meth) acrylate, (meth)acrylic acid, 4-hydroxystyrene, 4-acetoxystyrene, 4-methoxystyrene, 4-vinylcyclohexanol, norbornene, ethylnorbornene and maleic acid anhydride, in order to establish specific solubility properties and adhesive properties. Alternatively, the acid-labile groups can be introduced only subsequently in a polymer-analogous reaction. It is also known to the person skilled in the art that the prepolymer can be modified in targeted manner before such a polymer-analogous reaction, for example by partial hydrogenation, partial alkylation, partial acetylation. That is to say, that the polymer having acid-labile groups does not, in every case, have to be synthesised from monomers by copolymerisation.

It is also possible to introduce acid-labile crosslinking, as described, for example, in H.-T. Schacht, P. Falcigno, N. Muenzel, R. Schulz and A. Medina, ACS Symp. Ser. 706 (Micro- and Nanopatterning Polymers), pp. 78-94, 1997; H.-T. Schacht, N. Muenzel, P. Falcigno, H. Holzwarth and J. Schneider, J. Photopolymer Science and Technology, Vol. 9, (1996), 573-586. Such acid-crosslinked systems are preferred in resist applications from the standpoint of heat stability. Such acid-labile crosslinking can also be obtained by the reaction of phenol-group-containing polymers, such as, for example, 4-hydroxystyrene co-polymers, with di- and polyfunctional vinyl ethers.

Other examples of component (a2) that increase their solubility in an alkaline developer upon reaction with acid are monomeric compounds, such as, for example, carboxylic acids and phenol-group-containing compounds, in which the carboxylic acid group or phenolic OH group, respectively, has been blocked by acid-labile protecting groups. Such acid-labile blocking can be effected, for example, by conversion of the carboxyl group into a tert-butyl ester group, a 2-methyl-2-adamantyl ester group, an 8-ethyl-8-tricyclodecanyl ester group, a tetrahydropyranyl ester group or some other acid-cleavable ester group. Phenolic OH groups can be blocked according to known processes by conversion, e.g. into acid-cleavable tert-butylcarbonate groups, silyl ethers, acetal groups and ketal groups.

The invention relates also to a radiation-sensitive composition wherein component (a2) is at least one compound selected from the group of cycloaliphatic copolymers, 4-hydroxy-phenyl-group-containing copolymers, maleic acid anhydride-containing copolymers and acrylic acid-, acrylic acid ester- and methacrylic acid ester-containing copolymers, with the proviso that those copolymers carry functional groups that increase the solubility of the polymer in an alkaline developer after reaction with an acid.

In the compositions according to the invention, the photoinitiator (b) is advantageously used in an amount of from 0.05% to 15%, e.g. from 0.5% to 10%, preferably from 0.1% to 5%, based on the composition.

The compositions according to the invention can be used in numerous applications, for example in cationically radiation-curable printing inks, in cationically radiation-curable coating compounds which may or may not be pigmented, in cationically radiation-curable adhesives, coatings and mouldings, including glass fibre-reinforced and carbon fibre-reinforced composites and inner and outer layers of printed circuit boards.

The compositions according to the invention include also adhesives, as used, for example, for adhesive bonding (DVD bonding) in the manufacture of digital versatile disks (DVD) and as described, for example, in: WO 99/66506, WO 99/63017, JP 11241055 A2 Heisei, JP 11181391 A2 Heisei, WO 98/31765, and also as radiation-curable laminating adhesives for flexible packaging (see, e.g., U.S. Pat. No. 5,328, 940), optical adhesives (e.g. German Patent Application DD 225985) and pressure-sensitive adhesives (e.g. U.S. Pat. No. 4,988,741 and EP 115870).

The compositions according to the invention are advantageously used where there is a need for hard coatings, adhesive bonds or photopolymerised dimensionally stable three-dimensional mouldings (e.g. for rapid prototyping) having good adhesion to paper, glass, metal, silicon, polycarbonate, acrylate polymers and other polymer substrates, and that exhibit only slight shrinkage during curing.

Preference is also given to a composition as described above that comprises in addition to components (a1) or (a2) and (b), additional additives (c) and/or sensitiser compounds (d) and optionally further photoinitiators (e).

The photopolymerisable mixtures can comprise various additives (c) in addition to the photoinitiator. Examples thereof include thermal inhibitors, light stabilisers, optical brighteners, fillers and pigments, as well as white and coloured pigments, dyes, antistatics, adhesion promoters, wetting agents, flow auxiliaries, lubricants, waxes, anti-adhesive agents, dispersants, emulsifiers, anti-oxidants, fillers, e.g. talcum, gypsum, silicic acid, rutile, carbon black, zinc oxide, iron oxides, reaction accelerators, thickeners, matting agents, antifoams, and other adjuvants customary, for example, in lacquer and coating technology.

The formulations can also comprise dyes and/or white or coloured pigments as additional additives (c). Depending upon the intended use, it is possible to use both inorganic and organic pigments. Such additives are known to the person skilled in the art; some examples thereof are titanium dioxide pigments, for example of the rutile or anatase type, carbon black, zinc oxide, such as zinc white, iron oxides, such as iron oxide yellow, iron oxide red, chromium yellow, chromium green, nickel titanium yellow, ultramarine blue, cobalt blue, bismuth vanadate, cadmium yellow and cadmium red. Examples of organic pigments are mono- or bis-azo pigments, and metal complexes thereof, phthalocyanine pigments, polycyclic pigments, such as, for example, perylene, anthraquinone, thioindigo, quinacridone and triphenylmethane pigments, and diketo-pyrrolo-pyrrole, isoindolinone, e.g. tetrachloro-isoindolinone, isoindoline, dioxazine, benzimidazolone and quinophthalone pigments.

The pigments can be used individually or in admixture in the formulations. Depending upon the intended use, the pigments are added to the formulations in amounts customary in the art, for example in an amount of from 1 to 60% by weight, or from 10 to 30% by weight, based on the total weight.

The formulations may, for example, also comprise organic dyes of a wide variety of classes. Examples thereof include azo dyes, methine dyes, anthraquinone dyes and metal complex dyes. Customary concentrations are, for example, from 0.1 to 20%, especially from 1 to 5%, based on the total weight.

The pigments, latent pigments or dyes or differently coloured precursors of such pigments and dyes that are added may be so selected that they undergo a colour change in the presence of the acid formed from the iodonium salt as a result of irradiation. Such compositions then show, by the colour change, that they have been irradiated and can be used, for example, as irradiation dose indicators, e.g. for UV radiation, electron beams, X-rays, etc.

The choice of additives will depend upon the field of use in question and upon the properties desired for that field. The additives (c) described above are customary in the art and are accordingly used in amounts customary in the art.

The compositions according to the present invention as component (c) also may comprise a stabilizer for the compounds of the formula I, II, III and IV, e.g. from the hindered nitroxyl or phosphite type as are for example described as stabilizers for iodonium salts in WO 05/070989.

Examples for said stabilizer compounds are organic phosphorus stabilizers as disclosed for example in U.S. Pat. No. 6,444,733, the disclosure of which is hereby incorporated by reference. Organic phosphorus stabilizers are known and many are commercially available. Other examples for said stabilizer compounds are hindered nitroxyl stabilizers, or hindered nitroxides, as are well known in the art and are disclosed for example in U.S. Pat. No. 6,337,426 and, U.S. Pat. No. 5,254,760, the relevant disclosures of which are hereby incorporated by reference.

Other suitable stabilizers (c) for the sulfonium salts of the formula I, II, III and IV are for example disclosed in WO 99/35188. Examples are tertiary and sterically hindered amines, such as the Tinuvin® products, provided by Ciba Specialty Chemicals, in particular Tinuvin® 144 and Tinuvin® 292.

Acceleration of the photopolymerisation can also be effected by adding as further additives (d) photosensitisers that shift or broaden the spectral sensitivity. These are especially aromatic carbonyl compounds, such as, for example, benzophenone, thioxanthone, and especially also isopropylthioxanthone, phenothiazine derivatives, anthraquinone and 3-acylcoumarin derivatives, terphenyls, styryl ketones, and 3-(aroylmethylene)-thiazolines, camphorquinone, and also eosin, rhodamine and erythrosin dyes, and anthracene derivatives, such as, for example, 9-methylanthracene, 9,10-dimethylanthracene, 9,10-diethoxyanthracene, 9,10-dibutyloxyanthracene, 9-methoxyanthracene, 9-anthracenemethanol, especially 9,10-dimethoxy-2-ethyl-anthracene, 9,10-dibutyloxyanthracene and 9,10-diethoxyanthracene. Further suitable photosensitisers are mentioned, for example, in WO 9847046. Subject of the invention also are radiation-sensitive compositions as described above, additionally to components (a1) or (a2) and (b) comprising at least one sensitizer compound (d), in particular benzophenone, thioxanthone, anthracene or derivatives thereof.

It is also possible to use electron donor compounds, such as, for example, alkyl- and arylamine donor compounds, in the composition. Such compounds are, for example, 4-dimethylaminobenzoic acid, ethyl 4-dimethylaminobenzoate, 3-dimethylaminobenzoic acid, 4-dimethylaminobenzoin, 4-dimethylaminobenzaldehyde, 4-dimethylaminobenzonitrile and 1,2,4-trimethoxybenzene. Such donor compounds are preferably used in a concentration of from 0.01 to 5%, especially in a concentration of from 0.05 to 0.50%, based on the formulation.

Further examples of suitable photosensitisers (d) are
1. Thioxanthones thioxanthone, 2-isopropylthioxanthone, 2-chlorothioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxy-carbonylthioxanthone, 3-butoxycarbonyl-7-methylthioxanthone, 1-chloro-4-propoxythioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxy-carbonyl-3-phenylsulfurylthioxanthone, 3,4-di[2-(2-methoxyethoxy)ethoxycarbonyl]thiox-anthone, 1-ethoxycarbonyl-3-(1-methyl-1-morpholinoethyl)-thioxanthone, 2-methyl-6-di-methoxymethylthioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxythioxanthone, 6-ethoxycarbonyl-2-methoxythioxanthone, 6-ethoxycarbonyl-2-methylthioxanthone, 1,3-dimethyl-2-hydroxy-9H-thiox-anthen-9-one-2-ethylhexyl ether, thioxanthone-2-polyethylene glycol ester, 2-hydroxy-3-(3,4-dimethyl-9-oxo-9H-thioxanthon-2-yloxy)-N,N,N-trimethyl-1-propanaminium chloride;

2. Benzophenones benzophenone, 4-phenyl benzophenone, 4-methoxy benzophenone, 4,4'-dimethoxy benzophenone, 4,4'-dimethyl benzophenone, 4,4'-dichlorobenzophenone 4,4'-bis(dimethylamino)benzophenone, 4,4'-bis(diethylamino)benzophenone, 4,4'-bis(methylethylamino)benzophenone, 4,4'-bis(p-isopropylphenoxy)benzophenone, 4-methyl benzophenone, 2,4,6-trimethylbenzophenone, 3-methyl-4'-phenyl-benzophenone, 2,4,6-trimethyl-4'-phenyl-benzophenone, 4-(4-methylthiophenyl)-benzophenone, 3,3'-dimethyl-4-methoxy benzophenone, methyl-2-benzoylbenzoate, 4-(2-hydroxyethylthio)-benzophenone, 4-(4-tolylthio) benzophenone, 1-[4-(4-benzoyl-phenylsulfanyl)-phenyl]-2-methyl-2-(toluene-4-sulfonyl)-propan-1-one, 4-benzoyl-N,N-trimethylbenzenemethanaminium chloride, 2-hydroxy-3-(4-benzoylphenoxy)-N,N,N-trimethyl-1-propanaminium chloride monohydrate, 4-(13-acryloyl-1,4,7,10,13-pentaoxamidecyl)benzophenone, 4-benzoyl-N,N-dimethyl-N-[2-(1-oxo-2-propenyl)oxy]ethyl-benzenemethanaminium chloride;

3. 3-Acylcoumarins 3-benzoylcoumarin, 3-benzoyl-7-methoxycoumarin, 3-benzoyl-5,7-di(propoxy)coumarin, 3-benzoyl-6,8-dichlorocoumarin, 3-benzoyl-6-chlorocoumarin, 3,3'-carbonyl-bis[5,7-di-(propoxy)coumarin], 3,3'-carbonyl-bis(7-methoxycoumarin), 3,3'-carbonyl-bis(7-diethyl-aminocoumarin), 3-isobutyroylcoumarin, 3-benzoyl-5,7-dimethoxycoumarin, 3-benzoyl-5,7-diethoxycoumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)coumarin, 5,7-dimethoxy-3-(1-naphthoyl)coumarin, 3-benzoylbenzo-[f]-coumarin, 7-diethylamino-3-thienoylcoumarin, 3-(4-cyanobenzoyl)-5,7-dimethoxycoumarin;

4. 3-(Aroylmethylene)-thiazolines 3-methyl-2-benzoylmethylene-β-naphthothiazoline, 3-methyl-2-benzoylmethylene-benzo-thiazoline, 3-ethyl-2-propionylmethylene-β-naphthothiazoline;

5. Other carbonyl compounds acetophenone, 3-methoxyacetophenone, 4-phenylacetophenone, benzil, 2-acetyl-naphthalene, 2-naphthaldehyde, 9,10-anthraquinone, 9-fluorenone, dibenzosuberone, xanthone, 2,5-bis(4-diethylaminobenzylidene)cyclopentanone, α-(para-dimethyl-aminobenzylidene)ketones, such as 2-(4-dimethylaminobenzyl idene)-indan-1-one or 3-(4-dimethylamino-phenyl)-1-indan-5-yl-propenone, 2-benzoyl-3-(4-dimethylaminophenyl)-2-propene-nitrile, 3-phenylthiophthalimide, N-methyl-3,5-di(ethylthio)phthalimide, N-methyl-3,5-di(ethylthio)phthalimide.

The sensitisers (d) described above are customary in the art and are accordingly used in amounts customary in the art, preferably in a concentration of from 0.05 to 5%, especially in a concentration of from 0.1 to 2%, based on the composition.

The compositions according to the invention may additionally comprise further photo-initiators (e), such as, for example, cationic photoinitiators, photo acid-formers and free-radical photoinitiators as co-initiators in amounts of from 0.01 to 15%, preferably from 0.1 to 5%.

Examples of cationic photoinitiators and acid-formers are phosphonium salts, diazonium salts, pyridinium salts, iodonium salts, such as for example tolylcumyliodonium tetrakis (pentafluorophenyl)borate, 4-[(2-hydroxy-tetradecyloxy) phenyl]phenyliodonium hexafluoroantimonate or hexafluorophosphate (SarCat® CD 1012; Sartomer), tolylcumyliodonium hexafluorophosphate, 4-isobutylphenyl-4'-methylphenyliodonium hexafluorophosphate (Irgacure®250, Ciba Specialty Chemicals), 4-octyloxyphenyl-phenyliodonium hexafluorophosphate or hexafluoroantimonate, bis(dodecylphenyl)iodonium hexafluoroantimonate or hexafluorophosphate, bis(4-methylphenyl)iodonium hexafluorophosphate, bis(4-methoxyphenyl)iodonium hexafluorophosphate, 4-methylphenyl-4'-ethoxyphenyliodonium hexafluorophosphate, 4-methylphenyl-4'-dodecylphenyliodonium hexafluorophosphate, 4-methylphenyl-4'-phenoxyphenyliodonium hexafluorophosphate. Of all the iodonium salts mentioned, compounds with other anions are, of course, also suitable; further sulfonium salts, obtainable, for example, under the trade names ®Cyracure UVI-6990, ®Cyracure UVI-6974 (Union Carbide), ®Degacure KI 85 (Degussa), SP-55, SP-150, SP-170 (Asahi Denka), GE UVE 1014 (General Electric), SarCat® KI-85 (=triarylsulfonium hexafluorophosphate; Sartomer), SarCat® CD 1010 (=mixed triarylsulfonium hexafluoroantimonate; Sartomer); SarCat® CD 1011 (=mixed triarylsulfonium hexafluorophosphate; Sartomer); ferrocenium salts, e.g. ($\eta^6$-isopropylbenzene)($\eta^5$-cyclopentadienyl)-iron-II hexafluorophosphate Irgacure® 261, nitrobenzylsulfonates, alkyl- and aryl-N-sulfonyloxyimides and further known alkylsulfonic acid esters, haloalkylsulfonic acid esters, 1,2-disulfones, oxime sulfonates, benzoin tosylate, tolylsulfonyloxy-2-hydroxy-2-methyl-1-phenyl-1-propanone and further known beta-ketosulfones, beta-sulfonylsulfones, bis(alkylsulfonyl)diazomethane, bis(4-tert-butylphenyl-sulfonyl)-diazomethane, benzoyl-tosyl-diazomethane, iminosulfonates and imidosulfonates and trichloromethyl-s-triazines and other haloalkyl-group-containing compounds and further compounds mentioned under (b1) below.

Examples of free-radical photoinitiators as co-initiators are compounds as described above.

The compositions according to the invention may be used for a variety of purposes, for example as printing inks, such as screen-printing inks, flexo printing inks or offset printing inks, as clear lacquer, as coloured surface-coating compositions, as white surface-coating compositions, e.g. for wood or metal, as powder coating compositions, as paint, inter alia for paper, wood, metal or plastics, as daylight-curable paint for marking structures and roads, for photographic reproduction processes, for holographic recording materials, for image-recording processes or for the production of printing plates that are to be developed with organic solvents or using aqueous-alkaline media, in the production of masks for screen-printing, as dental filling compounds, as radiation-curable adhesives, as pressure-sensitive adhesives, as anti-adhesive coatings, as laminating resins, as photoresists, e.g. galvano-resists, etch resists or permanent resists, liquid films and dry films, as photostructurable dielectrics, and as solder masks for electronic circuits, as resists in the manufacture of colour filters for any type of screen or for producing structures in the manufacture of plasma displays and electroluminescent displays, in the manufacture of optical switches, optical gratings (interference gratings), in the coating or sealing of electronic components, e.g. as electroinsulating compounds, or as coatings for optical fibres, for coil coating, as indicator systems for UV radiation, X-rays and electron beams, and in the manufacture of three-dimensional articles, e.g. for stereolithography and for composites, e.g. for composites reinforced with glass or carbon or graphite fibres. The compositions are also suitable for the manufacture of optical lenses, e.g. contact lenses or Fresnel lenses, and also in the manufacture of medical apparatus, aids or implants.

The photocurable compositions according to the invention are suitable, for example, as coating materials for all kinds of substrates, for example wood, textiles, paper, ceramics, glass, marble, plastics, such as polyester, polyethylene terephthalate, polyolefins or cellulose acetate, especially in the form of films, and metals, such as Al, Cu, Ni, Fe, Zn, Mg or Co and GaAs, Si or $SiO_2$, to which a coating is to be applied or an image is to be applied by image-wise exposure, or to which a structured resist layer is to be applied.

The coating of the substrates can be effected by applying a liquid composition, a solution or suspension to the substrate. The choice of solvent and the concentration are governed chiefly by the nature of the composition and by the coating method. The solvent should be inert, that is to say it should not enter into any chemical reaction with the components and it should be capable of being removed again upon drying after the coating operation.

Examples of suitable solvents are ketones, ethers and esters, such as methyl ethyl ketone, isobutyl methyl ketone, cyclopentanone, cyclohexanone, 2-heptanone, methyl amyl ketone, N-methylpyrrolidone, gamma-butyrolactone, dioxane, tetrahydrofuran, 2-methoxyethanol, 2-ethoxyethanol, 1-methoxy-2-propanol, 1,2-dimethoxyethane, acetic acid ethyl ester, acetic acid n-butyl ester, propylene glycol monomethyl ether acetate, lactic acid ethyl ester, propylene carbonate and 3-ethoxy-propionic acid ethyl ester.

After coating of the substrates, the solvent is generally removed by drying.

The formulation is applied uniformly to a substrate by known coating methods, for example by spin-coating, immersion, knife coating, curtain pouring, brush application or spraying, especially by electrostatic spraying and reverse-roll coating, and by electrophoretic deposition. It is also possible to apply the photosensitive layer to a temporary flexible support and then coat the final substrate, e.g. a copper-laminated printed circuit board, by transferring the layer by lamination.

The amount applied (layer thickness) and the type of substrate (layer support) are dependent upon the desired field of use. The layer thickness range generally includes values from about 0.1 µm to more than 100 µm, preferably from 0.5 micrometre to 50 micrometres. In the manufacture of three-dimensional articles, e.g. by stereolithography, the dimensions of the articles that can be obtained are limited only by the size of the exposure apparatus.

The radiation-sensitive compositions according to the invention are used, for example, as negative resists that have very high photosensitivity and that can be developed in an aqueous-alkaline medium without swelling. They are suitable as photoresists for electronics, such as galvanoresists, etch resists, and in liquid and dry films, solder resists, as resists in the production of colour filters for any type of screen, or to form structures in the manufacture of plasma displays and electroluminescent displays, in the manufacture of printing plates, e.g. offset printing plates, in the manufacture of printing moulds for letterpress printing, flatbed printing, intaglio printing, flexo printing or screen-printing moulds, the production of relief copies, e.g. for the production of texts in braille, for the production of stamps, for use in the etching of mouldings or for use as a microresist in the manufacture of integrated switching circuits. The compositions can also be used as photostructurable dielectrics, for encapsulating materials or as an insulating coating in the manufacture of computer chips, printed circuits and other electrical or electronic components. The possible layer supports and processing conditions for the coated substrates vary accordingly.

The compounds according to the invention are also used in the manufacture of single- or multi-layer materials for image recording or image reproduction (copies, reprography), which may be monochromatic or polychromatic. Included therein are materials for holographic storage of information, e.g. for holographic images or 3-dimensional holographic data storage. Such materials can also be used in colour test systems. In that technology it is also possible to use formulations that comprise microcapsules and, to produce the image, a thermal step can be carried out after the exposure step. Such systems and technologies and their use are described, e.g., in U.S. Pat. No. 5,376,459.

For photographic recordings of information there are used, for example, films of polyester, cellulose acetate or plastics-coated papers; for offset printing moulds there is used specially treated aluminium; for the production of printed circuits there are used copper-coated laminates; and for the production of integrated switching circuits there are used silicon wafers. The layer thicknesses for photographic materials and offset printing moulds are generally from about 0.5 µm to 10 µm, and for printed circuits from 1.0 µm to about 100 µm.

The invention relates also to the use of compounds of formula I, II, III and IV as radiation-sensitive acid donors in the manufacture of surface-coating compositions, printing inks, printing plates, dental compounds, stereolithography resins, adhesives, anti-adhesive coatings, colour filters, resist materials or image-recording materials.

The invention relates also to a coated substrate that is coated on at least one surface with a composition according to the invention, and to a method for the production of relief images wherein a composition according to the invention is applied to a substrate and is then exposed image-wise.

The expression "image-wise exposure" includes irradiation through a mask that contains a predetermined pattern, for example a diapositive, a metal mask, a chrome mask on a trans-parent support, exposure by means of a laser beam that is moved, for example controlled by a computer, over the surface of the coated substrate and in that manner produces an image, and irradiation with computer-controlled electron beams (CTP). Images can also be produced by interference between two beams or images, for example for holographic uses. It is also possible to use liquid crystal masks that can be actuated pixel by pixel to produce digital images, as described, for example, by A. Bertsch, J. Y. Jezequel, J. C. Andre in Journal of Photochemistry and Photobiology A: Chemistry 1997, 107, pp. 275-281 and by K.-P. Nicolay in Offset Printing 1997, 6, pp. 34-37.

As already mentioned, the compounds of formula I; II, III and IV can be used especially also as acid donors in photoresists. Resist systems can be obtained by image-wise exposure of formulations comprising compounds of formula I, II, III and IV and a subsequent development step. The term "photoresist" is not limited to the chemically enhanced resists described in greater detail below, but includes all resist materials in which reactions are initiated by the radiation-chemical production of acid and that, in a development step, result in a difference in solubility between exposed and non-exposed regions. For example, also included are resists that can be processed in an aqueous medium, as described, for example, in U.S. Pat. No. 5,998,092 and in SPIE, Vol. 3999, pp. 569-578 (2000) as well as resists based on a Pinacol rearrangement, as described, for example, in SPIE, Vol. 3999, pp. 62-73 (2000).

Accordingly, the invention relates also to a photoresist that comprises a compound of formula I, II, III or IV as radiation-sensitive acid donor.

A chemically enhanced photoresist is to be understood as being a resist formulation in which the radiation-sensitive component provides a catalytic amount of acid, which in turn catalyses a chemical reaction of at least one acid-sensitive component of the resist. This results in a difference in the solubility of the irradiated and non-irradiated portions of the resist. As a result of the catalytic nature of that process, an acid molecule can initiate reactions at many sites because it diffuses through the reactive polymer matrix from one reaction site to the next, provided it is not captured or destroyed by secondary reactions. Even a low acid concentration is therefore sufficient to obtain large differences in solubility between irradiated and non-irradiated portions of the resist. It is therefore generally sufficient to add only a small amount of latent acid compound. It is necessary, however, for the latent acid donors to be chemically and thermally stable until they are being irradiated. It is also necessary for the latent catalysts to be readily soluble in the liquid resist formulation and in the solid resist film in order to avoid the formation of particles which would adversely affect the use of the resists in microelectronic processing processes.

It will be clear from the above remarks that chemical and thermal stability of the latent acid donor is essential for its use in chemically enhanced photoresists.

The difference in solubility between exposed and non-exposed areas in the resist, which results from the action of the acid-catalysed reaction, depends upon the other components in the resist. If the compositions according to the invention comprise components that increase the solubility of the composition in the developer after irradiation and optionally after thermal aftertreatment, then it is a positive photoresist.

The invention accordingly relates also to a positive photoresist.

If, however, the components of the composition lower the solubility in the developer after irradiation and optionally after thermal aftertreatment, then it is a negative photoresist.

The invention accordingly relates also to a negative photoresist.

An overview of chemically enhanced photoresists can be found, for example, in: H. Ito, IBM Journal of Research and Development, Vol. 41, No. 1/2, page 69 (1997); H. Ito, SPIE Vol. 3678, page 2 (1999); for negative resists in: J. M. Shaw et al. IBM Journal of Research and Development, Vol. 41, No. 1/2, page 81 (1997).

A monomeric, oligomeric or polymeric compound that, in non-exposed portions, lowers the rate of solubility of an alkali-soluble binder polymer also present in the resist formulation, and that is itself alkali-insoluble in the non-exposed portions, with the result that the resist film is retained in the non-exposed portions after development in an alkaline solution, but that is cleaved in the presence of an acid or is capable of being rearranged in such a manner that the reaction product becomes soluble in an alkaline developer, is referred to hereinafter as a solubility inhibitor.

The invention also includes a chemically enhanced positive photoresist composition that can be developed in an alkaline medium, which photoresist composition comprises (a3) at least one polymer having acid-labile groups that decompose in the presence of an acid and increase the solubility of the resist film in an alkaline developer solution in the irradiated areas, and (b) at least one compound of formula I, II, III or IV.

The invention relates also to a chemically enhanced positive photoresist composition that can be developed in an alkaline medium, which photoresist composition comprises (a4) at least one monomeric or oligomeric solubility inhibitor having at least one acid-labile group that decomposes in the presence of an acid and that increases the solubility in aqueous-alkaline developer solutions, and at least one alkali-soluble polymer, and (b) at least one compound of formula I; II, III or IV.

The invention relates also to a chemically enhanced positive photoresist composition that can be developed in an alkaline medium, which photoresist composition comprises (a3) at least one polymer having acid-labile groups that decompose in the presence of an acid and increase the solubility in an aqueous-alkaline developer solution in the exposed area;

(a4) a monomeric or oligomeric solubility inhibitor having at least one acid-labile group that decomposes in the presence of an acid and that increases the solubility in an aqueous-alkaline developer solution in the exposed area;

(a5) an alkali-soluble monomeric, oligomeric or polymeric compound in a concentration that keeps the resist film in non-exposed areas completely insoluble in an alkaline developer, and (b) at least one compound of formula I, II, III or IV.

The invention relates also to a chemically enhanced photoresist composition comprising (a3) at least one polymer having an acid-labile group that decomposes in the presence of an acid and increases the solubility in an aqueous-alkaline developer solution, and/or (a4) at least one monomeric or oligomeric solubility inhibitor having an acid-labile group that decomposes in the presence of an acid and increases the solubility in an aqueous-alkaline developer solution, and/or (a5) at least one alkali-soluble monomeric, oligomeric or polymeric compound; and (b) as photosensitive acid donor at least one compound of formula I, II, III or IV.

The compositions may comprise, in addition to component (b), other photosensitive acid donors and/or other additives (c) and/or photosensitisers (d).

Appropriate suitable additives (c) and photosensitisers (d) have been described hereinabove.

Such chemically enhanced positive photoresist systems are described, for example, in E. Reichmanis, F. M. Houlihan, O, Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139.

Suitable examples of acid-labile groups that decompose in the presence of an acid and form aromatic hydroxyl groups, carboxyl groups, keto groups and aldehyde groups and increase the solubility in aqueous-alkaline developer solutions include alkoxyalkyl ether groups, benzyl ether groups, tetrahydrofuranyl ether groups, tetrahydropyranyl ether groups, tert-alkyl ester groups, 2-methyl-2-adamantyl ester groups, 8-ethyl-8-tricyclo-decanyl ester groups, trityl ether groups, silyl ether groups, alkylcarbonate groups, such as, for example, tert-butyloxycarbonyloxy groups, trityl ester groups, silyl ester groups, alkoxy-methyl ester groups, cumyl ester groups, acetal groups, ketal groups, tetrahydropyranyl ester groups, tetrafuranyl ester groups, tertiary alkyl ether groups, tertiary alkyl ester groups, etc.

The polymers having functional groups that decompose under the action of an acid in order to increase the solubility of the resist film comprising that polymer in an alkaline developer solution and that can be added to the compositions of the present invention can carry the acid-labile groups in the polymer backbone and/or in the side chains. The acid-labile groups are preferably situated in the side chain of the polymer.

Suitable polymers having acid-labile groups can be obtained by polymer-analogous reactions in which some or all of the alkali-soluble groups are converted into the acid-labile group in question. Also possible is the direct preparation by (co)polymerisation of monomers that already contain the acid-labile groups. Examples of the preparation have been published in EP 254853, EP 878738, EP 877293, JP 2-25850-A, JP 3-223860-A, and JP 4-251259-A.

In polymers containing, for example, silyl ether, acetal, ketal and alkoxyalkyl ester groups (socalled low-activation energy blocking groups—protecting groups having low activation energy), such protecting groups are cleaved in the presence of an acid at relatively low temperatures upon heating after exposure (generally between room temperature and 110° C.). Polymers that carry tert-butyl ester groups, adamantyl ester groups or tert-butyloxycarbonyl groups (TBOC groups) or other ester groups that carry a secondary or tertiary carbon atom in addition to the oxygen atom of the ester bond (so-called high-activation energy blocking groups—protecting groups having high activation energy) generally require heating to achieve complete cleavage of the protecting groups in the presence of an acid after exposure. Hybrid systems in which both high-activation energy protecting groups and low-activation energy protecting groups are present in the same polymer can also be used. So-called "dual-mode" protecting groups are also known, which combine within them a readily cleavable bond, e.g. in an acetal group, and a bond that is more difficult to cleave, e.g. in a tert-butyl ester group, as described, for example, in "Proceedings of SPIE", Advances in Resist Technology and Processing XVII, Vol. 3999, Part One, pages 579-590, 28. February-1. March 2000. Mixtures of polymers having different protecting group chemistry can also be used in the photosensitive compositions according to the invention.

Preferred polymers having acid-labile protecting groups are polymers and copolymers comprising the following different monomer types:
1) monomers that contain acid-labile groups that decompose in the presence of an acid and increase the solubility in an aqueous-alkaline developer solution, and
2) monomers that are free of acid-labile groups and free of groups that contribute to the solubility in an alkaline solution, and/or
3) monomers that contribute to the aqueous-alkali solubility of the polymer.

Examples of monomers of type 1) are those already described above as a suitable component (a2).

Examples of comonomers of type 2) are:
aromatic vinyl monomers, such as styrene, α-methylstyrene, acetoxystyrene, α-methylnaphthalene, acenaphthalene, vinyl ethers, such as ethyl vinyl ether and 3,4-dihydro-2Hpyran, cyclohexylvinyl ether, cycloolefins, such as norbornene, 2-hydroxy-5-norbornene, 2-norbornen-5-yl-(2-hydroxyethyl)carboxylate, vinyl alicyclic compounds, such as vinyl norbornane, vinyl adamantane, vinyl cyclohexane, alkyl (meth)acrylates, such as methyl methacrylate, acrylonitrile, vinyl cyclohexane, vinyl cyclohexanol, and maleic acid anhydride.

Examples of comonomers of type 3) are:
vinyl aromatic compounds, such as hydroxystyrene, acrylic acid compounds, such as methacrylic acid, ethylcarbonyloxystyrene and derivatives thereof and cycloolefinic acids, such as 5-norbornene-2-carboxylic acid. Such polymers are described, for example, in U.S. Pat. No. 5,827,634, U.S. Pat. No. 5,625,020, U.S. Pat. No. 5,492,793, U.S. Pat. No. 5,372,912, EP 660187, U.S. Pat. No. 5,679,495, EP 813113 and EP 831369. Further examples are crotonic acid, isocrotonic acid, 3-butenoic acid, acrylic acid, 4-pentenoic acid, propionic acid, 2-butynoic acid, maleic acid, fumaric acid and acetylenecarboxylic acid. The polymers that are suitable in the composition according to the invention are not, however, limited to the examples given above.

The content of acid-labile monomer in the polymer can vary within a wide range and is dependent upon the content of other comonomers and the alkali-solubility of the protected polymer. Generally the content of monomer having acid-labile groups in the polymer is from 5 to 60 mol %.

The copolymers having acid-labile groups preferably have a $M_w$ of from about 3000 to about 200 000, especially from about 5000 to about 50 000 and a molecular weight distribution of about 3 or less, especially about 2 or less. Non-phenolic monomers, e.g. a copolymer of alkyl acrylate, such as, for example, tert-butyl acrylate or tert-butyl methacrylate, and an alicyclic vinyl compound, such as a vinyl norbonanyl or vinylcyclohexanol compound, can be obtained by free-radical polymerisation or other known processes and advantageously have a $M_w$ value of from about 8000 to about 50 000, and a molecular weight distribution of about 3 or less.

Other comonomers can be added advantageously in a suitable amount in order, for example, to control the glass transition temperature or the like.

In the present invention it is also possible to use mixtures of two or more polymers having acid-labile groups. For example, a mixture of polymers having acid-labile groups that cleave very readily, such as acetal groups or tetrahydropyranyloxy groups, and a polymer having acid-labile groups that cleave less readily, such as, for example, tertiary alkyl ester groups, can be used. It is also possible to use acid-labile groups of different sizes by mixing two or more polymers having different acid-labile groups, such as, for example, a tert-butyl ester group and a 2-methyl-adamantyl group or a 1-ethoxy-ethoxy group and a tetrahydropyranyloxy group. A mixture of non-crosslinked resin and crosslinked resin can also be used.

According to the invention, the proportion of such polymers is preferably from about 30 to 99% by weight, especially from 50 to 98% by weight, based on the solids content. An alkali-soluble resin or an alkali-soluble monomeric or oligomeric compound without acid-labile groups can also be introduced into the composition, for example in order to control the alkali-solubility. Examples of polymer mixtures having different acid-labile groups can be found, for example, in EP 780732, EP 679951 and U.S. Pat. No. 5,817,444.

Monomeric and oligomeric solubility inhibitors (a4) are preferably used in the composition according to the invention.

Suitable monomeric or oligomeric solubility inhibitors (a4) in the composition according to the invention are compounds having at least one acid-labile group that cleaves in the presence of acid and increases solubility in an aqueous-alkaline developer solution. Examples thereof include alkoxymethyl ether groups, tetrahydrofuranyl ether groups, tetrahydro-pyranyl ether groups, alkoxyethyl ether groups, trityl ether groups, silyl ether groups, alkylcarbonate groups, trityl ester groups, silyl ester groups, alkoxymethyl ester groups, vinyl carbamate groups, tertiary alkyl carbamate groups, tritylamino groups, cumyl ester groups, acetal groups, ketal groups, tetrahydropyranyl ester groups, tetrafuranyl ester groups, tertiary alkyl ether groups, tertiary alkyl ester groups, etc. The molecular weight of the acid-cleavable solubility inhibitors suitable in the present invention is about 3000 or less, especially from about 100 to 3000, preferably from about 200 to 2500.

Examples of monomeric and oligomeric solubility inhibitors having acid-labile groups are described, for example, as compounds of formulae (I) to (XVI) in EP 831369. Other suitable examples of such compounds are given in U.S. Pat. No. 5,356,752, U.S. Pat. No. 5,037,721, U.S. Pat. No. 5,015,554, JP-A-1-289946, JP-A-1-289947, JP-A-2-2560, JP-A-3-128959, JP-A-3-158855, JP-A-3-179353, JP-A-3-191351, JP-A-3-200251, JP-A-3-200252, JP-A-3-200253, JP-A-3-200254, JP-A-3-200255, JP-A-3-259149, JA-3-279958, JP-A-3-279959, JP-A-4-1650, JP-A-4-1651, JP-A-11260, JP-A-4-12356, JP-A-4-123567, JP-A-1-289946, JP-A-3-128959, JP-A-3-158855, JP-A-3-179353, JP-A-3-191351, JP-A-3-200251, JP-A-3-200252, JP-A-3-200253, JP-A-3-200254, JP-A-3-200255, JP-A-3-259149, JA-3-279958, JP-A-3-279959, JP-A-4-1650, JP-A-4-1651, JP-A-11260, JP-A-4-12356, JP-A-4-12357 and Japanese Patent Application Nos. 3-33229, 3-230790, 3-320438, 4-254157, 4-52732, 4-103215, 4-104542, 4-107885, 4-107889, 4-152195, 4-254157, 4-103215, 4-104542, 4-107885, 4-107889 and 4-152195. Suitable for resists in the shortwave UV range are, for example, especially compounds such as tert-butyl cholate, tert-butyl deoxycholate and tert-butylcholate glutarate dimers (see, e.g., SPIE Vol. 3999, p. 127 (2000).

The composition according to the invention may also comprise polymeric solubility inhibitors, for example polyacetals, as described in U.S. Pat. No. 5,354,643, or poly-N,O-acetals, as described in U.S. Pat. No. 5,498,506, in combination with an alkali-soluble polymer, and also in combination with a polymer having acid-labile groups that increase the solubility of the resist film in the developer after exposure, or in a combination of the two types of polymer described.

In the compositions according to the invention the content of solubility inhibitor is from about 3 to 55% by weight, especially from about 5 to 45% by weight, preferably from 10 to 35% by weight, based on the solids content, when solubility inhibitors having acid-labile groups are used in combination with alkali-soluble polymers and/or polymers having acid-labile groups.

Preferably soluble polymers (a5) are used in the compositions according to the invention in an aqueous-alkaline solution. Examples thereof include novolak resins, hydrogenated novolak resins, acetonepyrogallol resins, poly(o-hydroxystyrene), poly(m-hydroxystyrene), poly(p-hydroxystyrene), hydrogenated poly(hydroxystyrenes), halo- or alkyl-substituted poly(hydroxystyrenes), hydroxystyrene/N-substituted maleimide copolymers, o-/p- and m/p-hydrooxystyrene copolymers, partially o-alkylated poly(hydroxystyrenes), [e.g. o-methylated, o-(1-methoxy)ethylated, o-(1-ethoxy) ethylated, o-2-tetrahydropyranylated and o-(tert-butoxycarbonyl)methylated poly(hydroxystyrenes) having a substitution proportion of about from 5 to 30 mol % of hydroxyl groups], o-acylated poly(hydroxystyrenes) [e.g. o-acetylated and o-(tertbutoxy)carbonylated poly(hydroxystyrenes) having a substitution proportion of about from 5 to 30 mol % of hydroxyl groups], styrene/maleic acid anhydride copolymers, styrene/hydroxystyrene copolymers, α-methylstyrene/ hydroxystyrene copolymers, carboxylated methacrylic resins, and derivatives thereof. Also suitable are poly(meth) acrylic acid [e.g. poly(acrylic acid)], (meth)acrylic acid/ (meth)acrylate copolymers [e.g. acrylic acid/-methyl acrylate copolymers, methacrylic acid/methyl methacrylate copolymers or methacrylic acid/methyl methacrylate/tert-butyl methacrylate copolymers], (meth)acrylic acid/alkene copolymers [e.g. acrylic acid/ethylene copolymers], (meth)acrylic acid/(meth)-acrylamide copolymers [e.g. acrylic acid/acrylamide copolymers], (meth)acrylic acid/vinyl chloride copolymers [e.g. acrylic acid/vinyl chloride copolymers], (meth) acrylic acid/vinyl acetate copolymers [e.g. acrylic acid/vinyl acetate copolymers], maleic acid/vinyl ether copolymers [e.g. maleic acid/methyl vinyl ether copolymers], maleic acid monoester/methyl vinyl ester copolymers [e.g. maleic acid monomethyl ester/methyl vinyl ether copolymers], maleic acid/(meth)acrylic acid copolymers [e.g. maleic acid/acrylic acid copolymers or maleic acid/methacrylic acid copolymers], maleic acid/(meth)acrylate copolymers [e.g. maleic acid/methyl acrylate copolymers], maleic acid/vinyl chloride copolymers, maleic acid/vinyl acetate copolymers and maleic acid/alkene copolymers [e.g. maleic acid/ethylene copolymers and maleic acid/1-chloropropene copolymers].

The polymers suitable for the compositions according to the invention are in no way limited, however, to the examples given above.

Especially preferred as alkali-soluble polymers (a5) are novolak resins, poly(m-hydroxystyrene), poly(p-hydroxystyrene), copolymers of the corresponding hydroxystyrene monomers, for example with p-vinylcyclohexanol, alkyl-substituted poly(hydroxystyrenes), partially o- or m-alkylated and o- or m-acylated poly(hydroxystyrenes), styrene/hydroxystyrene copolymer and α-methylstyrene/hydroxystyrene copolymers. The novolak compounds are obtainable, for example, by addition condensation reactions of one or more monomers as main constituent(s) with one or more aldehydes in the presence of an acid catalyst.

Examples of monomers that are suitable for the preparation of alkali-soluble resins are hydroxylated aromatic compounds, such as phenol, cresols, that is to say m-cresol, p-cresol and o-cresol, dimethylphenols (xylenols), e.g. 2,5-dimethylphenol, 3,5-dimethylphenol, 3,4-dimethylphenol and 2,3-dimethylphenol, alkoxyphenols, e.g. p-methoxyphenol, m-methoxyphenol, 3,5-dimethoxyphenol, 2-methoxy-4-methylphenol, m-ethoxyphenol, p-ethoxyphenol, m-propoxyphenol, p-propoxyphenol, m-butoxyphenol and p-butoxyphenol, dialkylphenols, e.g. 2-methyl-4-isopropylphenol, and other hydroxylated aromatic compounds including mchlorophenol, p-chlorophenol, o-chlorophenol, dihydroxybiphenyl, bisphenol-A, phenylphenol, resorcinol and naphthene. Such compounds can be used alone or in mixtures of two or more. The monomers for novolak resins are not limited to the examples mentioned above.

Suitable examples of aldehydes for polycondensation with phenolic compounds in the preparation of novolaks are formaldehyde, p-formaldehyde, acetaldehyde, propionaldehyde, benzaldehyde, phenylacetaldehyde, α-phenylpropionaldehyde, β-phenylpropion-aldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenz-aldehyde, m-nitrobenzaldehyde, o-methylbenzaldehyde, m-methylbenzaldehyde, p-methylbenzaldehyde, p-ethylbenzaldehyde, p-, n-butylbenzaldehyde, furfural, chloroacetaldehyde and acetals derived therefrom, such as chloroacetaldehyde diethyl acetal. Preference is given to formaldehyde.

Those aldehydes can be used alone or in a combination of two or more. Examples of suitable acid catalysts include hydrochloric acid, sulfuric acid, formic acid, acetic acid and oxalic acid.

The average molecular weight of the resulting novolaks is advantageously in the range of about from 1000 to 30 000, preferably about from 2000 to 20 000.

The poly(hydroxystyrenes), and derivatives and copolymers thereof, as described above as alkali-soluble polymers (other than novolak resins), advantageously have average molecular weights of from about 2000 or higher, especially from 4000 to 200 000, preferably from 5000 to 50 000. When a polymer film having improved heat-resistance is to be produced, the average molecular weight is advantageously at least 5000 or more.

In the context of the present invention, the term "average molecular weight" is to be understood as the molar mass determined by gel permeation chromatography (calibrated with polystyrene standard).

In the compositions according to the invention, the alkali-soluble polymers can be used in mixtures of two or more.

Advantageously, the proportion of alkali-soluble polymer is up to 80% by weight, especially up to 60% by weight, preferably up to 40% by weight, based on the solids content of the formulation (i.e. excluding solvent) when there is used a mixture of alkali-soluble polymer and a polymer that contains groups that decompose under the action of an acid in order to increase the solubility in an alkaline developer solution.

When an alkali-soluble polymer is used together with a solubility inhibitor, without a polymer that has groups that decompose under the action of an acid, the proportion of alkali-soluble polymer is advantageously from 40 to 90% by weight, especially from 50 to 85% by weight, preferably from 60 to 80% by weight.

The proportion of compounds of formula I, II, III and IV (component(b)) in the positive resist formulation is advantageously from about 0.01 to 20% by weight, based on the solids content in the photoresist.

The use of the sulfonium salts of formula I, II, III and IV in chemically enhanced systems based on the principle of the removal of protecting groups from a polymer normally results in a positive resist. Positive resists are preferred to negative resists in many applications, especially because of their better resolution. There is, however, also interest in producing negative images using the positive resist mechanism, in order to combine the advantages of the good resolution of the positive resist with the properties of a negative resist. This is effected, for example, by the introduction of a so-called image-reversal step, as described, for example, in EP 361906. For that purpose, the resist material, after image-wise exposure, is treated, for example, with a gaseous base, before development, the acid that is formed being neutralised image-wise. The entire resist is then exposed and subjected to thermal treatment, and the negative image is developed in the customary manner.

Acid-sensitive components that form negative resists are generally compounds that are capable of undergoing a crosslinking reaction with themselves and/or with one or more further components in the composition when they are catalysed by an acid (e.g. the acid formed by exposure of the compounds of formula I, II, III, IV according to the invention). Compounds of that kind are, for example, the known acid-curable resins, such as acrylate, polyester, alkyd, melamine, urea, epoxy and phenolic resins or mixtures thereof. Amino resins, phenolic resins and epoxy resins are especially suitable. Acid-curable resins of that kind are generally known and are described, for example, in "Ullmann's Encyclopädie der technischen Chemie", Edition 4, Vol. 15 (1978), pp. 613-628. The crosslinking components should advantageously be present in a concentration of about from 2 to 40% by weight, preferably from 5 to 30% by weight, based on the solids content of the negative resist formulation.

The invention accordingly also includes a chemically enhanced negative photoresist that can be developed in an alkaline medium, which negative photoresist comprises
(a6) an alkali-soluble resin as crosslinking component,
(a7) a component that undergoes a crosslinking reaction with itself and/or with the crosslinking component under the action of acid, and
(b) as photosensitive acid donor a compound of formula I.

The composition may comprise, in addition to component (b), further photosensitive acid donors and/or further additives (c), and photosensitisers (d). Suitable components (c) and (d) have been described above.

There come into consideration as component (a7) the compounds given above in the description of component (a1).

Especially preferred acid-curable resins (a7) are amino resins, such as non-etherified or etherified melamine, urea, guanidine or biuret resins, especially methylated melamine resins or butylated melamine resins, suitable glycolurils (tetrahydroimidazo[4,5-d]imidazole-2,5-(1H,3H)-diones) and urones. In this context, the term "resin" means both customary technical mixtures that generally also include oligomers, and pure and high-purity compounds. N-Hexa(methoxymethyl)melamine and tetramethoxymethylglucoril, and N,N'-dimethoxymethylurone are the preferred acid-curable resins.

The concentration of the compound of formula I, II, III or IV in the negative resist is advantageously from about 0.1 to 30% by weight, especially up to 20% by weight, preferably from 1 to 15% by weight, based on the total solids content of the compositions.

The negative resist compositions may optionally comprise a film-forming polymeric crosslinking agent (binder) (a6). This will preferably be an alkali-soluble phenolic resin. Also highly suitable for that purpose are, for example, novolaks derived from an aldehyde, e.g. acetaldehyde or furfuraldehyde, especially from formaldehyde, and from a phenol, e.g. unsubstituted phenol, mono- or di-chlorosubstituted phenol, such as p-chloro-phenol, phenol mono- or di-substituted by $C_1$-$C_9$alkyl, such as o-, m- or p-cresol, the various xylenols, p-tert-butylphenol, p-nonylphenol, p-phenylphenol, resorcinol, bis(4-hydroxy-phenyl)methane or 2,2-bis(4-hydroxyphenyl)propane. Also suitable are homo- and co-polymers based on ethylenically unsaturated phenols, e.g. homopolymers of vinyl- and 1-propenyl-substituted phenols, such as p-vinylphenol or p-(1-propenyl)phenol or copolymers of those phenols with one or more ethylenically unsaturated compounds, e.g. styrenes. The proportion of crosslinking agent is generally within a range of about from 30 to 95% by weight, especially from 40 to 80% by weight.

An especially preferred negative resist formulation comprises from 0.5 to 15% by weight of a compound of formula I (component (b)), from 40 to 99% by weight of a phenolic resin as crosslinking agent (component (a6)), and from 0.5 to 30% by weight of a melamine resin (component (a7)), the percentages relating to the total solids content of the formulation.

Compounds of formula I, II, III and IV can also be used as acid donors that can be activated photochemically for the crosslinking of, for example, poly(glycidyl)methacrylates in negative resist systems. Such crosslinking reactions are disclosed, for example, by Chae et al. in Pollimo 1993, 17(3), 292.

The positive and negative photoresist formulations may comprise, in addition to component (b), further photosensitive acid donors (b1), further additives (c), sensitisers (d) and/or other photoinitiators (e).

The invention accordingly also relates to chemically enhanced resist compositions, as described above, that comprise, in addition to components (a1) or (a2) and (b), or components (a3), (a4), (a5) and (b), or components (a6), (a7) and (b), further additives (c), further photosensitive acid donors (b1), other photoinitiators (e), and/or sensitisers (d).

The compounds of formula I, II, III and IV can be used in the compositions according to the invention in combination with further known photolatent acid donors (b1), such as, for example, further onium salts, 6-nitrobenzylsulfonates, bis-sulfonyldiazomethane compounds, oxime sulfonates, etc. Examples of known photolatent acids for chemically enhanced photoresists are to be found, for example, in U.S. Pat. No. 5,731,364, U.S. Pat. No. 5,800,964, EP 704762, U.S. Pat. No. 5,468,589, U.S. Pat. No. 5,558,971, U.S. Pat. No. 5,558,976 and especially EP 794457 and EP 795786.

When mixtures of compounds of formula I, II, III and IV (b) with other photolatent acids (b1) are used, the ratio of (b) to (b1) is, for example, from 1:99 to 99:1.

The amount of photolatent acid in the formulations as given above refers to the whole contents of photolatent acid, i.e. (b)+(b1), if an additional photolatent acid (b1) is present.

Examples of suitable photolatent acids (b1) include the examples of cationic photoinitiators and acid-formers as given above and (1) onium salt compounds, e.g.
further iodonium salts, sulfonium salts, phosphonium salts, diazonium salts, pyridinium salts. Preference is given to diphenyliodonium triflate, diphenyliodonium pyrenesulfonate, diphenyliodonium dodecylphenylsulfonate, triphenylsulfonium triflate, triphenylsulfonium hexafluoroantimonate, diphenyliodonium hexafluoroantimonate, triphenylsulfonium naphthalenesulfonate, (hydroxyphenyl) benzylmethylsulfonium toluoylsulfonate, etc.

(2) halogen-containing compounds
haloalkyl-group-containing heterocyclic compounds, haloalkyl-group-containing hydrocarbon compounds, etc. Preference is given to (trichloromethyl)-s-triazine derivatives, such as phenyl-bis(trichloromethyl)-s-triazine, methoxyphenyl-bis(trichloromethyl)-s-triazine, naphthyl-bis (trichloromethyl)-s-triazine, etc.; 1,1-bis(4-chlorophenyl)-2, 2,2-trichloroethane, etc.;

(3) sulfone compounds, e.g.
β-ketosulfones, β-sulfonylsulfones and α-diazo derivatives thereof, etc. Preference is given to phenacylphenylsulfone, mesitylphenacylsulfone, bis(phenylsulfonyl)methane, bis (phenylsulfonyl)diazomethane.

(4) sulfonate compounds, e.g.
alkylsulfonic acid esters, haloalkylsulfonic acid esters, arylsulfonic acid esters, iminosulfonates, imidosulfonates, etc. Preference is given to imidosulfonates, e.g. N-(trifluoro-methylsulfonyloxy)succinimide, N-(trifluoromethylsulfonyloxy)phthalimide, N-(trifluoro-methylsulfonyloxy)naphthylimide, N-(trifluoromethylsulfonyloxy)diphenylmaleimide, N-(tri-fluoromethylsulfonyloxy)-bicyclo-[2.2.1]-hept-5-ene-2,3-dicarboximide, N-(trifluoromethylsulfonyloxy)-7-oxabicyclo-[2.2.1]-hept-5-ene-2,3-dicarboximide, N-(trifluoromethyl-sulfonyloxy)-7-oxabicyclo-[2.2.1]-hept-5-ene-2,3-dicarboximide, N-(trifluoromethylsulfonyl-oxy)-bicyclo-[2.2.1]-heptan-5,6-oxy-2,3-dicarboximide, N-(camphanylsulfonyloxy)suc-cinimide, N-(camphanylsulfonyloxy)phthalimide, N-(camphanylsulfonyloxy)naphthylimide, N-(camphanylsulfonyloxy)diphenylmaleimide, N-(camphanylsulfonyloxy)bicyclo-[2.2.1]-hept-5-ene-2,3-dicarboximide, N-(camphanylsulfonyloxy)-7-oxabicyclo-[2.2.1]-hept-5-ene-2,3-dicarboximide, N-(camphanylsulfonyloxy)-7-oxabicyclo-[2.2.1]hept-5-ene-2,3-dicarboximide, N-(camphanylsulfonyloxy)-bicyclo-[2.2.1]-heptan-5, 6-oxy-2,3-dicarboximide, N-(4-methylphenylsulfonyloxy) succinimide, N-(4-methylphenylsulfonyloxy)phthal imide, N-(4-methylphenylsulfonyloxy)naphthyl imide, N-(4-methylphenylsulfonyloxy)naphthylimide, N-(4-methylphenylsulfonyloxy)diphenylmaleimide, N-(4-methylphenylsulfonyloxy)-bicyclo-[2.2.1]-hept-5-ene-2,3-dicarboximide, N-(4-methylphenylsulfonyloxy)-7-oxabicyclo-[2.2.1]-hept-5-ene-2,3-dicarboximide, N-(4-methylphenylsulfonyloxy)-bicyclo-[2.2.1]-heptan-5,6-oxy-2,3-dicarboximide, N-(2-trifluoromethylphenylsulfonyloxy)succinimide, N-(2-trifluoromethylphenylsulfonyloxy)naphthyl imide, N-(2-trifluoromethylphenylsulfonyloxy)diphenylmaleimide, N-(2-trifluoromethyl phenylsulfonyloxy)-bicyclo-[2.2.1]-hept-5-ene-2,3-dicarboximide, N-(2-trifluoromethylphenylsulfonyloxy)-7-oxabicyclo-[2.2.1]-hept-5-ene-2,3-dicarboximide, N-(2-trifluoromethylphenylsulfonyloxy)-bicyclo-[2.2.1]-heptan-5,6-oxy-2,3-dicarboximide, etc. Further suitable sulfonate compounds are, for example, benzoin tosylate, pyrogallol tristriflate, pyrogallolmethanesulfonic acid triester, nitrobenzyl-9,10-diethyloxyanthracyl-2-sulfonate, α-(4-toluenesulfonyloxyimino)-benzyl cyanide, α-(4-toluenesulfonyloxyimino)-4-methoxybenzyl cyanide, α-(4-toluene-sulfonyloxyimino)-2-thienylmethyl cyanide, α-(methylsulfonyloxyimino)-1-cyclohexenylacetonitrile, α-(butylsulfonyloxyimino)-1-cyclopentenyl-acetonitrile, (4-methylsulfonyloxyimino-cyclohexa-2,5-dienylidene)-phenyl-acetonitrile, (5-methylsulfonyloxyimino-5H-thiophen-2-ylidene)-phenyl-acetonitrile, (5-methylsulfonyloxyimino-5H-thiophen-2-ylidene)-(2-methylphenyl)-acetonitrile, (5-methylsulfonyloxyimino-5H-thiophen-2-ylidene)-(2-chlorophenyl)-acetonitrile, etc.

In the compositions according to the invention, special preference is given to sulfonate compounds, such as pyrogallolmethanesulfonic acid triester, N-(trifluoromethyl-sulfonyloxy)bicyclo-[2.2.1]-hept-5-ene-2,3-dicarboximide, N-(camphanylsulfonyloxy)-naphthylimide, N-(2-trifluoromethyl phenylsulfonyloxy)phthalimide, N-(trifluoromethyl-sulfonyloxy)-bicyclo-[2.2.1]-hept-5-ene-2,3-dicarboximide, N-(camphanylsulfonyloxy)-naphthylimide, N-(2-trifluoromethylphenylsulfonyloxy)phthalimide, etc.

(5) quinonediazide compounds,
e.g. 1,2-quinonediazidesulfonic acid ester compounds of polyhydroxy compounds. Preference is given to compounds having a 1,2-quinonediazidesulfonyl group, e.g. a 1,2-benzoquinonediazide-4-sulfonyl group, a 1,2-naphthoquinonediazide-4-sulfonyl group, a 1,2-naphthoquinonediazide-5-sulfonyl group, a 1,2-naphthoquinonediazide-6-sulfonyl group, etc. Special preference is given to compounds having a 1,2-naphthoquinonediazide-4-sulfonyl group or a 1,2-naphthoquinonediazide-5-sulfonyl group. Especially suitable are 1,2-quinonediazidesulfonic acid esters of (poly) hydroxyphenylarylketones, such as 2,3,4-trihydrooxybenzophenone, 2,4,6-trihydroxybenzophenone, 2,3,4,4'-tetrahydroxybenzo-phenone, 2,2',3,4-tetrahydroxybenzophenone, 2,3,4,4'-tetrahydroxybenzophenone, 2,2',4, 4'-tetrahydroxybenzophenone, 2,2',3,4,4'-pentahydroxybenzophenone, 2,2',3,2,6'-pentahydroxybenzophenone, 2,3,3',4, 4',5'-hexahydroxybenzophenone, 2,3',4,4',5',6-hexahydroxybenzophenone, etc.; 1,2-quinonediazidesulfonic acid esters of bis[(poly)-hydroxyphenyl]alkanes, such as bis(4-hydroxyphenyl) ethane, bis(2,4-dihydroxyphenyl)-ethane, 2,2-bis(4- hydroxyphenyl)propane, 2,2-bis(2,4-dihydroxyphenyl)propane, 2,2-bis(2,3,4-trihydroxyphenyl)propane, etc.; 1,2-quinonediazidesulfonic acid esters of (poly)hydroxyphenylalkanes, such as 4,4'-dihydroxytriphenylmethane, 4,4',4"-trihydroxy-triphenylmethane, 4,4',5,5'-tetramethyl-2,2',2"-trihydroxytriphenylmethane, 2,2,5,5'-tetramethyl-4,4',4"-trihydroxytriphenylmethane, 1,1,1-tris(4-hydroxyphenyl)ethane, 1,1-bis(4-hydroxyphenyl)-1-phenylethane, 1,1-bis(4-hydroxyphenyl)-1-(4-[1-(hydroxyphenyl)-1-methylethyl]phenyl)ethane, etc; 1,2-quinonediazidesulfonic acid esters of (poly)hydroxy-phenylflavanes, such as 2,4,4-trimethyl-2',4',7-trihydroxy-2-phenylflavane, 2,4,4-trimethyl-2',4',5',6,7-pentahydroxy-2-phenylflavane, etc.

Further suitable additives (c) are as described above.

Further examples of basic organic compounds that can be used in the resist compositions according to the present invention are compounds that are stronger bases than phenol, especially nitrogen-containing bases. Such compounds may be ionic, such as tetraalkyl-ammonium salts, or non-ionic. Preference is given to nitrogen-containing bases that, per molecule, have two or more nitrogen atoms in different chemical environments. Special preference is given to compounds comprising at least one substituted or unsubstituted amino group and at least one nitrogen-containing ring structure, as well as to compounds having at least one alkylamino group. Examples thereof include guanidine, aminopyridine, aminoalkylpyridines, aminopyrrolidine, indazole, imidazole, pyrazole, pyrazine, pyrimidine, purine, imidazoline, pyrazoline, piperazine, aminomorpholine and aminoalkylmorpholines. Both the unsubstituted and the substituted derivatives thereof are suitable. Preferred substituents are amino groups, aminoalkyl groups, alkylamino groups, aminoaryl groups, aryl-amino groups, alkyl groups, alkoxy groups, acyl groups, acyloxy groups, aryl groups, aryloxy groups, nitro, hydroxy and cyano. Specific examples of especially preferred basic compounds are guanidine, 1,1-dimethylguanidine, 1,1,3,3-tetramethylguanidine, 2-amino-pyridine, 3-aminopyridine, 4-aminopyridine, 2-dimethylaminopyridine, 4-dimethylamino-pyridine, 2-diethylaminopyridine, 2-(aminomethyl)pyridine, 2-amino-3-methylpyridine, 2-amino-4-methylpyridine, 2-amino-5-methylpyridine, 2-amino-6-methylpyridine, 3-amino-ethyl pyridine, 4-aminoethyl pyridine, 3-aminopyrrolidine, piperazine, N-(2-aminoethyl)-piperazine, N-(2-aminoethyl)piperidine, 4-amino-2,2,6,6-tetramethylpiperidine, 4-piperidinopiperidine, 2-iminopiperidine, 1-(2-aminoethyl)pyrrolidine, pyrazole, 3-amino-5-methylpyrazole, 5-amino-3-methyl-1-p-tolylpyrazole, pyrazine, 2-(aminomethyl)-5-methyl-pyrazine, pyrimidine, 2,4-diaminopyrimidine, 4,6-dihydrooxypyrimidine, 2-pyrazoline, 3-pyrazoline, N-aminomorpholine and N-(2-aminoethyl)morpholine.

Other examples can be found in DE 4408318, U.S. Pat. No. 5,609,989, U.S. Pat. No. 5,556,734, EP 762207, DE 4306069, EP 611998, EP 813113, EP 611998 and U.S. Pat. No. 5,498,506. The basic compounds suitable for the compositions according to the invention are not limited, however, to those described above.

The nitrogen-containing basic compounds may be used alone or in a combination of two or more. The proportion of those compounds is generally about from 0.001 to 10 parts by weight, especially from 0.01 to 5 parts by weight, per 100 parts by weight of the photosensitive composition according to the invention (without the solvent).

The composition may also comprise an organic basic compound that decomposes under the action of actinic radiation ("suicide base"), as described, for example, in EP 710885, U.S. Pat. No. 5,663,035, U.S. Pat. No. 5,595,855, U.S. Pat. No. 5,525,453 and EP 611998.

Suitable examples of dyes (c) are those mentioned above as well as oil-soluble dyes and basic dyes, e.g. Oil Yellow #101, Oil Yellow #103, Oil Pink #312, Oil Green BG, Oil Blue BOS, Oil Blue #603, Oil Black BY, Oil Black BS, Oil Black T-505 (all from Orient Chemical Industries Ltd., Japan), crystal violet (CI 42555), methyl violet (CI 42535), rhodamine B (CI 45170B), malachite green (CI 42000) and methylene blue (CI 52015).

Examples of sensitisers (d) are as described above and are, for example, p,p'-tetramethyldiaminobenzophenone, p,p'-tetraethylethylaminobenzophenone, anthrone, pyrene, perylene, phenothiazine, benzil, acridine orange, benzoflavin, cetoflavin T, 9,10-diphenylanthracene, 9-fluorenone, phenanthrene, acetophenone, 2-nitrofluorene, 5-nitroacenaphthene, benzoquinone, 2-chloro-4-nitroaniline, N-acetyl-p-nitroaniline, p-nitroaniline, N-acetyl-4-nitro-1-naphthylamine, picramide, anthraquinone, 2-ethylanthraquinone, 2-tert-butyl-anthraquinone, 1,2-benzanthraquinone, 3-methyl-1,3-diaza-1,9-benzanthrone, dibenzalacetone, 1,2-naphthoquinone, 3-acylcoumarin derivatives, 3,3'-carbonyl-bis(5,7-dimethoxycarbonyl-coumarin), 3-(aroylmethylene)thiazolines, eosin, rhodamine, erythrosin and coronene.

Suitable sensitisers are not, however, limited to those examples.

Such sensitisers can also be used as photoabsorbers for the absorption of specific UV rays emitted by light sources. In that case, the photoabsorber reduces the reflection of light from the substrate and lessens the effect of multiple reflection inside the resist film. This reduces the effect of standing waves.

Further suitable additives (c) are acid-amplifiers, compounds that accelerate the formation of acid or increase the acid concentration. Such compounds can be used in the resist compositions according to the invention, but can also be advantageous in other applications for the compositions according to the invention, such as in coatings. Examples of such compounds are described by Arimitsu, K. et al. in J. Photopolym. Sci. Technol. 1995, 8, p. 43ff.; by Kudo, K. et al. in J. Photopolym. Sci. Technol. 1995, 8, p. 45ff.; by W. Huang et al. in SPIE Vol. 3999, pp. 591-597 (2000) and by Ichimura, K. et al. in Chem: Letters 1995, p. 551ff.

Normally the compositions according to the invention are dissolved in a suitable solvent before application to the substrate. Examples of such solvents include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, 2-ethoxyethyl acetate, 2-ethoxyethanol, diethyl glycol dimethyl ether, ethylene glycol monoethyl ether acetate, propylene glycol monomethyl ether, propylene glycol monomethyl ether acetate, toluene, ethyl acetate, methyl lactate, ethyl lactate, methylmethoxy propionate, ethylethoxy propionate, methyl pyruvate, ethyl pyruvate, propyl pyruvate, N,N-dimethylformamide, dimethyl sulfoxide, N-methylpyrrolidone and tetrahydrofuran. Such solvents can be used individually or in combinations. Preferred examples thereof are esters, such as 2-methoxyethyl acetate, ethylene glycol monoethyl ether acetate, propylene glycol monomethyl ether acetate, methylmethoxy propionate, ethylethoxy propionate and ethyl lactate.

A surfactant may be added to the solvent. Examples of suitable surfactants are non-ionic surfactants, such as polyoxyethylene alkyl ethers, e.g. polyoxyethylene lauryl ether, polyoxyethylene stearyl ether, polyoxyethylene acetyl ether and polyoxyethylene oleyl ether; polyoxyethylene alkyl aryl ethers, e.g. polyoxyethylene octyl phenol ether and polyoxyethylene nonyl phenol ether; polyoxyethylene/polyoxypropylene block copolymers, sorbitol/fatty acid esters, e.g. sorbitol monolaurate, sorbitol monopalmitate, sorbitol monostearate, sorbitol monooleate, sorbitol trioleate; fluorochemical surfactants, such as F-top EF301, EF303 and EF352 (New Akita Chemical Company, Japan), Megafac F171 and F17.3 (Dainippon Ink & Chemicals, lnc. Japan), Fluorad FC 430 and FC431 (Sumitomo #3M Ltd., Japan), Asahi Guard AG710 and Surflon S-382, SC101, SC102, SC103, SC104, SC105 and SC106 (Asahi Glass Col, Ltd., Japan); organosiloxane polymer KP341 (Shin-Etsu Chemical Co., Ltd., Japan); and acrylic or methacrylic (co)polymers Poly-flow Now. 75 and N0.95 (Kyoeisha Chemical Co., Ltd., Japan). Generally the proportion of surfactant in the composition is about 2 parts by weight or less, e.g. 0.1 part by weight or less, per 100 parts by weight of solids content in the composition. The surfactants may be used individually or in combinations.

The solution of the composition according to the invention is applied uniformly to a substrate by means of generally known methods already described above. Suitable layer thicknesses have also already been indicated above.

After coating, the solvent is usually removed by heating and a layer of the photoresist remains on the substrate. The drying temperatures must, of course, be lower than the temperatures at which constituents of the resist formulation can decompose or react. Normally the drying temperatures vary within a range of about from 60 to 160° C.

The exposure of the coated substrates has already been described above.

After exposure and, if necessary after the thermal treatment, the exposed sites of the composition (in the case of the positive resist) or the non-exposed sites of the composition (in the case of the negative resist) are removed using a developer in a manner generally known to a person skilled in the art.

In order to accelerate the catalytic reaction and thus to ensure the development of a sufficient difference in solubility between exposed and non-exposed areas of the resist coating, the coating is preferably heated before development. It is also possible to carry out heating during the exposure. Generally temperatures of from 60 to 160° C. are used. The optimum duration of heating depends upon the heating method used and can be determined by the person skilled in the art by simple experiments. It normally ranges from a few seconds to several minutes, e.g. from 10 to 300 seconds when a heating plate is used, and, e.g., from 1 to 30 minutes when a circulated-air oven is used.

Development is then carried out, wherein the portions of the coating that are soluble in the developer are removed. If necessary, the development step can be accelerated by gentle movement of the sample, careful brushing of the coating in the developer bath or by development in a spray developing apparatus. Aqueous-alkali developer fluids customary in the art can be used for that purpose. Examples thereof include sodium and potassium hydroxyide, the corresponding carbonates, hydrogen carbonates, silicates and metasilicates, metalfree bases, such as ammonium compounds, or amines, such as ethylamine, n-propylamine, diethylamine, di-n-propylamine, triethylamine, methyldiethylamine, alkanolamines, e.g. dimethylethanolamine, triethanolamine, quaternary ammonium hydroxides, e.g. tetramethylammonium hydroxide or tetraethylammonium hydroxide. The developer solutions are normally up to 0.5N, but are generally diluted before use in a suitable manner. For example, solvents having a normality of about from 0.1 to 0.3 are very suitable. The choice of developer will depend upon the nature of the photocurable coating, especially upon the nature of the crosslinking agent or the resulting photolysis products. The aqueous developer solutions may, if necessary, also comprise small amounts of wetting agents and/or organic solvents. Examples of typical organic solvents that may be added to the developer solutions include cyclohexanone, 2-ethoxyethanol, toluene, acetone, isopropanol and mixtures of two or more such solvents. A typical aqueous/organic developer system is a system based on Butylcellosolve®/water.

The invention relates also to a method of manufacturing a photoresist by
(1) applying a composition as described above to a substrate;
(2) heating the composition to a temperature of from 60° C. to 160° C.;
(3) carrying out image-wise exposure with light of a wavelength of from 150 nm to 1500 nm;
(4) optionally heating the composition to temperatures of from 60° C. to 160° C.; and
(5) subsequently developing with a solvent or an aqueous alkaline developer.

The photoresist compositions can be used on all types of substrate and with all irradiation techniques known to the person skilled in the art. For example, semiconductor substrates can be used, such as silicon, gallium arsenide, germanium, indium antimonide; also substrates covered by oxide or nitride layers, such as silicon dioxide, silicon nitride, titanium nitride, siloxanes, and metal substrates and metal-coated substrates coated with metals such as aluminium, copper, tungsten, etc. The substrate can also be coated with polymeric materials, for example with organic antireflective coatings, insulation layers and dielectric coatings made of polymeric materials.

The photoresist layer can be irradiated by all customary techniques, such as direct writing, i.e. with a laser beam or projection lithography in step- and repeat mode or scanning mode, or by contact printing through a mask.

In the case of projection lithography, a large number of optical conditions can be selected, such as coherent, partially coherent or incoherent radiation. This includes non-axial irradiation techniques, for example annular illumination and quadrupolar irradiation where the radiation is allowed to pass through only certain regions of the lens, excluding the centre of the lens.

The mask used to produce the pattern can be a hard mask or a flexible mask. The mask can include transparent, semitransparent and opaque patterns. The pattern size can include also patterns that are at or below the resolution limit of the projection optics and are arranged on the mask in a certain manner in order to modify the aerial image, intensity and phase modulation of the radiation after having it has passed through the mask. This includes phase-shift masks and halftone phase-shift masks.

The process for forming an image on the photoresist composition can be used to generate patterns of any desired geometry and shape, for example dense and isolated lines, contact holes, channels, incisions, dots, etc.

Preference is given to a method wherein the image-wise exposure is effected by monochromatic or polychromatic radiation in the wavelength range of from 190 to 450 nm, especially from 190 to 260 nm.

The invention relates also to the use of compounds of formula I, II, III and IV as described above as photolatent acid donors in the polymerisation or crosslinking of cationically or acid-catalytically polymerisable or crosslinkable compounds or to increase the solubility of compounds that increase their solubility in a developer under the action of acid, and also to a method for the photopolymerisation or crosslinking of cationically or acid-catalytically polymerisable or crosslinkable compounds under the action of electromagnetic radiation, in which method a compound of formula I is used as photolatent acid donor.

A further subject of the invention is a method as described above in the manufacture of surface-coating compositions including scratch-resistant coatings, stain-resistant coatings, anti-fog coatings, stain resistant coatings, anticorrosion coatings, powder coating compositions, printing inks, non impact printing inks including ink jet printing inksprinting plates, dental compounds including composites, stereolithography resins, adhesives, anti-adhesive coatings (release coatings), conformal coatings, optical fiber coatings, colour filters, resist materials or image-recording materials including holography resins.

The composition according to the present invention, comprising a cationic photoinitiator of the formula I, II, III or IV may also be employed in a vacuum deposition process as described in WO 02/064268. That is, the photoinitiators are suitable to be flash-evaporated vacuum-deposited. Accordingly, in a process for forming a solid poylmeric structure from flash-evaporated vacuum-deposited cationically curable monomeric material, comprising the steps (i) preparing a mixture of a cationically-curable monomer with a thermally stable, chemically inactive at room temperature, cationic photoinitiator;

(ii) flash-evaporating said mixture in a vacuum to produce a vapor;

(iii) condensing the vapor to produce a film; and (iv) exposing said film to a radiation source to produce a polymeric solid film, said photoinitiator is of the formula I, II, III or IV as described above.

Suitable apparatus for said procedure, as well as details concerning the monomers are described in WO 02/064268, the teachings of which are incorporated by reference.

The UV irradiation to release the acid is generally effected with light of a wavelength of from 157 to 600 nm. Suitable radiation is present, for example, in sunlight or light from artificial light sources. A large number of widely varying types of light source may be used. Point sources and also planiform radiators (lamp carpets) are suitable. Examples thereof include: carbon arc lamps, xenon arc lamps, medium-, high- and low-pressure mercury lamps, doped where appropriate with metal halides (metal halide lamps), microwave-excited metal vapour lamps, excimer lamps, superactinic fluorescent tubes, fluorescent lamps, argon incandescent lamps, flashlamps, photographic flood lights, light emitting diodes (LED), electron beams and X-rays.

The distance between the lamp and the substrate to be exposed can vary according to the intended use and the type and strength of the lamp and may be, for example, from 2 cm to 150 cm. Laser light sources, for example excimer lasers, are also suitable. Lasers in the visible range can also be used.

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case

EXAMPLE 1

Preparation of (4-isopropyl-phenyl)-(2-methoxycarbonyl-phenyl)-(4-phenoxyphenyl) sulfonium hexafluorophosphate

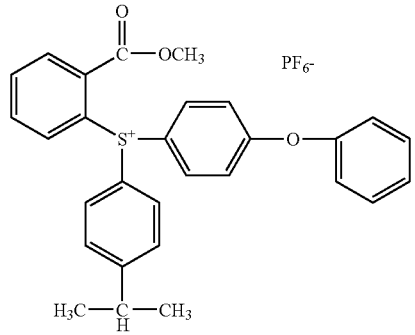

1.1: Dithiodibenzoic acid-dimethylester

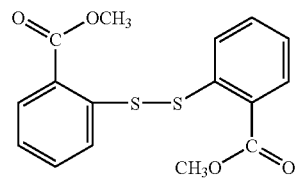

25 g (81.6 mmol) of dithiodibenzoic acid is refluxed in 60 ml of SOCl$_2$ and 1.5 ml of dimethylformamide (DMF) for 3 hrs. Then the excess of SOCl$_2$ is distilled off, and the residue is dissolved in CHCl$_3$ and added dropwise to a solution of methanol (50 ml) and triethylamine (0.204 mol) in CHCl$_3$ (300 l). After standing over night the reaction mixture is shaked with water and saturated K$_2$CO$_3$ solution. After drying the organic layer the solvent is evaporated and methanol is added to the residue (oil). 13.6 g (50%) of solid product is obtained.

1.2: 2-(4-Isopropyl-phenylsulfanyl)-benzoic acid methylester

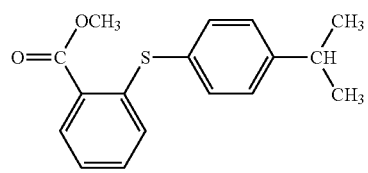

To 15 g (44.9 mmol) of dithidibenzoic acid dimethylester in 150 ml cumene are added 6.7 g=4.1 ml (50 mmol) of SO$_2$Cl$_2$ and the reaction mixture is stirred for 1 hour. Because there is some insoluble material, another 2 ml of SO$_2$Cl$_2$ are added and the reaction mixture is warmed to 60° C. (clear solution). To this mixture 27 g (200 mmol) of AlCl$_3$ are added in portions and the reaction mixture is stirred for 2 hrs and then poured to the ice/HCl. The organic layer is separated, dried over anhydrous Na$_2$SO$_4$ and concentrated. The residue is purified by column chromatography (isohexane-CH$_2$Cl$_2$/ 3:1-1:3) and 15.2 g (59%) of the desired sulfide are obtained.

1.3: 2-(4-Isopropyl-phenylsulfinyl)-benzoic acid methylester

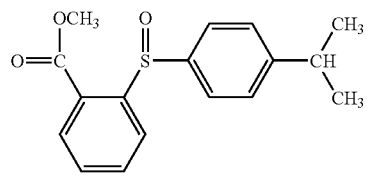

To 15 g (52.4 mmol) of the sulfide obtained according to example 1.2 in 60 ml of acetic acid 13.7 g (70 mmol) of 39% peroxoacetic acid are added. The mixture is stirred for 2 hrs and then poured into water. The mixture is extracted with dichloromethane (DM), the combined DM layers are washed with NaHCO$_3$, then dried and the solvent is evaporated. The crude product is purified by column chromatography (DM-ethylacetate/1:0 . . . 2:1). 8 g (56%) of the desired sulfoxide are obtained.

1.4: (4-Isopropyl-phenyl)-(2-methoxycarbonyl-phenyl)-(4-phenoxy-phenyl) sulfonium hexafluorophosphate To a mixture of 2 g (6.6 mmol) of the sulfoxide obtained according to example 1.3 and 1.7 g (9.9 mmol) of diphenylether are added 10 ml of freshly prepared P$_2$O$_5$/CH$_3$SO$_3$H reagent (prepared by dissolving P$_2$O$_5$ in CH$_3$SO$_3$H in a ratio of 1:10 at 50° C.). The reaction mixture is stirred at 40-45° C. for 3 hrs. After cooling to ambient temperature the mixture is poured into 200 ml of water, which is then extracted three times with 20 ml of DM. The combined DM layers are evaporated and the residue is dissolved in 20 ml of acetone. The acetone solution is mixed with an acetone solution of KPF$_6$ (3.7 g/19.8 mmol/KPF$_6$+100 ml acetone). The solid material is filtered off and to the acetone solution 250 ml of water are slowly added. After the evaporation of the acetone the residue is extracted three times with 20 ml of DM and the combined organic layers are concentrated. The residue is purified by column chromatography (ethylacetate-isohexane 2:1) and 2.7 g (68%) of the white product with m.p. 95-100° C. are obtained.

EXAMPLE 2

Preparation of (4-isopropyl-phenyl)-(2-methoxycarbonyl-phenyl)-(4-methoxyphenyl) sulfonium hexafluorophosphate

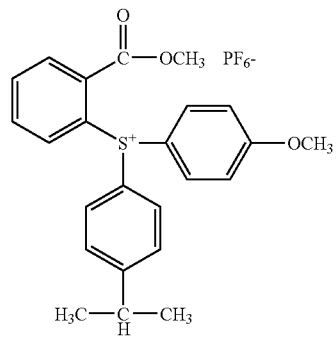

1.5 g of P$_2$O$_5$ and 15 ml of methanesulfonic acid are placed in a flask equipped with a magnetic stirrer and a CaCl$_2$ tube. The suspension is stirred at 50° C. and after 45 min. the P$_2$O$_5$ is dissolved. To the suspension at ambient temperature are added 3 g (9.9 mmol) of the corresponding sulfoxide (prepared according to the methods as described in example 1.1-1.3) and 1.2 g (11 mmol) of anisole and the reaction mixture is stirred at 40-45° C. for 3 hrs. The chilled mixture is then poured into 300 ml of water, which then is extracted four times with 30 ml of DM. The combined DM layers are evaporated and the residue is dissolved in 20 ml of acetone and mixed with an acetone solution of KPF$_6$ (100 ml acetone+ 5.55 g KPF$_6$, 30 mmol). The acetone is evaporated and the solid residue is suspended in 100 ml of water. The suspension is then extracted four times with 30 ml of DM. The solvent is evaporated and the product purified by column chromatography (ethylacetate/isohexane 2:1). 1.95 g (36.6%) of the white solid product having a m.p. of 75-85° C. are obtained.

EXAMPLES 3-24

The compounds of the examples 3-24 are obtained according to the method described in example 1, by employing the corresponding educts. The compounds and their physical data are collected in table 1.

TABLE 1

| Ex. | R$_1$ | Ar$_1$ |
|---|---|---|
| 3 | CH$_3$ | 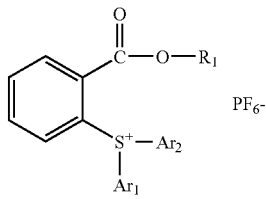 |

TABLE 1-continued
| | | |
|---|---|---|
| 4 | CH₃ | 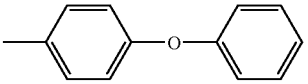 |
| 5 | CH₃ |  |
| 6 | CH₃ | 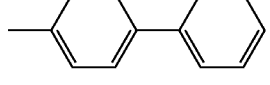 |
| 7 | H | 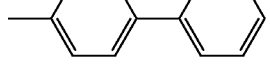 |
| 8 | H | 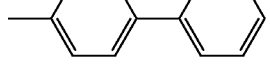 |
| 9 | C₅H₁₁ | 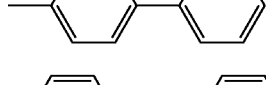 |
| 10 | CH₃ | 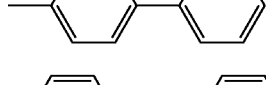 |
| 11 | CH₃ | 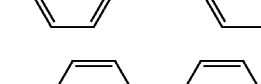 |
| 12 | 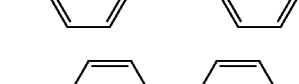 | 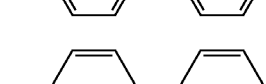 |
| 13 | CH₃ | 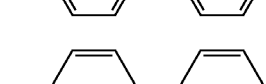 |
| 14 | CH₃ |  |
| 15 | (CH₂CH₂O)₁₂CH₃ | 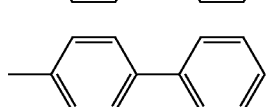 |
| 16 | C₆H₁₃ | 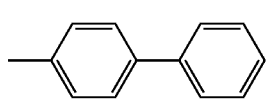 |
| 17 | 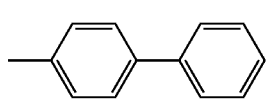 |  |
| 18 | CH₃ | 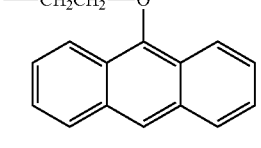 |

TABLE 1-continued
| Ex. | | Ar | |
|---|---|---|---|
| 19 | CH₃ | 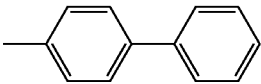 | |
| 20 | CH₃ | 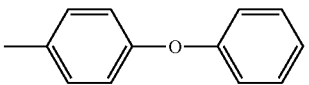 | |
| 21 | CH₃ | 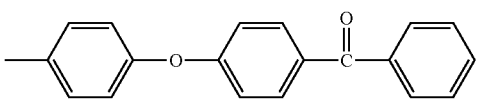 | |
| 22 | CH₃ | 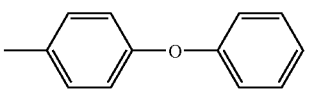 | |
| 23 | CH₃ | 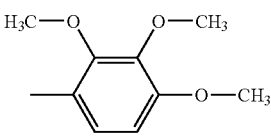 | |
| 24 | CH₃ | 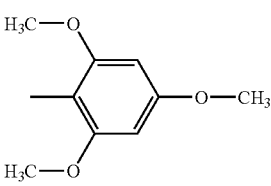 | |
| Ex. | Ar₂ | Aspect m.p. |
|---|---|---|
| 3 | 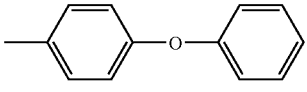 | White solid, 107-113° C. |
| 4 | 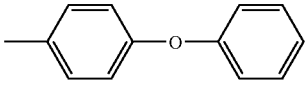 | White solid, 85-90° C. |
| 5 | 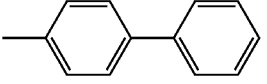 | White solid, 118-125° C. |
| 6 | 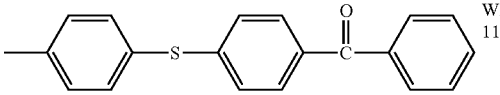 | White solid, 113-119° C. |
| 7 | 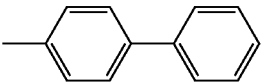 | Yellowish solid, 175-180° C. |
| 8 | 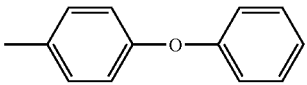 | White solid, 130-135° C. |
| 9 | 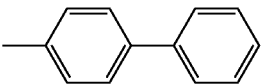 | White solid, 83-87° C. |
| 10 | 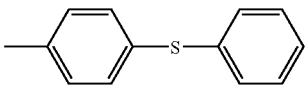 | White solid, 93-99° C. |

TABLE 1-continued

| # | Structure | Description |
|---|---|---|
| 11 | 4-methylphenyl-O-CH₂CH₂OH | Off-White solid 88-95° C. |
| 12 | 4-methylbiphenyl | White solid 121-124° C. |
| 13 | 4-methylphenyl-S-phenyl-C(=O)-phenyl | White solid, 94-100° C. |
| 14 | 4-methylphenyl-S-phenyl-C(=O)-phenyl | White solid, 80-85° C. |
| 15 | 4-methylbiphenyl | Yellowish viscous liquid |
| 16 | 4-methylbiphenyl | Yellow solid, 77-83° C. |
| 17 | 4-methylbiphenyl | Pinkish solid, 100-103° C. |
| 18 | 3-methyl-9-ethylcarbazole | Grey solid 125-135° C. |
| 19 | 4-methylphenyl-O-phenyl-C(=O)-phenyl | White solid, 103-110° C. |
| 20 | 4-methylphenyl-S-phenyl-C(=O)-phenyl | White solid, 93-99° C. |
| 21 | 4-methylphenyl-S-phenyl-C(=O)-phenyl | Cream solid 105-113° C. |
| 22 | 4-methylphenyl-O-phenyl-C(=O)-phenyl | Off-White solid 97-101° C. |
| 23 | 4-methylphenyl-S-phenyl-C(=O)-phenyl | White solid 89-94° C. |
| 24 | 4-methylphenyl-O-phenyl-C(=O)-phenyl | Pink solid 96-102° C. |

EXAMPLE 25

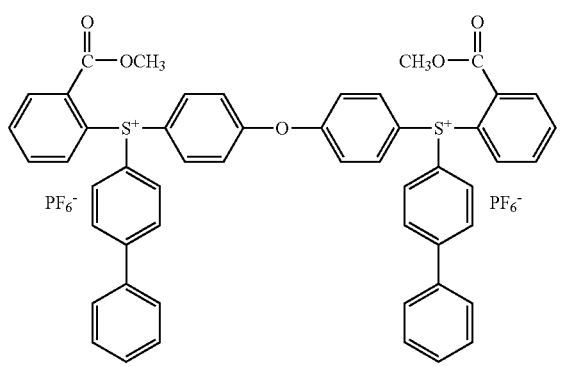

25.1: 2-(Biphenyl-4-sulfinyl)-benzoic acid methyl ester

To 10 g (30 mmol) of dithiodibenzoic acid—dimethylester (prepared according to example 1.1) and 5 drops of pyridine in 80 ml dichloromethane are added 2.7 ml (33 mmol) of $SO_2Cl_2$ and the reaction mixture is stirred for 2 hours at ambient temperature. Then 23 g of biphenyl are added, followed by 16 g of $AlCl_3$ by portions over 1 hr. keeping the temperature at 15-20° C. After stirring for 2 hrs at ambient temperature the mixture is poured onto a mixture of 500 ml $H_2O$+ice and 50 ml of conc. HCl. The organic layer is separated and the aqueous phase is extracted twice with dichloromethane (50 ml). The collected organic phases are dried and evaporated.

The residue (ca, 28 g) is dissolved in 150 ml acetic acid and 14.20 g of 39% of peroxoacetic acid (120% of theory) are added dropwise to this solution at 10-15° C. over 30 min. After stirring for 1 hr. at room temperature, the solvent is evaporated under reduced pressure. The residue is redissolved in ethylacetate, washed three times with water, dried and concentrated by evaporation. The crude product is purified by column chromatography (ethylacetate:isohexane=1:4), yielding 11.5 g of the title sulfoxide, which is suspended in 30 ml of diethylether, filtered off and dried. Yield: 10.41 g, pale yellow solid, m.p. 140-142° C.

25.2: (oxydi-4,1-phenylene)bis[biphenyl-(2-methoxycarbonyl-phenyl) sulfonium]hexafluorophosphate 2 g of $P_2O_5$ are dissolved in 20 ml of methanesulfonic acid at 45° C. over 1 hr. To this solution are added 3.36 g (10 mmol) of 2-(biphenyl-4-sulfinyl)-benzoic acid methyl ester and 1.7 g (10 mmol) diphenylether. The reaction mixture is stirred at 35° C. for 2 hrs. Then a further portion of 3.36 g (10 mmol) of the sulfoxide is added and the reaction mixture is stirred for 2.5 hrs at 45-50° C. The reaction mixture is then added dropwise to a solution of 7.36 g (40 mmol) $KPF_6$ in 300 ml of distilled water. The white solid material is filtered off and washed with distilled water (Thin layer chromatography on $SiO_2$ reveals the presence of two main products: the product with $R_f$=0.8 (dichloromethane:ethylacetate=8:2) is the monosubstitued diphenylether (product of example 3) and the second product ($R_f$=0.45) is the disubstituted diphenylether of the title. This mixture is separated by column chromathography ($CH_2Cl_2$:ethylacetate 10:1 to $CH_2Cl_2$:ethylacetate 10:3) to give 2.5 g of monosubstitued product of example 3 and 2.9 g of the disulfonium compound of the title as a colorless solid, mp. 155-160° C.

$^1$H NMR (DMSO, 300 MHz). (ppm): 3.92 (6H, s, —COOMe), 7.42-7.57 (12H, m, ArH), 7.77-7.88 (12H, m, ArH), 8.00-8.08 (8H, m, ArH), 8.36-8.40 (2H, m, ArH).

EXAMPLE 26

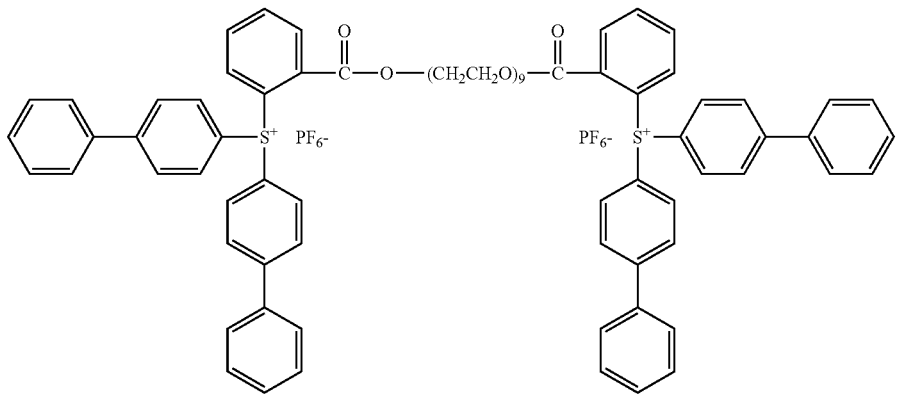

A mixture of 6 g of bis-biphenyl-4-yl-(2-methoxycarbonyl-phenyl)-sulfonium hexafluorophosphate (product of example 7), 1.94 g of (polyethyleneglycole) PEG 400, 0.15 g of lithium acetate and 0.16 g of tetrabutylammonium hydrogenosulfate is heated at 140-150° C. for 18 hrs under vacuum (20 mmHg). After 18 hrs another portion (0.1 g) of lithium acetate is added and the mixture is further heated at 160-170° C. under vacuum for 7 hrs. After cooling, the reaction mixture is dissolved in 100 ml acetone:dichloromethane=1:1 and 1.84 g $KPF_6$ is added. The mixture is stirred for 7 h, the solvent is evaporated and the product purified by gradient column chromatography on silica gel (diethyether:acetone(4:1)-diethylether:acetone:methanol (3:1:1), yielding 2 g of the desired product as an off-white powder.

$^1$H NMR (CDCl$_3$, 300 MHz) δ (ppm): 3.50-3.75 (28H, m, —OCH$_2$CH$_2$O—), 3.80-3.85 (4H, m, —COOCH$_2$CH$_2$O—), 4.46-4.51 (4H, m, —COOCH$_2$CH$_2$O), 7.34-7.50 (14H, m, ArH), 7.60-7.72 (16H, m, ArH), 7.86-7.91 (12H, m ArH), 8.44-8.47 (2H, m, ArH).

EXAMPLE 27

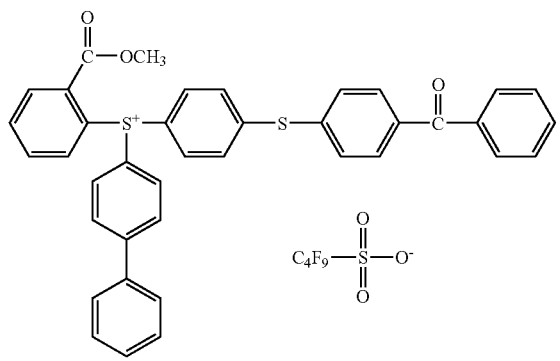

This compound is prepared similarly to example 6, replacing potassium hexafluorophosphate by potassium nonafluorobutanesulfonate. The product is a white solid, mp 77-81° C.

EXAMPLE 28

A composition is prepared by mixing the following components:
- 81.80 parts of 3,4-epoxycyclohexylmethyl carboxylate (UVR 6105, provided by Dow Chemical)
- 11.73 parts of 3-ethyl-3-hydroxymethyl-oxetane (UVR 6000, provided by Dow Chemical)
- 5.92 parts of ε-caprolactane triol (Tone Polyol 301, provided by Dow Chemical)
- 0.56 parts of a silicon surface additive (Byk 307, provided by BYK)
- 100.0 parts 1% of the compound of example 2 is stirred into said formulation, which then is applied with a layer thickness of 30cm onto a white chipboard. Curing is effected by irradiation with a 1×120 W/cm medium pressure mercury lamp (IST), aluminum reflector, by passing the sample under the lamp on a conveyor belt at a speed of 20 m/min.

The yellowing of the cured sample is determined by measuring the b* (CIE lab) value after the irradiation and after 16 h of additional exposure to a fluorescent tube (TLK40/05). The initial b* value is 3.8, while said value after 16 h of additional exposure is 4.4.

EXAMPLE 29

Into a formulation as described in example 282% of the compound of example 6 are stirred. The composition is then applied with a 4 μm wire bar onto an aluminum film (85cm). Curing is effected by moving the sample on a conveyor belt under an 1×120 W/cm medium pressure mercury lamp (IST) fitted with an aluminum reflector. Curing is tested by dry-rub resistance with Tela™ tissue paper. Belt speed is varied by 10 m/min steps. The higher the reactivity of the photoinitiator, the faster the belt can be moved to achieve a cured coating. With the described composition a cured coating is achieved even when the conveyor belt is moved with a speed of 200 m/min.

Using the photoinitiator compounds of examples 19 and 20 in the photocurable formulation, a belt speed of 200 m/min is achieved. With the photoinitiator compound of example 21 in the photocurable formulation, a belt speed of 180 m/min is achieved

EXAMPLE 30

Storage Stability of Photocurable Formulations Containing Photoinitiators of the Invention 210 mg of the photoinitiator compounds of examples 6, 19, 20, and 21 are each dissolved in 1.4 g of the photocurable formulation of example 28. Two samples are prepared for each photoinitiator compound. The resulting solutions are placed in closed vials, heated in an oven at 70° C., and visually tested for gellation. After 14 days, none of the solutions showed signs of polymerization.

What is claimed is:

1. A compound of the formula I, II, III or IV

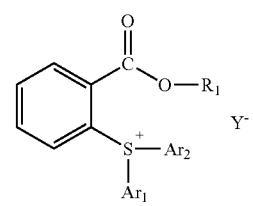
(I)

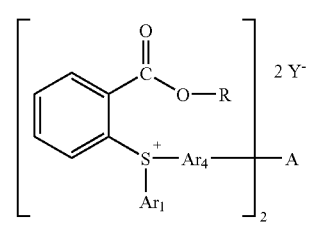
(II)

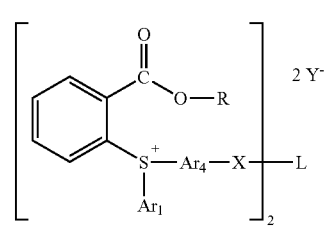
(III)

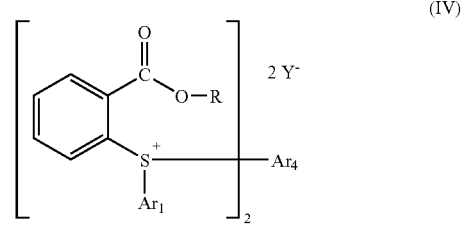
(IV)

wherein

R is hydrogen, C$_1$-C$_{20}$alkyl; C$_2$-C$_{20}$alkyl interrupted by one or more O; -L-X-R$_2$ or -L-R$_2$;

$R_1$ has one of the meanings as given for R or is

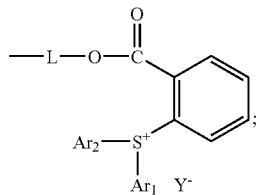

$R_2$ is a monovalent sensitizer or photoinitiator moiety;
$Ar_1$ and $Ar_2$ independently of one another are phenyl substituted by one or more $C_1$-$C_{20}$alkyl, halogen, $OR_3$ or $COOR_1$;
or are unsubstituted naphthyl, anthryl, phenanthryl or biphenylyl;
or are naphthyl, anthryl, phenanthryl or biphenylyl substituted by one or more $C_1$-$C_{20}$alkyl or $OR_3$;
or are -$Ar_4$-A-$Ar_3$ or

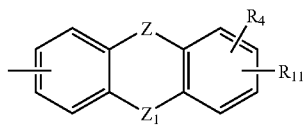

$Ar_3$ is unsubstituted phenyl, naphthyl, anthryl, phenanthryl or biphenylyl;
or is phenyl, naphthyl, anthryl, phenanthryl or biphenylyl substituted by one or more $C_1$-$C_{20}$alkyl, $OR_3$, $C_2$-$C_{12}$alkanoyl or benzoyl;
$Ar_4$ is phenylene, naphthylene, anthrylene or phenanthrylene;
A is a direct bond, S, O or $C_1$-$C_{20}$alkylene;
X is CO, C(O)O, OC(O), O, S or $NR_3$;
L is $C_1$-$C_{20}$alkylene or $C_2$-$C_{20}$alkylene interrupted by one or more O;
$R_3$ is $C_1$-$C_{20}$alkyl or $C_1$-$C_{20}$hydroxyalkyl; or is $C_1$-$C_{20}$alkyl substituted by $O(CO)R_{13}$;
Z is S, CO or $NR_3$;
$Z_1$ is a direct bond, $CH_2$, O or S;
$R_4$ and $R_{11}$ independently of one another are hydrogen, halogen, $C_1$-$C_8$alkyl, $C_1$-$C_8$alkoxy or phenyl;
$R_{13}$ is $C_1$-$C_{20}$alkyl; and
Y is an anion.

2. A compound of the formula I, II, III or IV, according to claim 1, wherein
Y is a halogenide, hydrogenosulfate, trifluoroacetate, or a non-nucleophilic anion, selected from the group $(BF_4)^-$, $(SbF_6)^-$, $(PF_6)^-$, $(B(C_6F_5)_4)$, $C_1$-$C_{20}$alkylsulfonate, $C_1$-$C_{20}$haloalkylsulfonate, unsubstituted $C_6$-$C_{10}$arylsulfonate, camphorsulfonate, $C_1$-$C_{20}$-perfluoroalkylsulfonylmethide, $C_1$-$C_{20}$-perfluoroalkylsulfonylimide, and $C_6$-$C_{10}$arylsulfonate substituted by halogen, $NO_2$, $C_1$-$C_{12}$alkyl, $C_1$-$C_{12}$haloalkyl, $C_1$-$C_{12}$alkoxy, phenylsulfonyloxy, $C_1$-$C_4$alkylphenylsulfonyloxy or by $COOR_{100}$; wherein $R_{100}$ is $C_1$-$C_{20}$alkyl, phenyl, benzyl; or phenyl mono- or poly-substituted by $C_1$-$C_{12}$alkyl, $C_1$-$C_{12}$alkoxy or by halogen.

3. A compound of the formula I, II, III or IV, according to claim 1, wherein $R_2$ denotes a group (a), (b), (c) or (d)

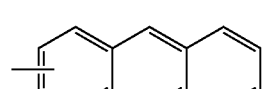

(a)

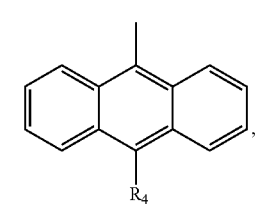

(b)

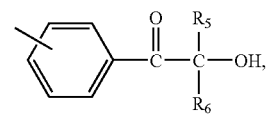

(c)

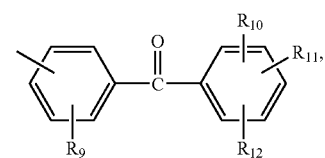

(d)

$R_4$ is hydrogen, $C_1$-$C_4$alkyl or $C_1$-$C_4$alkoxy;
$R_5$ and $R_6$ independently of one another are $C_1$-$C_{20}$alkyl, $C_2$-$C_{20}$alkenyl, phenylalkyl, alkyl-phenylalkyl, or $R_5$ and $R_6$ together with the C-atom to which they are attached form a ring;
$R_9$, $R_{10}$, $R_{11}$ and $R_{12}$ independently of one another are hydrogen, halogen, $C_1$-$C_8$alkyl or phenyl, or $R_9$ and $R_{10}$ together are methylene or S.

4. A compound of the formula I or II, according to claim 1, wherein
R is $C_1$-$C_{20}$alkyl;
$R_1$ is hydrogen, $C_1$-$C_{20}$alkyl; $C_2$-$C_{20}$alkyl interrupted by one or more O; -L-X—$R_2$; or is

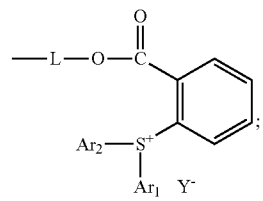

$R_2$ is a group (a) or (c)

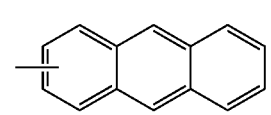

(a)

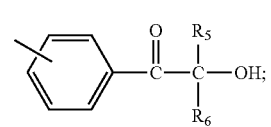

(c)

$Ar_1$ is phenyl substituted by one or more $OR_3$; or is biphenylyl or —$Ar_4$-A-$Ar_3$;

Ar$_2$ is phenyl substituted by one or more C$_1$-C$_{20}$alkyl; or is biphenylyl; —Ar$_4$-A-Ar$_3$ or

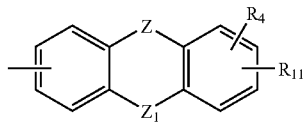

Ar$_3$ is unsubstituted phenyl; or is phenyl, substituted by acetyl or benzoyl;
Ar$_4$ is phenylene;
A is S or O;
X is O;
L is C$_1$-C$_{20}$alkylene or C$_2$-C$_{20}$alkylene interrupted by one or more O;
R$_3$ is C$_1$-C$_{20}$alkyl or C$_1$-C$_{20}$hydroxyalkyl; or is C$_1$-C$_{20}$alkyl substituted by O(CO)R$_{13}$;
R$_4$ and R$_{11}$ are hydrogen;
R$_{13}$ is C$_1$-C$_{20}$alkyl;
Z is NR$_3$;
Z$_1$ is a direct bond;
Y is PF$_6$ or C$_2$-C$_{20}$haloalkylsulfonate.

5. A radiation-sensitive composition comprising
(a1) a cationically or acid-catalytically polymerisable or crosslinkable compound or
(a2) a compound that increases its solubility in a developer under the action of acid; and
(b) at least one compound of the formula I, II, III or IV according to claim 1.

6. A radiation-sensitive composition according to claim 5, wherein component (a1) is at least one compound selected from the group of cycloaliphatic epoxy compounds, glycidyl ethers, oxetane compounds, vinyl ethers, acid-crosslinkable melamine resins, acid-crosslinkable hydroxymethylene compounds and acid-crosslinkable alkoxymethylene compounds.

7. A radiation-sensitive composition according to claim 5, wherein component (a2) is at least one compound selected from the group of cycloaliphatic copolymers, 4-hydroxyphenyl-group-containing copolymers, maleic acid anhydride-containing copolymers and acrylic acid-, acrylic acid ester- and methacrylic acid ester-containing copolymers, with the proviso that the copolymers carry functional groups that increase the solubility of the polymer in an alkaline developer after reaction with an acid.

8. A radiation-sensitive composition according to claim 5, additionally to components (a1) or (a2) and (b), comprising additional additives (c) and/or sensitiser compounds (d) and optionally further photoinitiators (e).

9. A method for the photopolymerisation or crosslinking of cationically or acid-catalytically polymerisable or crosslinkable compounds under the action of electromagnetic radiation or an electron beam, in which method a compound of formula I, II, III or IV according to claim 1 releases an acid upon radiation.

10. A coated substrate that is coated on at least one surface with a composition according to claim 5.

11. A method for the production of relief images, wherein a composition according to claim 5 is applied to a substrate and is then exposed image-wise.

12. A photoresist comprising a compound of formula I, II, III or IV according to claim 1 as radiation-sensitive acid donor.

13. Method according to claim 9 for the manufacture of surface-coating compositions, scratch-resistant coatings, stain-resistant coatings, antifog coatings, anticorrosion coatings, powder coating compositions, printing inks, non impact printing inks, ink jet printing inks, printing plates, dental compounds, composites for dental, composites, stereolithography resins, adhesives, anti-adhesive coatings, conformal coatings, optical fiber coatings, colour filters, resist materials or image-recording materials, holography resins.

* * * * *